(12) United States Patent
Graupe et al.

(10) Patent No.: US 10,071,985 B2
(45) Date of Patent: Sep. 11, 2018

(54) THERAPEUTIC COMPOUNDS

(71) Applicant: Gilead Sciences, Inc., Foster City, CA (US)

(72) Inventors: Michael Graupe, Pacifica, CA (US); Steven J. Henry, San Mateo, CA (US); John O. Link, San Francisco, CA (US); Charles William Rowe, San Bruno, CA (US); Roland D. Saito, San Mateo, CA (US); Scott D. Schroeder, Union City, CA (US); Dimitrios Stefanidis, Saratoga, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/680,041

(22) Filed: Aug. 17, 2017

(65) Prior Publication Data
US 2018/0051005 A1 Feb. 22, 2018

Related U.S. Application Data

(60) Provisional application No. 62/457,555, filed on Feb. 10, 2017, provisional application No. 62/377,312, filed on Aug. 19, 2016.

(51) Int. Cl.
*C07D 401/14* (2006.01)
*A61K 31/4439* (2006.01)
(Continued)

(52) U.S. Cl.
CPC ........ *C07D 401/14* (2013.01); *A61K 31/4439* (2013.01); *A61K 31/537* (2013.01);
(Continued)

(58) Field of Classification Search
CPC .................................................. C07D 401/14
(Continued)

(56) References Cited

U.S. PATENT DOCUMENTS

| 8,263,627 B2 | 9/2012 | Barrow et al. |
| 8,748,412 B2 | 6/2014 | Liao et al. |

(Continued)

FOREIGN PATENT DOCUMENTS

| WO | WO-2009/062285 A1 | 5/2009 |
| WO | WO-2010/130034 A1 | 11/2010 |

(Continued)

OTHER PUBLICATIONS

International Search Report and Written Opinion Issued in PCT/US2017/047416, dated Oct. 27, 2017, 10 pages.
(Continued)

*Primary Examiner* — Patricia L Morris
(74) *Attorney, Agent, or Firm* — Fish & Richardson P.C.

(57) ABSTRACT

The present disclosure relates to a compound of formula (Ia), (Ib), (IIa), and (IIb):

(Ia)

(Ib)

(IIa)

(Continued)

-continued (IIb)

which are useful in the treatment of a Retroviridae viral infection including an infection caused by the HIV virus.

25 Claims, 13 Drawing Sheets

(51) Int. Cl.
| | |
|---|---|
| *A61K 31/537* | (2006.01) |
| *A61K 31/675* | (2006.01) |
| *A61K 31/7076* | (2006.01) |
| *A61K 45/06* | (2006.01) |
| *C07C 317/08* | (2006.01) |
| *C07D 231/54* | (2006.01) |
| *C07F 5/02* | (2006.01) |

(52) U.S. Cl.
CPC ........ *A61K 31/675* (2013.01); *A61K 31/7076* (2013.01); *A61K 45/06* (2013.01); *C07C 317/08* (2013.01); *C07D 231/54* (2013.01); *C07F 5/025* (2013.01)

(58) Field of Classification Search
USPC ........................................ 546/275.7; 514/338
See application file for complete search history.

(56) References Cited

U.S. PATENT DOCUMENTS

| | | | |
|---|---|---|---|
| 8,835,488 | B2 | 9/2014 | Yamashita et al. |
| 9,012,441 | B2 | 4/2015 | Bondy et al. |
| 9,050,344 | B2 | 6/2015 | Brizgys et al. |
| 9,220,710 | B2 | 12/2015 | Bondy et al. |
| 9,540,343 | B2 | 1/2017 | Bondy et al. |
| 9,789,089 | B2 | 10/2017 | Bondy et al. |
| 9,944,619 | B2 | 4/2018 | Bondy et al. |
| 9,951,043 | B2 * | 4/2018 | Brizgys ............... C07D 401/12 |
| 2010/0249176 | A1 | 9/2010 | Barrow et al. |
| 2012/0045761 | A1 | 2/2012 | Jagannath et al. |
| 2013/0165489 | A1 | 6/2013 | Cocklin et al. |
| 2014/0142085 | A1 | 5/2014 | Bondy et al. |
| 2014/0221346 | A1 | 8/2014 | Halcomb et al. |
| 2014/0296266 | A1 | 10/2014 | Hu et al. |
| 2014/0303164 | A1 | 10/2014 | Brizgys et al. |
| 2016/0067224 | A1 | 3/2016 | Bondy et al. |
| 2016/0083368 | A1 | 3/2016 | Brizgys et al. |
| 2016/0368881 | A1 | 12/2016 | Bondy et al. |

FOREIGN PATENT DOCUMENTS

| | | | |
|---|---|---|---|
| WO | WO-2011/143772 | A1 | 11/2011 |
| WO | WO-2012/003497 | A1 | 1/2012 |
| WO | WO-2012/003498 | A1 | 1/2012 |
| WO | WO-2012065062 | A1 | 5/2012 |
| WO | WO-2012/145728 | A1 | 10/2012 |
| WO | WO-2013/006738 | A1 | 1/2013 |
| WO | WO-2013/006792 | A1 | 1/2013 |
| WO | WO-2013006738 | A1 | 1/2013 |
| WO | WO-2013/159064 | A1 | 10/2013 |
| WO | WO-2014/016358 | A1 | 1/2014 |
| WO | WO-2014/028931 | A2 | 2/2014 |
| WO | WO-2014134566 | A2 | 9/2014 |
| WO | WO-2015/008097 | A1 | 1/2015 |
| WO | WO-2015/061518 | A1 | 4/2015 |
| WO | WO-2015/130966 | A1 | 9/2015 |
| WO | WO-2016/040084 | A1 | 3/2016 |
| WO | WO-2016/172424 | A1 | 10/2016 |
| WO | WO-2016/172425 | A1 | 10/2016 |
| WO | WO 2017/007689 | | 1/2017 |

OTHER PUBLICATIONS

Owen et al., "Strengths, weaknesses, opportunities and challenges for long acting injectable therapies: Insights for applications in HIV therapy," Advanced Drug Delivery Reviews 103 (2016) 144-156.
SUBLOCADE Product Label, issued Nov. 2017, 43 pages.
Berge, S.M. et al. (1977) "Pharmaceutical Salts," *J. Pharma. Sci.* 66(1):1-19.
Brown, M.K. et al. ( 2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," *Angew Chem. Int. Ed. Engl.* 44(33):5306-5310.
Cos, P. et al. (1998) "Structure-Activity Relationship and Classification of Flavonoids as Inhibitors of Xanthine Oxidase and Superoxide Seavengers," J. Natl. Prod. 61:71-76.
First Examination Report dated Nov. 2, 2015 for New Zealand Patent Application No. 631754.
Hammer, S.M. et al. (2008) "Antiretroviral Treatment of Adult HIV Infection: 2008 Recommendations of the International AIDS Society-USA Panel," JAMA 300(5):555-570.
Hodgson, D.M. et al. (2007) "Intramolecular Cyclopropanation of Unsaturated Terminal Epoxides and Chlorohydrins," *JACS* 129(14):4456-4462.
International Search Report and Written Opinion dated Oct. 14, 2014 for PCT/US2014/019663.
Jeong, .J.U. (2010) "Synthesis of Tetrasubstituted Pyrazones and Pyrazone N-Oxides," *Tetrahedron Letters* 51(6):974-976.
Lemke, C.T. et al. (2012) "Distinct Effects of Two HIV-1 Capsid Assembly Inhibitor Families That Bind the Same Site Within the N-Terminal Domain of the Viral CA Protein," J. Virol. 86(12):6643-6655.
Notification No. 34475 dated Oct. 13, 2015 for Vietnam Patent Application No. 1-2015-03220.
Office Action dated Dec. 7, 2015 for Colombian Patent Application No. 15-199.357 1 with English translaton.
Office Action dated Jun. 4, 2015 for U.S. Appl. No. 14/194,611.
Office Action dated Jun. 19, 2015 for U.S. Appl. No. 14/194,623.
Office Action dated Dec. 1, 2015 for Australian Patent Application No. 2014223973.
Office Action dated Dec. 4, 2015 for EP14712844.1-1462.
Office Action dated Dec. 7, 2015 for Colombian Patent Application No. 15-199.357 1.
Office Action dated Dec. 7, 2015 for Colombian Patent Application No. 15-199.357 1—English.
Powers, J.J. et al. (2009) "Synthesis of Methyl-, Fluoro-, and Chloro-Substituted 6-Hydroxyisoindolin-1-Ones," *Tetrahedron Letters* 50(12):1267-1269.
Siddiqui, A. et al. (1999) "The Presence of SUbstituents on the Aryl Moiety of the Aryl Phosphoramidate Derivative of d4T Enhances Anti-HIV Efficacy in Cell Culture: A Structure-Activity Relationship" J. Med. Chem. 42:393-399.

(56) References Cited

OTHER PUBLICATIONS

Smith, R.J. et al. (2010) "Evolutionary Dynamics of Complex Networks of HIV Drug-Resistant Strains: The Case of San Francisco," *Science* 327(5966):697-701.
Taiwo, B. (2009) "Understanding Transmitted HIV Resistance Through the Experience in the USA," *Int. J. Infect. Dis.* 13(5):552-559.
Tanaka, R. et al. (2005) "One-Pot Synthesis of Metalated Pyridines from Two Acetylenes, a Nitrile, and a Titanium(II) Alkoxide," *J. Am. Chem. Soc.* 127(21):7774-7780.
Offce Action dated Jun. 28, 2016 for Eurasian Patent Application No. 201591457/28.
Office Action dated Sep. 8, 2016 for Colombia Application No. 15199357.
Office Action dated Sep. 8, 2016 English Translation for Colombia Application No. 15199357.
Bhattacharya et al. (2014) Structural Basis of HIV-1 Capsid Recognition by PF74 and CPSF6, *PNAS*; 111(52):18625-18630.
Blair et al., (2010) "HIV Capsid is a Tractable Target for Small Molecule Therapeutic Intervention," *PLoS Pathog.* 6(12): e1001220.
Briggs et al., (2003) "Structural Organization of Authentic, Mature HIV-1 Virions and Cores," *The EMBO Journal*; vol. 22 No. 7 pp. 1707-1715.
Campbell et al., (2015) "HIV1 Capsid: The Multifaceted Key Player in HIV1 Infection," *Nat Rev Microbiol.*; 13(8): 471-483.
Chin et al. (2015) "Direct Visualization of HIV-1 Replicatioin Intermediates Shows That Capsid and CPSF6 Modulate HIV-1 Intra-Nuclear Invasion and Integration", *Cell Reports* 13:1717-1731.
Curreli et al., (2011) "Virtual Screening Based Identification of Novel Small-molecule Inhibitors Targeted to the HIV-1 Capsid," *Bioorganic & Medicinal Chemistry* 19:77-90.
Fader et al., (2013) Optimization of a 1,5-dihydrobenzo[b][1,4]diazepine-2,4-dione Series of HIV Capsid Assembly Inhibitors 2: Structure-Activity Relationships (SAR) of the C3-Phenyl Moiety, *Bioorganic & Medicinal Chemistry Letters*, doi: <http://dx.doi.org/10.1016/j.bmcl.2013.03.074>.
Forshey et al., (2002) "Formation of a Human Immunodeficiency Virus Type 1 Core of Optimal Stability Is Crucial for Viral Replication," *J. Virology*, 76(11) p. 5667-5677.
Ganser et al., (1999) "Assembly and Analysis of Conical Models for the HIV-1 Core," *Science* 283, 80-82.
Ganser-Pornillos et al., (2007) "Structure of Full-Length HIV-1 CA: A Model for the Mature Capsid Lattice," *Cell.*; 131(1):70-9.
Jin et al., (2010) "SAR and Molecular Mechanism Study of Novel Acylhydrazone Compounds Targeting HIV-1 CA," *Bioorganic & Medicinal Chemistry*; 18: 2135-2140.
Jouvenet et al., (2006) "Plasma Membrane Is the Site of Productive HIV-1 Particle Assembly," *PLoS Biol.*;4(12):e435.
Kelly, et al., (2007) "Structure of the Antiviral Assembly Inhibitor CAP-1 Bound to the HIV-1 CA Protein," *Journal of Molecular Biology*, doi: 10.1016/j.jmb.2007.07.070.
Kim et al., (2013) "Discovery of a New HIV-1 Inhibitor Scaffold and Synthesis of Potential Prodrugs of Indazoles," *Bioorganic & Medicinal Chemistry Letters*, doi: <http://dx.doi.org/10.1016/j.bmcl.2013.03.075>.
Lamorte et al. (2015) "Discovery of Novel Small-Molecule HIV-1 Replication Inhibitors That Stabilize Capsid Complexes" *Antimicrobial Agents and Chemotherapy*, 57(10): 4622-4631.
Lazerwith et al., (2017) "New Antiretrovirals for HIV and Antivirals for HBV," in Comprehensive Medicinal Chemistry, 3rd Edition, 1-36.
Lee et al., (2010) "Flexible Use of Nuclear Import Pathways by HIV-1," *Cell Host & Microbe*; 7, 221-233.
Office Action dated Mar. 30, 2017 for Chile Application No. 2445-2015. (Spanish).
Office Action dated Mar. 30, 2017 for Chile Application No. 2445-2015. (English).
Office Action dated Aug. 17, 2016 for Eurasian Patent Application No. 201591457. (Russian).
Office Action dated Aug. 17, 2016 for Eurasian Patent Application No. 201591457. (English).
Office Action dated Mar. 29, 2017 for European Patent Application No. 14712844.1.
Office Action dated Feb. 22, 2017 for New Zealand Application No. 728537.
Office Action dated Mar. 28, 2017 for Panama Application No. 90820-01. (Spanish).
Office Action dated Mar. 28, 2017 for Panama Application No. 90820-01. (English).
Pornillos et al., (2009) "X-ray Structures of the Hexameric Building Block of the HIV Capsid" *Cell.*; 137(7):1282-92.
Pornillos et al., (2009) Supplemental Data for "X-ray Structures of the Hexameric Building Block of the HIV Capsid" Cell. Jun. 26, 2009;137(7):1282-92.
Price et al. (2012) "CPSF6 Defines a Conserved Capsid Interface That Modulates HIV-1 Replication" *PLOS Pathogens*, 8(8):e1002896.
Shi et al., (2011) "Small-Molecule Inhibition of Human Immunodeficiency Virus Type 1 Infection by Virus Capsid Destabilization," *J. Virology*, p. 542-549.
Tang et al., (2003) "Antiviral Inhibition of the HIV-1 Capsid Protein," *J. Mol. Biol.*, 327, 1013-1020.
Tse et al., (2017) "Discovery of Novel Potent HIV Capsid Inhibitors with Long-Acting Potential," Oral Presentation at the Conference on Retroviruses and Opportunistic Infections (CROI), Seattle, WA.
Tse et al., (2017) "Discovery of Novel Potent HIV Capsid Inhibitors with Long-Acting Potential," Abstract for Oral Presentation at the Conference on Retroviruses and Opportunistic Infections (CROI), Seattle, WA.
U.S. Appl. No. 15/357,290 (Not attached).
Wong et al., (2014) "SPR Assay Development to Characterize Capsid Inhibitors Binding & MOA," Poster Presented at the Developments in Protein Interaction (DiPIA), La Jolla, CA.
Zhou et al. (2015) "HIV-1 Resistance to the Capsid-Targeting Inhibitor PF74 Results in Altered Dependence on Host Factors Required for Virus Neclear Entry" *Journal of Virology*, doi 10.1128/JVI.00340-15.
Hung et al. (2013) "Large-Scale Functional Purification of Recombinant HIV- 1 Capsid" *PLOS One*, vol. 8, Issue 3, e58035.
Lad et al., (2015) "Functional Label-Free Assays for Characterizing the in Vitro Mechanism of Action of Small Molecule Modulators of Capsid Assembly" *Biochemistry*, 54, 2240-2248.
Matreyek et al., (2013) "Nucleoporin NUP153 Phenylalanine-Glycine Motifs Engage a Common Binding Pocket within the HIV-1 Capsid Protein to Mediate Lentiviral Infectivity" *PLOS Pathogens* vol. 91 | Issue 10 | e1003693.
Office Action dated Jan. 16, 2017 for Chinese Application No. 201480020587.0.
English language translation of Office Action dated Jan. 16, 2017 for Chinese Application No. 201480020587.0.
Search Report dated Jan. 6, 2017 for Chinese Application No. 201480020587.0.
English language translation of Search Report dated Jan. 6, 2017 for Chinese Application No. 201480020587.0.
Pre-grant opposition dated Jun. 15, 2016 for Chilean Application No. 2445-2015.
English language translation of Pre-grant opposition dated Jun. 15, 2016 for Chilean Application No. 2445-2015.
Rihn et al., (2013) "Extreme Genetic Fragility of the HIV-1 Capsid" *PLOS One*, vol. 9 Issue 6 e1003461.
Sticht et al., (2005) "A peptide inhibitor of HIV-1 assembly in vitro" *Nature Structural & Molecular Biology*, vol. 12 No. 8 671-677.
Tsiang et al., (2012) "A Trimer of Dimers Is the Basic Building Block for Human Immunodeficiency Virus-1 Capsid Assembly" *Biochemistry*, 51, 4416-4428.
Yant et al., (2014) "An Improved PF74 Analog Inhibits Multiple HIV Capsid Functions Independently of Host Cyclophilin A and CPSF6" Poster Presented at the Conference on Retroviruses and Opportunistic Infections (CROI), Boston, Massachusetts.

(56) References Cited

OTHER PUBLICATIONS

Yant et al., (2014) "PF74 Inhibits Multiple HIV Capsid Functions Independently of Host Cyclophilin A and CPSF6" Abstract for Poster Presented at the Conference on Retroviruses and Opportunistic Infections (CROI), Boston, Massachusetts.
Office Action dated Apr. 12, 2017 for Gulf Cooperation Council Application No. 2014/26552.
European Communication in European Appln. No. 17758388, dated May 15, 2018, 5 pages.

* cited by examiner

Concentration over time of 200 mg/mL of Formula Ib, sodium salt form suspended in 2% Poloxamer 188 in saline formulation, after subcutaneous dosing in dogs at 6mg/kg

THERAPEUTIC COMPOUNDS

CROSS-REFERENCE TO RELATED APPLICATIONS

This application claims priority benefit to U.S. Provisional Application Ser. No. 62/377,312, filed on Aug. 19, 2016 and to U.S. Provisional Application Ser. No. 62/457,555, filed Feb. 10, 2017, the disclosures of which are incorporated by reference in their entireties

FIELD

The present disclosure relates to novel compounds for use in the treatment of a Retroviridae viral infection including an infection caused by the HIV virus. The present disclosure also relates to intermediates for its preparation and to pharmaceutical compositions containing said novel compound.

BACKGROUND

Positive-single stranded RNA viruses comprising the Retroviridae family include those of the subfamily Orthoretrovirinae and genera *Alpharetrovirus, Betaretrovirus, Gammaretrovirus, Deltaretrovirus, Epsilonretrovirus, Lentivirus,* and *Spumavirus* which cause many human and animal diseases. Among the *Lentivirus*, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants.

U.S. Patent Publication No. 2014/0296266A1, published Oct. 2, 2014, discloses compounds useful for treating a Retroviridae viral infection including an infection caused by the HIV virus. U.S. Patent Publication 2014/0296266A1 relates to, among other things, compounds of Formula I:

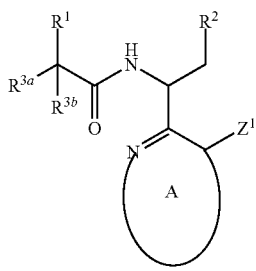

wherein:
A is a 6-membered monocyclic-heteroaryl with one or two nitrogen atoms, wherein the 6-membered monocyclic-heteroaryl is substituted with one $Z^1$ group at the position shown, one $Z^2$ group, and optionally substituted with one or more (e.g., 1 or 2) $Z^3$ groups;

$R^1$ is 6-12 membered aryl, 5-12 membered heteroaryl or 3-12 membered heterocycle, wherein any 6-12 membered aryl, 5-12 membered heteroaryl or 3-12 membered heterocycle of $R^1$ is optionally substituted with one or more (e.g., 1, 2, 3, 4 or 5) $Z^4$ groups;

$R^2$ is phenyl, 5-membered monocyclic-heteroaryl, 6-membered monocyclic-heteroaryl or $(C_3-C_7)$carbocycle, wherein any phenyl, 5-membered monocyclic-heteroaryl, 6-membered monocyclic-heteroaryl or $(C_3-C_7)$carbocycle of $R^2$ is optionally substituted with one or more (e.g., 1, 2, 3, 4 or 5) $Z^5$ groups;

each $R^{3a}$ and $R^{3b}$ is independently selected from H, halogen, $(C_1-C_3)$alkyl and $(C_1-C_3)$haloalkyl, or $R^{3a}$ is selected from H, $(C_1-C_3)$alkyl and $(C_1-C_3)$haloalkyl and $R^{3b}$ is selected from —OH and —CN;

$Z^1$ is selected from 6-12 membered aryl, 5-14 membered heteroaryl and 3-14 membered heterocycle, wherein any 6-12 membered aryl, 5-14 membered heteroaryl and 3-14 membered heterocycle of $Z^1$ is optionally substituted with one or more (e.g., 1, 2, 3, 4 or 5) $Z^{1a}$ or $Z^{1b}$;

each $Z^{1a}$ is independently selected from $(C_3-C_7)$carbocycle, 6-12 membered aryl, 5-12 membered heteroaryl, 3-12 membered heterocycle, halogen, —CN, —$OR^{n1}$, —OC(O)$R^{p1}$, —OC(O)$NR^{q1}R^{r1}$, —$SR^{n1}$, —S(O)$R^{p1}$, —S(O)$_2$OH, —S(O)$_2R^{p1}$, —S(O)$_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, $NO_2$, —C(O)$R^{n1}$, —C(O)$OR^{n1}$, —C(O)$NR^{q1}R^{r1}$ and —S(O)$_2NR^{n1}COR^{p1}$, wherein any $(C_3-C_7)$carbocycle, 6-12 membered aryl, 5-12 membered heteroaryl and 3-12 membered heterocycle of $Z^{1a}$ is optionally substituted with one or more (e.g., 1, 2, 3, 4 or 5) $Z^{1c}$ or $Z^{1d}$ groups;

each $Z^{1b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{1b}$ is optionally substituted with one or more (e.g., 1, 2, 3, 4 or 5) $Z^{1c}$ groups;

each $Z^{1c}$ is independently selected from $(C_3-C_7)$carbocycle, phenyl, 5-6 membered monocyclic-heteroaryl, 3-7 membered heterocycle, halogen, —CN, —$OR^{n2}$, —OC(O)$R^{p2}$, —OC(O)$NR^{q2}R^{r2}$, —$SR^{n2}$, —S(O)$R^{p2}$, —S(O)$_2$OH, —S(O)$_2R^{p2}$, —S(O)$_2NR^{q2}R^{r2}$, —$NR^{q2}R^{r2}$, —$NR^{n2}COR^{p2}$, —$NR^{n2}CO_2R^{p2}$, —$NR^{n2}CONR^{q2}R^{r2}$, —$NR^{n2}S(O)_2R^{p2}$, —$NR^{n2}S(O)_2OR^{p2}$, —$NR^{n2}S(O_2NR^{q2}R^{r2}$, $NO_2$, —C(O)$R^{n2}$, —C(O)$OR^{n2}$, —C(O)$NR^{q2}R^{r2}$, halophenyl, 5-6 membered haloheteroaryl, 3-7 membered haloheterocycle and $(C_1-C_8)$heteroalkyl;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R^{n1}$ is independently selected from H, $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{n1}$ is optionally substituted with one or more (e.g., 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R^{n1}$ is optionally substituted with one or more (e.g., 1, 2, 3, 4 or 5) $Z^{1c}$ groups;

each $R^{p1}$ is independently selected from $(C_1-C_8)$alkyl, $(C_2-C_8)$alkenyl, $(C_2-C_8)$alkynyl, $(C_3-C_7)$carbocycle, 3-7 membered heterocycle, 5-6 membered monocyclic-heteroaryl and phenyl, wherein any $(C_3-C_7)$carbocycle, 3-7 membered heterocycle, 5-6 membered monocyclic-heteroaryl and phenyl of $R^{p1}$ is optionally substituted with one or more (e.g., 1, 2, 3, 4 or 5) $Z^{1c}$ or $Z^{1d}$ groups, and wherein any $(C_1$-$C_8)$alkyl, $(C_2$-$C_8)$alkenyl and $(C_2$-$C_8)$alkynyl of $R^{p1}$ is optionally substituted with one or more (e.g., 1, 2, 3, 4 or 5) $Z^{1c}$ groups;

$R^{q1}$ and $R^{r1}$ are each independently selected from H, $(C_1$-$C_8)$alkyl, $(C_2$-$C_8)$alkenyl, $(C_2$-$C_8)$alkynyl, $(C_3$-$C_7)$carbocycle, 3-7 membered heterocycle, 5-6 membered monocyclic-heteroaryl and phenyl, wherein any $(C_3$-$C_7)$carbocycle, 3-7 membered heterocycle, 5-6 membered monocyclic-heteroaryl and phenyl of $R^{q1}$ or $R^{r1}$ is optionally substituted with one or more (e.g., 1, 2, 3, 4 or 5) $Z^{1c}$ or $Z^{1d}$ groups, and wherein any $(C_1$-$C_8)$alkyl, $(C_2$-$C_8)$alkenyl and $(C_2$-$C_8)$alkynyl of $R^{q1}$ or $R^{r1}$ is optionally substituted with one or more (e.g., 1, 2, 3, 4 or 5) $Z^{1c}$ groups, or $R^{q1}$ and $R^{r1}$ together with the nitrogen to which they are attached form a 5, 6 or 7-membered heterocycle, wherein the 5, 6 or 7-membered heterocycle is optionally substituted with one or more (e.g., 1, 2, 3, 4 or 5) $Z^{1c}$ or $Z^{1d}$ groups;

each $R^{n2}$ is independently selected from H, $(C_1$-$C_8)$alkyl, $(C_2$-$C_8)$alkenyl, $(C_2$-$C_8)$alkynyl, $(C_3$-$C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1$-$C_8)$haloalkyl and $(C_1$-$C_8)$heteroalkyl;

each $R^{p2}$ is independently selected from $(C_1$-$C_8)$alkyl, $(C_2$-$C_8)$alkenyl, $(C_2$-$C_8)$alkynyl, $(C_3$-$C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1$-$C_8)$haloalkyl and $(C_1$-$C_8)$heteroalkyl;

$R^{q2}$ and $R^{r2}$ are each independently selected from H, $(C_1$-$C_8)$alkyl, $(C_2$-$C_8)$alkenyl, $(C_2$-$C_8)$alkynyl, $(C_3$-$C_7)$carbocycle, 3-7 membered heterocycle, 5-6 membered monocyclic-heteroaryl, phenyl, halophenyl, 5-6 membered monocyclic-haloheteroaryl, 3-7 membered haloheterocycle, $(C_1$-$C_8)$haloalkyl and $(C_1$-$C_8)$heteroalkyl, or $R^{q2}$ and $R^{r2}$ together with the nitrogen to which they are attached form a 5, 6 or 7-membered heterocycle;

$Z^2$ is selected from $(C_2$-$C_8)$alkenyl, $(C_2$-$C_8)$alkynyl, 6-12 membered aryl, 5-12 membered C-linked-heteroaryl, 3-12 membered C-linked-heterocycle, —C(O)$R^{n3}$ and —C(O)NR$^{q3}$R$^{r3}$, wherein any 6-12 membered aryl, 5-12 membered C-linked-heteroaryl and 3-12 membered C-linked-heterocycle of $Z^2$ is optionally substituted with one or more (e.g., 1, 2, 3, 4 or 5) $Z^{2b}$ or $Z^{2c}$ groups, and wherein any $(C_2$-$C_8)$alkenyl and $(C_2$-$C_8)$alkynyl of $Z^2$ is optionally substituted with one or more (e.g., 1, 2, 3, 4, or 5) $Z^{2c}$ groups;

each $Z^{2a}$ is independently selected from $(C_3$-$C_7)$carbocycle, 6-12 membered aryl, 5-12 membered heteroaryl, 3-12 membered heterocycle, halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$, wherein any $(C_3$-$C_7)$carbocycle, 6-12 membered aryl, 5-12 membered heteroaryl and 3-12 membered heterocycle of $Z^{2a}$ is optionally substituted with one or more (e.g., 1, 2, 3, 4 or 5) $Z^{2b}$ or $Z^{2c}$ groups;

each $Z^{2b}$ is independently selected from $(C_1$-$C_4)$alkyl, $(C_1$-$C_4)$heteroalkyl and $(C_1$-$C_4)$haloalkyl;

each $Z^{2c}$ is independently selected from halogen, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$ and —C(O)NR$^{q4}$R$^{r4}$;

each $R^{n3}$ is independently selected from H, $(C_1$-$C_4)$alkyl, $(C_2$-$C_4)$alkenyl, $(C_3$-$C_7)$carbocycle, 3-12 membered heterocycle, 5-12 membered heteroaryl and 6-12 membered aryl, wherein any $(C_3$-$C_7)$carbocycle, 3-12 membered heterocycle, 5-12 membered heteroaryl and 6-12 membered aryl of $R^{n3}$ is optionally substituted with one or more (e.g., 1, 2, 3, 4 or 5) $Z^{2b}$ or $Z^{2c}$ groups, and wherein any $(C_1$-$C_4)$alkyl, $(C_2$-$C_4)$alkenyl and $(C_2$-$C_4)$alkynyl of $R^{n3}$ is optionally substituted with one or more (e.g., 1, 2, 3, 4 or 5) $Z^{2a}$ groups;

$R^{q3}$ and $R^{r3}$ are each independently selected from H, $(C_1$-$C_4)$alkyl, $(C_2$-$C_4)$alkenyl, $(C_3$-$C_7)$carbocycle, 3-12 membered heterocycle, 5-12 membered heteroaryl and 6-12 membered aryl, wherein any $(C_3$-$C_7)$carbocycle, 3-12 membered heterocycle, 5-12 membered heteroaryl and 6-12 membered aryl of $R^{q3}$ or $R^{r3}$ is optionally substituted with one or more (e.g., 1, 2, 3, 4 or 5) $Z^{2b}$ or $Z^{2c}$ groups, and wherein any $(C_1$-$C_4)$alkyl and $(C_2$-$C_4)$alkenyl of $R^{q3}$ or $R^{r3}$ is optionally substituted with one or more (e.g., 1, 2, 3, 4 or 5) $Z^{2a}$ groups, or $R^{q3}$ and $R^{r3}$ together with the nitrogen to which they are attached form a heterocycle or heteroaryl, wherein the heterocycle or heteroaryl is optionally substituted with one or more (e.g., 1, 2, 3, 4 or 5) $Z^{2b}$ or $Z^{2c}$ groups;

each $R^{n4}$ is independently selected from H, $(C_1$-$C_4)$alkyl, $(C_2$-$C_8)$alkenyl, $(C_2$-$C_8)$alkynyl, $(C_1$-$C_4)$haloalkyl and $(C_1$-$C_4)$heteroalkyl;

each $R^{p4}$ is independently selected from $(C_1$-$C_8)$alkyl, $(C_2$-$C_4)$alkenyl, $(C_2$-$C_4)$alkynyl, $(C_1$-$C_4)$haloalkyl and $(C_1$-$C_4)$heteroalkyl;

$R^{q4}$ and $R^{r4}$ are each independently selected from H, $(C_1$-$C_4)$alkyl, $(C_2$-$C_4)$alkenyl, $(C_2$-$C_4)$alkynyl, $(C_1$-$C_4)$haloalkyl and $(C_1$-$C_4)$heteroalkyl;

each $Z^3$ is independently selected from halogen, $(C_1$-$C_4)$alkyl, —OH, —CN, $(C_1$-$C_4)$heteroalkyl and $(C_1$-$C_4)$haloalkyl;

each $Z^4$ is independently selected from $(C_1$-$C_8)$alkyl, $(C_2$-$C_8)$alkenyl, $(C_2$-$C_8)$alkynyl, $(C_3$-$C_7)$carbocycle, halogen, —CN, —OR$^{n5}$, —OC(O)R$^{p5}$, —OC(O)NR$^{q5}$R$^{r5}$, —SR$^{n5}$, —S(O)R$^{p5}$, —S(O)$_2$OH, —S(O)$_2$R$^{p5}$, —S(O)$_2$NR$^{q5}$R$^{r5}$, —NR$^{q5}$R$^{r5}$, —NR$^{n5}$COR$^{p5}$, —NR$^{n5}$CO$_2$R$^{p5}$, —NR$^{n5}$CONR$^{q5}$R$^{r5}$, —NR$^{n5}$S(O)$_2$R$^{p5}$, —NR$^{n5}$S(O)$_2$OR$^{p5}$, —NR$^{n5}$S(O)$_2$NR$^{q5}$R$^{r5}$, NO$_2$, —C(O)R$^{n5}$, —C(O)OR$^{n5}$ and —C(O)NR$^{q5}$R$^{r5}$, wherein any $(C_3$-$C_7)$carbocycle, of $Z^4$ is optionally substituted with one or more (e.g., 1, 2, 3, 4 or 5) $Z^{4a}$ or $Z^{4b}$ groups, and wherein any $(C_1$-$C_8)$alkyl, $(C_2$-$C_8)$alkenyl and $(C_2$-$C_8)$alkynyl of $Z^4$ is optionally substituted with one or more (e.g., 1, 2, 3, 4 or 5) $Z^{4a}$ groups;

each $Z^{4a}$ is independently selected from halogen, —CN, —OR$^{n6}$, —OC(O)R$^{p6}$, —OC(O)NR$^{q6}$R$^{r6}$, —SR$^{n6}$, —S(O)R$^{p6}$, —S(O)$_2$OH, —S(O)$_2$R$^{p6}$, —S(O)$_2$NR$^{q6}$R$^{r6}$, —NR$^{q6}$R$^{r6}$, —NR$^{n6}$COR$^{p6}$, —NR$^{n6}$CO$_2$R$^{p6}$, —NR$^{n6}$CONR$^{q6}$R$^{r6}$, —NR$^{n6}$S(O)$_2$R$^{p6}$, —NR$^{n6}$S(O)$_2$OR$^{p6}$, —NR$^{n6}$S(O)$_2$NR$^{q6}$R$^{r6}$, NO$_2$, —C(O)R$^{n6}$, —C(O)OR$^{n6}$ and —C(O)NR$^{q6}$R$^{r6}$;

each $Z^{4b}$ is independently selected from $(C_1$-$C_4)$alkyl, $(C_2$-$C_4)$alkenyl $(C_2$-$C_4)$alkynyl and $(C_1$-$C_4)$haloalkyl;

each $R^{n5}$ is independently selected from H, $(C_1$-$C_4)$alkyl, $(C_1$-$C_4)$haloalkyl, $(C_1$-$C_4)$heteroalkyl, $(C_2$-$C_4)$alkenyl and $(C_2$-$C_4)$alkynyl;

each $R^{p5}$ is independently selected from $(C_1$-$C_4)$alkyl, $(C_1$-$C_4)$haloalkyl, $(C_1$-$C_4)$heteroalkyl, $(C_2$-$C_4)$alkenyl and $(C_2$-$C_4)$alkynyl;

$R^{q5}$ and $R^{r5}$ are each independently selected from H, $(C_1$-$C_4)$alkyl, $(C_1$-$C_4)$haloalkyl, $(C_1$-$C_4)$heteroalkyl, $(C_2$-$C_4)$alkenyl and $(C_2$-$C_4)$alkynyl;

each $R^{n6}$ is independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $R^{p6}$ is independently selected from $(C_1-C_4)$alkyl, $(C_1-C_4)$haloalkyl, $(C_1-C_4)$heteroalkyl, $(C_2-C_4)$alkenyl and $(C_2-C_4)$alkynyl;

$R^{q6}$ and $R^{r6}$ are each independently selected from H, $(C_1-C_4)$alkyl, $(C_1-C_4)$haloalkyl, $(C_1-C_4)$heteroalkyl, $(C_2-C_4)$alkenyl and $(C_2-C_4)$alkynyl;

each $Z^5$ is independently selected from $(C_1-C_6)$alkyl, halogen, —CN and —$OR^{n7}$, wherein any $(C_1-C_6)$alkyl of $Z^5$ is optionally substituted with one or more (e.g., 1, 2, 3, 4 or 5) halogen; and each $R^{n7}$ is independently selected from H, $(C_1-C_3)$alkyl, $(C_1-C_3)$haloalkyl and $(C_3-C_7)$carbocycle;

or a pharmaceutically acceptable salt thereof.

U.S. Patent Publication No. 2014/0303164A1, published Oct. 9, 2014, discloses compounds useful for treating a Retroviridae viral infection including an infection caused by the HIV virus. U.S. Patent Publication 2014/0303164A1 relates to, among other things, compounds of Formula IIId:

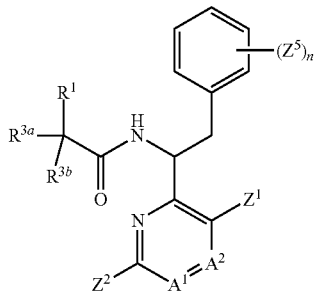

IIId wherein $A^1$ is CH, C—$Z^3$, or nitrogen;

$A^2$ is CH or nitrogen;

$R^1$ is 6-12 membered aryl, 5-12 membered heteroaryl, or 3-12 membered heterocycle, wherein any 6-12 membered aryl, 5-12 membered heteroaryl, or 3-12 membered heterocycle of $R^1$ is optionally substituted with 1, 2, 3, 4 or 5 $Z^4$ groups, wherein the $Z^4$ groups are the same or different;

each $R^{3a}$ and $R^{3b}$ is independently H or $(C_1-C_3)$alkyl;

$Z^1$ is 6-12 membered aryl, 5-14 membered heteroaryl, or 3-14 membered heterocycle, wherein any 6-12 membered aryl, 5-14 membered heteroaryl, or 3-14 membered heterocycle of $Z^1$ is optionally substituted with 1, 2, 3, 4 or 5 $Z^{1a}$ or $Z^{1b}$, wherein the $Z^{1a}$ and $Z^{1b}$ groups are the same or different;

each $Z^{1a}$ is independently $(C_3-C_7)$carbocycle, 5-12 membered heteroaryl, 3-12 membered heterocycle, halogen, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, —$C(O)R^{n1}$, —$C(O)OR^{n1}$, —$C(O)NR^{q1}R^{r1}$ and —$S(O)_2NR^{n1}COR^{p1}$, wherein any $(C_3-C_7)$ carbocycle, 5-12 membered heteroaryl and 3-12 membered heterocycle of $Z^{1a}$ is optionally substituted with 1, 2, 3, 4 or 5 $Z^{1c}$ or $Z^{1d}$ groups, wherein the $Z^{1c}$ and $Z^{1d}$ groups are the same or different;

each $Z^{1b}$ is independently $(C_1-C_8)$alkyl optionally substituted with 1, 2, 3, 4 or 5 halogen, which are the same or different;

each $Z^{1c}$ is independently halogen, —CN, —OH, —$NH_2$, —$C(O)NR^{q2}R^{r2}$, or $(C_1-C_8)$heteroalkyl;

each $Z^{1d}$ is independently $(C_1-C_8)$alkyl or $(C_1-C_8)$haloalkyl;

each $R^{n1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{n1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{n1}$ is optionally substituted with 1, 2, 3, 4 or 5 $Z^{1c}$ groups, wherein the $Z^{1c}$ groups are the same or different;

each $R^{p1}$ is independently $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{p1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{p1}$ is optionally substituted with 1, 2, 3, 4 or 5 $Z^{1c}$ groups, wherein the $Z^{1c}$ groups are the same or different;

each $R^{q1}$ and $R^{r1}$ is independently H, $(C_1-C_8)$alkyl, $(C_3-C_7)$carbocycle, 3-7 membered heterocycle, or 5-6 membered monocyclic-heteroaryl, wherein any $(C_3-C_7)$carbocycle, 3-7 membered heterocycle, or 5-6 membered monocyclic-heteroaryl of $R^{q1}$ or $R^{r1}$ is optionally substituted with 1, 2, 3, 4 or 5 $Z^{1c}$ or $Z^{1d}$ groups, wherein the $Z^{1c}$ and $Z^{1d}$ groups are the same or different, and wherein any $(C_1-C_8)$alkyl of $R^{q1}$ or $R^{r1}$ is optionally substituted with 1, 2, 3, 4 or 5 $Z^{1c}$ groups, wherein the $Z^{1c}$ groups are the same or different, or $R^{q1}$ and $R^{r1}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups, wherein the $Z^{1c}$ and $Z^{1d}$ groups are the same or different;

each $R^{q2}$ and $R^{r2}$ is independently H, $(C_1-C_8)$alkyl, $(C_3-C_7)$carbocycle, or $R^{q2}$ and $R^{r2}$ together with the nitrogen to which they are attached form a 5, 6, or 7-membered heterocycle;

$Z^2$ is $(C_2-C_8)$alkenyl, $(C_2-C_8)$alkynyl, 6-12 membered aryl, 5-12 membered C-linked-heteroaryl, 3-12 membered C-linked-heterocycle, —$C(O)R^{n3}$, or —$C(O)NR^{q3}R^{r3}$, wherein any 6-12 membered aryl, 5-12 membered C-linked-heteroaryl, or 3-12 membered C-linked-heterocycle of $Z^2$ is optionally substituted with 1, 2, 3, 4 or 5 $Z^{2b}$ or $Z^{2c}$ groups, wherein the $Z^{2b}$ and $Z^{2c}$ groups are the same or different, and wherein any $(C_2-C_8)$alkenyl or $(C_2-C_8)$alkynyl of $Z^2$ is optionally substituted with 1, 2, 3, 4, or 5 $Z^{2c}$ groups, wherein the $Z^{2c}$ groups are the same or different;

each $R^{n3}$ is independently H or $(C_1-C_4)$alkyl;

each $R^{q3}$ and $R^{r3}$ is independently H or $(C_1-C_4)$alkyl;

each $Z^{2b}$ is independently oxo, $(C_1-C_4)$alkyl, $(C_1-C_4)$heteroalkyl or $(C_1-C_4)$haloalkyl;

each $Z^{2c}$ is independently oxo, halogen, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, —$NO_2$, —$C(O)R^{n4}$, —$C(O)OR^{n4}$, or —$C(O)NR^{q4}R^{r4}$;

each $R^{n4}$ is independently H, $(C_1-C_4)$alkyl, $(C_1-C_4)$haloalkyl, or $(C_1-C_4)$heteroalkyl;

each $R^{p4}$ is independently $(C_1-C_8)$alkyl, $(C_1-C_4)$haloalkyl, or $(C_1-C_4)$heteroalkyl;

each $R^{q4}$ and $R^{r4}$ is independently H, $(C_1-C_4)$alkyl, $(C_1-C_4)$haloalkyl, or $(C_1-C_4)$heteroalkyl;

each $Z^3$ is independently a $(C_1-C_4)$heteroalkyl;

each $Z^4$ is independently oxo, $(C_1-C_8)$alkyl, $(C_3-C_7)$carbocycle, halogen, —CN, —OR$^{n5}$, —NR$^{q5}$R$^{r5}$, —NR$^{n5}$COR$^{p5}$, —NR$^{n5}$CO$_2$R$^{p5}$, —C(O)R$^{n5}$, —C(O)OR$^{n5}$, or —C(O)NR$^{q5}$R$^{r5}$, wherein any $(C_3-C_7)$carbocycle or $(C_1-C_8)$alkyl of $Z^4$ is optionally substituted with 1, 2, 3, 4 or 5 $Z^{4a}$ groups, wherein the $Z^{4a}$ groups are the same or different;

each $Z^{4a}$ is independently halogen, —CN, or —OR$^{n6}$;

each R$^{n5}$, R$^{p5}$, R$^{q5}$, R$^{r5}$, and R$^{n6}$ is independently H or $(C_1-C_4)$alkyl;

each $Z^5$ is independently halogen, which may be same or different; and n is 0, 1, 2, or 3;

or a pharmaceutically acceptable salt thereof.

The above disclosures notwithstanding, there is a need for compounds that are potent and stable and exhibit improved pharmacokinetic and/or pharmacodynamic profiles for the treatment of a Retroviridae viral infection including an infection caused by the HIV virus.

Also of interest in the area of HIV therapies and treatments is extending the pharmacokinetic property of regimens provided to patients. While current regimens for treating HIV have progressed enough that patients no longer have to take multiple pills multiple times a day, patients today still are required to take a pill every day for the foreseeable span of their life. Thus, it would be beneficial to have HIV therapies that require patients take medication less than once a day (e.g. once every couple of days, once a week, once every other week, once a month, and so forth).

Provided herein are novel compounds exhibiting improved potency, improved metabolic stability, and improved pharmacokinetic and/or pharmacodynamic profiles.

SUMMARY

In some embodiments, the current disclosure relates to a compound of formula (Ia):

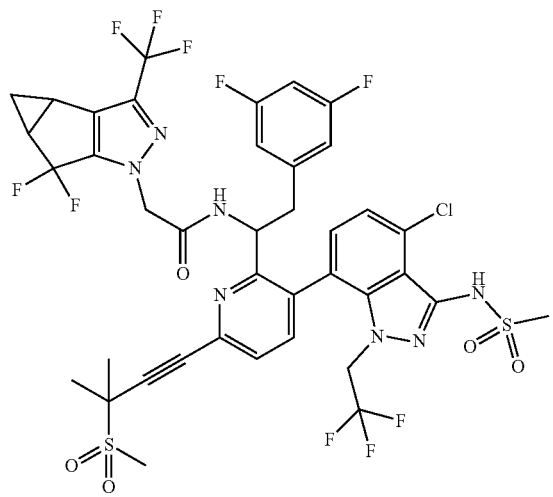

(Ia)

or a pharmaceutically acceptable salt thereof.

In some embodiments, the current disclosure relates to a compound of formula (Ib):

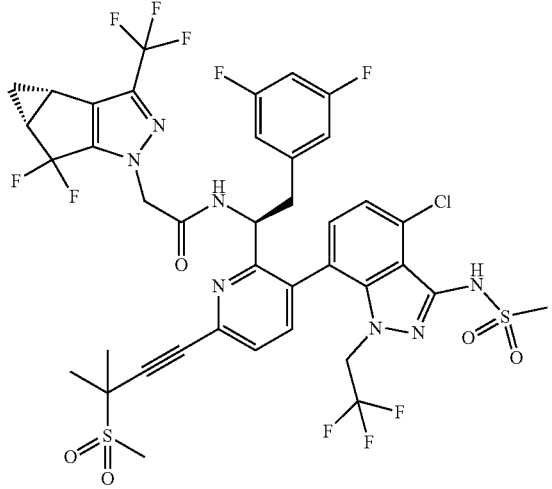

(Ib)

or a pharmaceutically acceptable salt thereof.

In some embodiments, the current disclosure relates to a compound of formula (IIa):

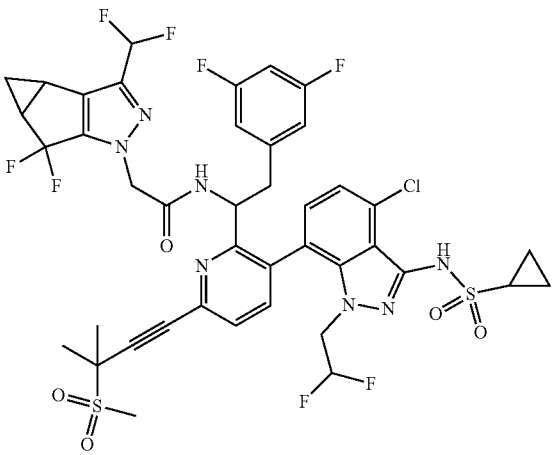

(IIa)

or a pharmaceutically acceptable salt thereof.

In some embodiments, the current disclosure relates to a compound of formula (IIb):

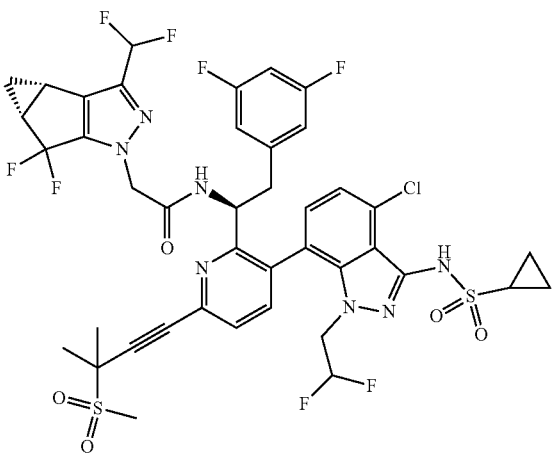

(IIb)

or a pharmaceutically acceptable salt thereof.

In one embodiment, the current disclosure relates to the use of a compound of formula (Ia) or (Ib), or a pharmaceutically acceptable salt thereof, in the treatment of a disease in a subject in need thereof.

In one embodiment, the current disclosure relates to the use of a compound of formula (Ia), (Ib), (IIa), and/or (IIb), or a pharmaceutically acceptable salt thereof, in the treatment of a disease in a subject in need thereof.

In certain embodiments, the current disclosure relates to a pharmaceutical composition comprising a compound of formula (Ia) or (Ib), or a pharmaceutically acceptable salt thereof, and a pharmaceutically acceptable excipient. In certain embodiments, the pharmaceutical composition is an injectable form. In certain embodiments, the pharmaceutical composition is suitable for oral administration.

In some embodiments, the current disclosure relates to a pharmaceutical composition comprising a compound of formula (Ia), (Ib), (IIa), and/or (IIb), or a pharmaceutically acceptable salt thereof, and a pharmaceutically acceptable excipient. In certain embodiments, the pharmaceutical composition is a parenteral (e.g., injectable) form. In certain embodiments, the pharmaceutical composition is suitable for oral administration.

In certain embodiments, the current disclosure relates to an article of manufacture comprising a unit dosage of a compound of formula (Ia) or (Ib), or a pharmaceutically acceptable salt thereof.

In some embodiments, the current disclosure relates to an article of manufacture comprising a unit dosage of a compound of formula (Ia), (Ib), (IIa), and/or (IIb), or a pharmaceutically acceptable salt thereof.

In certain embodiments, the current disclosure relates to a method for treating or preventing an HIV infection in a subject in need thereof, comprising administering to the subject a compound of formula (Ia) or (Ib), or a pharmaceutically acceptable salt thereof.

In some embodiments, the current disclosure relates to a method for treating or preventing an HIV infection in a subject in need thereof, comprising administering to the subject a compound of formula (Ia), (Ib), (IIa), and/or (IIb), or a pharmaceutically acceptable salt thereof.

In certain embodiments, the current disclosure relates to a method for preventing an HIV infection in a subject, comprising administering to the subject a compound of formula (Ia) or (Ib), or a pharmaceutically acceptable salt thereof. In certain embodiments, the subject is at risk of contracting the HIV virus, such as a subject who has one or more risk factors known to be associated with contracting the HIV virus.

In certain embodiments, the current disclosure relates to a method for preventing an HIV infection in a subject, comprising administering to the subject a compound of formula (Ia), (Ib), (IIa), and/or (IIb), or a pharmaceutically acceptable salt thereof. In certain embodiments, the subject is at risk of contracting the HIV virus, such as a subject who has one or more risk factors known to be associated with contracting the HIV virus.

In certain embodiments, the current disclosure relates to a method for treating or preventing an HIV infection in a subject in need thereof, comprising administering to the subject a compound of formula (Ia) or (Ib), or a pharmaceutically acceptable salt thereof, in combination with a therapeutically effective amount of one or more additional therapeutic agents.

In certain embodiments, the current disclosure relates to a method for treating or preventing an HIV infection in a subject in need thereof, comprising administering to the subject a compound of formula (Ia), (Ib), (IIa), and/or (IIb), or a pharmaceutically acceptable salt thereof, in combination with a therapeutically effective amount of one or more additional therapeutic agents.

In certain embodiments, the current disclosure relates to a compound of formula (Ia) or (Ib), or a pharmaceutically acceptable salt thereof for use in medical therapy.

In certain embodiments, the current disclosure relates to a compound of formula (Ia), (Ib), (IIa), and/or (IIb), or a pharmaceutically acceptable salt thereof for use in medical therapy.

In certain embodiments, the current disclosure relates to a compound of formula (Ia) or (Ib), or a pharmaceutically acceptable salt thereof, for use in treating or preventing an HIV infection in a subject.

In certain embodiments, the current disclosure relates to a compound of formula (Ia), (Ib), (IIa), and/or (IIb), or a pharmaceutically acceptable salt thereof, for use in treating or preventing an HIV infection in a subject.

In certain embodiments, the current disclosure relates to the use of a compound of formula (Ia) or (Ib), or a pharmaceutically acceptable salt thereof, for the manufacture of a medicament for treating or preventing an HIV infection in a subject.

In certain embodiments, the current disclosure relates to the use of a compound of formula (Ia), (Ib), (IIa), and/or (IIb), or a pharmaceutically acceptable salt thereof, for the manufacture of a medicament for treating or preventing an HIV infection in a subject.

In another embodiment, the current disclosure relates to intermediates useful for the synthesis of the compound of formula (Ia) or (Ib).

In another embodiment, the current disclosure relates to intermediates useful for the synthesis of the compound of formula (Ia), (Ib), (IIa), and/or (IIb).

In some embodiments, the pharmaceutically acceptable salt of the compound of formula (Ia), (Ib), (IIa), and/or (IIb) is the sodium salt.

Additional embodiments of the current disclosure are disclosed herein.

DETAILED DESCRIPTION

Figure 1:
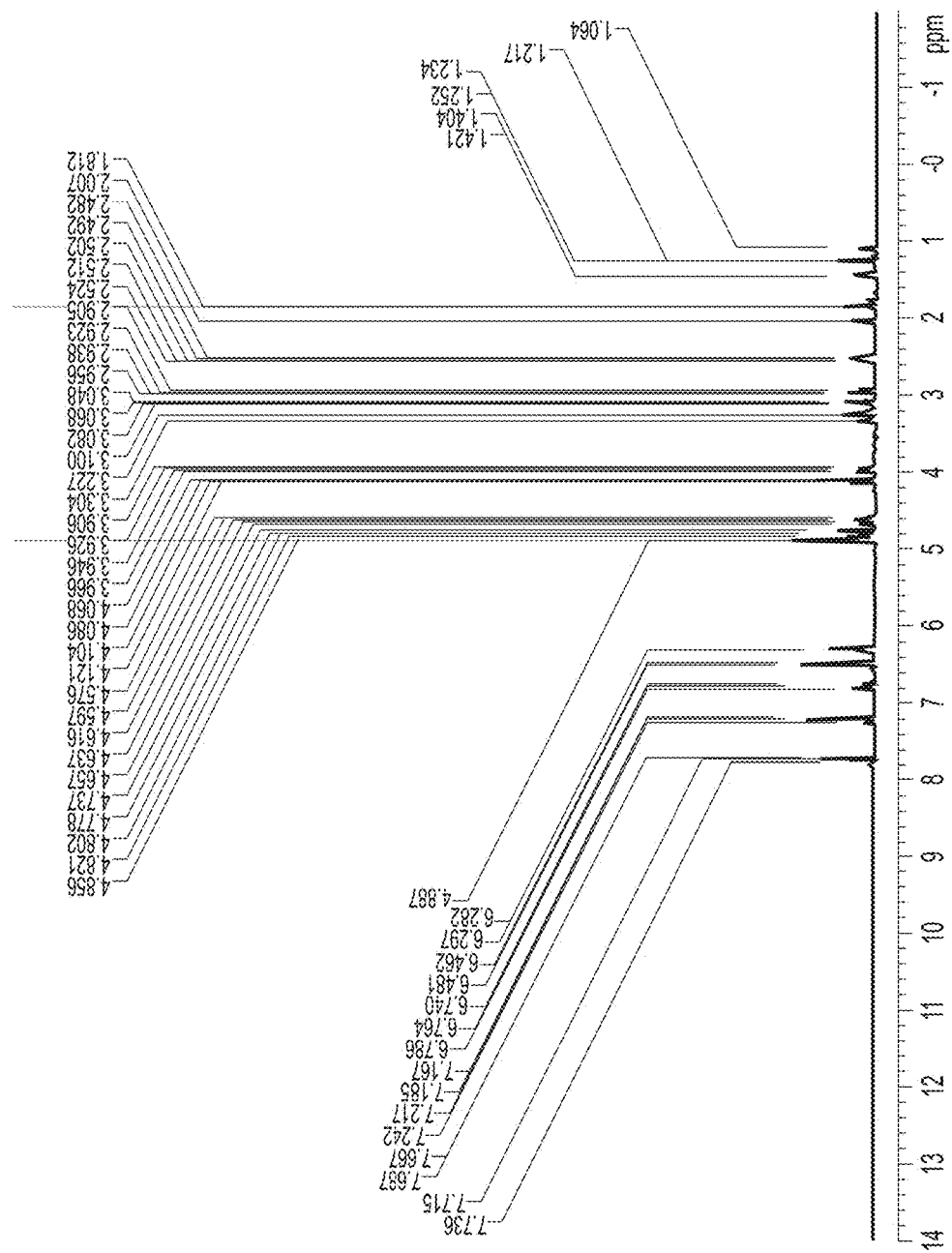
FIG. 1 shows $^1$H NMR of (400 MHz, Methanol-$d_4$) of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide.
Figure 2:
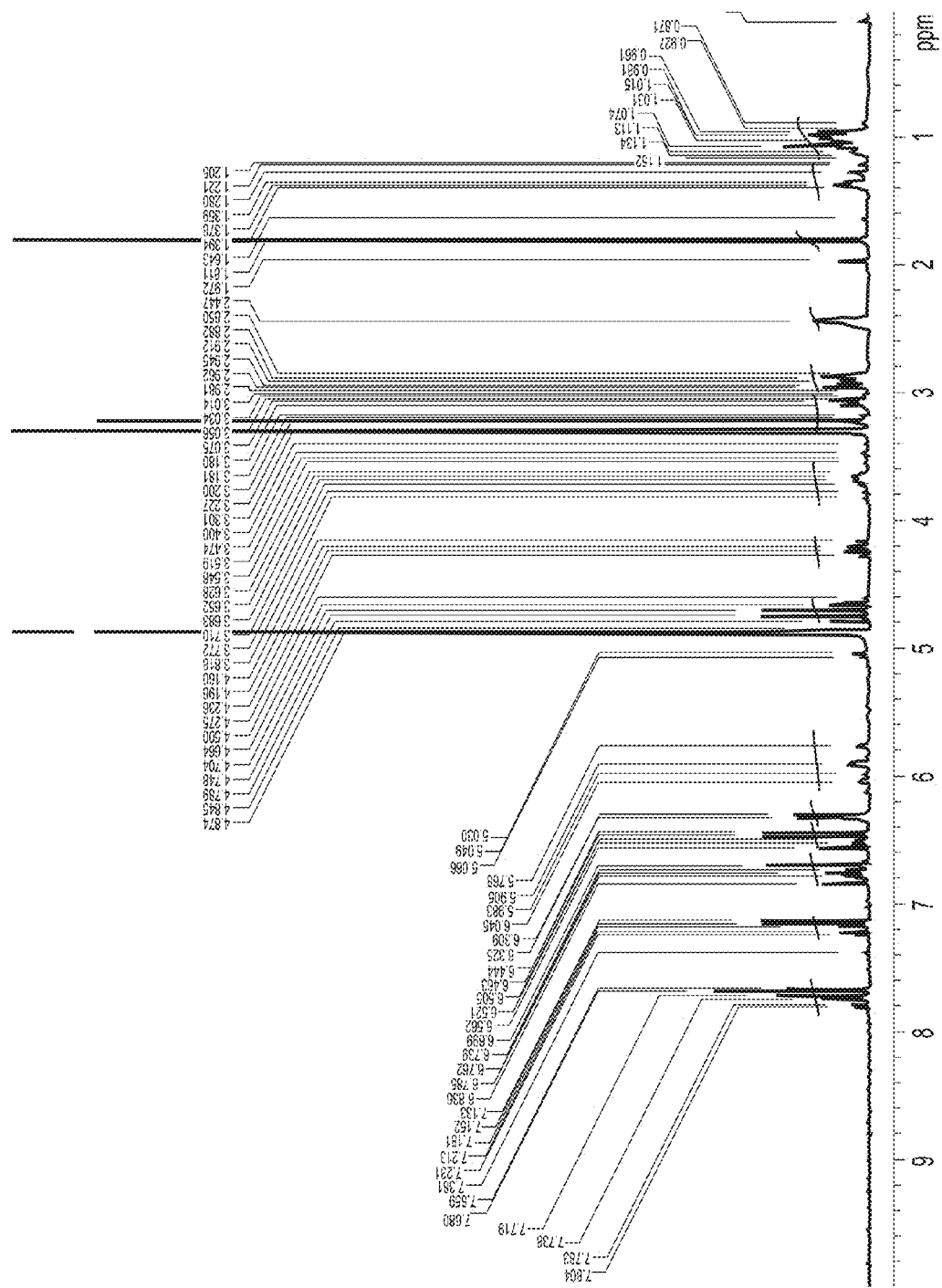
FIG. 2 shows $^1$H NMR of (400 MHz, Methanol-$d_4$) N—((S)-1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide.

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

As used herein, the term "$C_{max}$" refers to the maximum observed plasma/serum concentration of drug.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion (e.g. a sodium or potassium), an alkaline earth ion (e.g. calcium or magnesium), or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's HIV[+] status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and/or hindered rotation about a bond axis and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, scalemic mixtures, diastereomeric mixtures, optically pure forms and intermediate mixtures. Optically active (R)- and (S)-isomers may be prepared using chiral synthons or chiral reagents, or resolved using conventional techniques.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing an amide (e.g., by structure or chemical name), it is understood that the corresponding imidic acid tautomer is included by this disclosure and described the same as if the amide were expressly recited either alone or together with the imidic acid. Where more than two tautomers may exist, the present disclosure includes all such tautomers even if only a single tautomeric form is depicted by chemical name and/or structure.

The present disclosure also provides for prodrugs of the compound of Formula (Ia) or (Ib). A "prodrug" is defined in the pharmaceutical field as a biologically inactive derivative of a drug that upon administration to the human body is converted to the biologically active parent drug according to some chemical or enzymatic pathway.

Additionally, in some embodiments, the present disclosure also provides for prodrugs of the compound of Formula (Ia), (Ib), (IIa), and/or (IIb).

It is understood by one skilled in the art that this disclosure also includes any compound disclosed herein (e.g. a compound of Formula (Ia) or (Ib)) that may be enriched at any or all atoms above naturally occurring isotopic ratios with one or more isotopes such as, but not limited to, deuterium ($^2$H or D).

Disclosed are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (Ia) or (Ib), can generally be prepared by conventional techniques known to those skilled in the art or by processes analogous to those described in the Examples as set out below using an appropriate isotopically-labeled reagent in place of the non-labeled reagent previously employed.

Additionally, in some embodiments, isotopically-labeled compounds of Formula (Ia), (Ib), (IIa), and/or (IIb), can generally be prepared by conventional techniques known to those skilled in the art or by processes analogous to those described in the Examples as set out below using an appropriate isotopically-labeled reagent in place of the non-labeled reagent previously employed.

Compounds described herein may have chiral centers and/or geometric isomeric centers (E- and Z-isomers), and it is to be understood that all such optical, enantiomeric, diastereoisomeric and geometric isomers are encompassed. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

Also provided are also pharmaceutically acceptable hydrates, solvates, tautomeric forms, polymorphs, and prodrugs of the compounds described herein.

In a preferred embodiment, the current disclosure relates to the use of the compound of formula (Ia) or (Ib) in treating a Retroviridae viral infection including an infection caused by the HIV virus comprising administering a therapeutically effective amount to a subject in need thereof.

In a preferred embodiment, the current disclosure relates to the use of the compound of formula (Ia), (Ib), (IIa), and/or (IIb) in treating a Retroviridae viral infection including an infection caused by the HIV virus comprising administering a therapeutically effective amount to a subject in need thereof.

It is a desirable goal to discover a compound or a pharmaceutically acceptable salt thereof having a low $EC_{50}$. The $EC_{50}$ value refers to the concentration of a compound in an assay that achieves 50% of the maximum efficacy. A compound with a lower $EC_{50}$ achieves similar efficacy with lower compound concentration relative to a compound with a higher $EC_{50}$. Thus, a lower $EC_{50}$ is generally preferred for drug development.

It is a desirable goal to discover a compound or a pharmaceutically acceptable salt thereof that has good physical and/or chemical stability. An increase in overall stability of a compound can provide an increase in circulation time in the body. With less degradation, a stable compound can be administered in lower doses and still maintain efficacy. Also, with less degradation, there is less concern about by-products from degradation of a compound.

It is a desirable goal to discover a compound or a pharmaceutically acceptable salt thereof that has improved pharmacokinetic and/or pharmacodynamic profiles and long half-life. It is advantageous for a drug to have a moderate or low clearance and a long half-life, as this can lead to a good bioavailability and high exposure in systemic exposure. Reducing the clearance and increasing half-life time of a compound could reduce the daily dose required for efficacy and therefore give a better efficacy and safety profile. Thus, improved pharmacokinetic and/or pharmacodynamic profiles and long half-life can provide for better patient compliance.

It is a desirable goal to discover a compound or a pharmaceutically acceptable salt thereof that has good pharmacokinetic profile from a slow release injectable formulation. It is advantageous for a drug to have a low $EC_{50}$ and long acting pharmacokinetics, as this can lead to low frequency of administration. Reducing the frequency of administration can provide for better patient compliance. Reducing the frequency of administration can be desirable for patients with difficult or limited access to health care.

Advantageously, discovered is a compound of formula (Ia) and (Ib) herein that provides advantages compared to structurally close compounds (herein designated as compounds A and B) disclosed in U.S. Patent Publication Nos. 2014/0296266A1 and 2014/0303164A1:

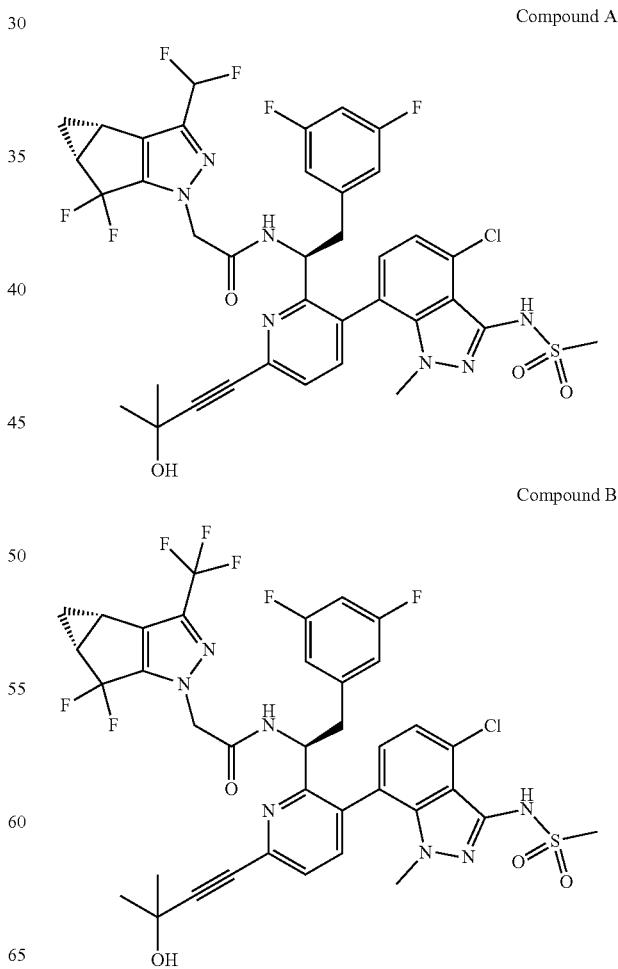

Compound A

Compound B

Therefore, the present disclosure includes but is not limited to the provision of a compound of formula (Ia)

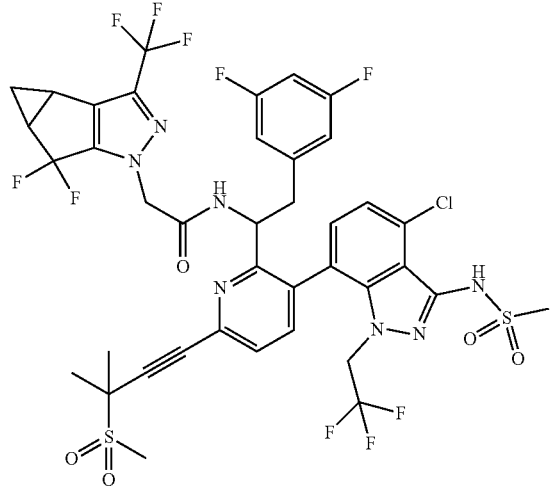

(Ia)

or pharmaceutically acceptable salt thereof, and methods of using the compound of formula (Ia) for the treatment of a Retroviridae viral infection including an infection caused by the HIV virus.

Therefore, the present disclosure includes but is not limited to the provision of a compound of formula (Ib)

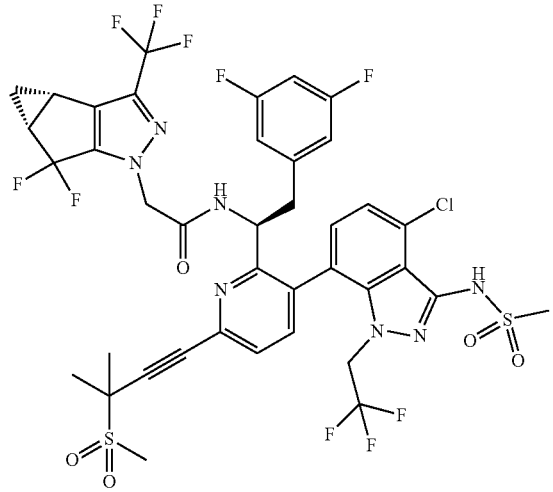

(Ib)

or pharmaceutically acceptable salt thereof, and methods of using the compound of formula (Ib) for the treatment of a Retroviridae viral infection including an infection caused by the HIV virus.

Also disclosed herein is a compound of formula (IIa) and (IIb), which provides advantages compared to Compounds A and B (shown above).

Therefore, the present disclosure includes but is not limited to the provision of a compound of formula (IIa)

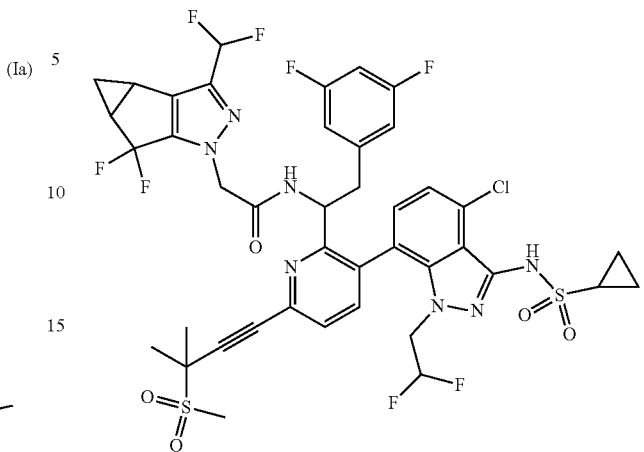

(IIa)

or pharmaceutically acceptable salt thereof, and methods of using the compound of formula (IIa) for the treatment of a Retroviridae viral infection including an infection caused by the HIV virus.

Therefore, the present disclosure includes but is not limited to the provision of a compound of formula (IIb)

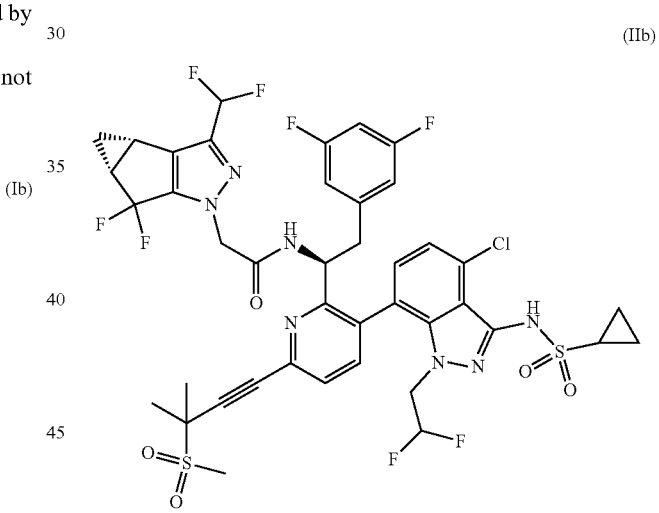

(IIb)

or pharmaceutically acceptable salt thereof, and methods of using the compound of formula (IIb) for the treatment of a Retroviridae viral infection including an infection caused by the HIV virus.

In some embodiments, the compounds disclosed herein (e.g., a compound of formula (Ia), (Ib), (IIa), and/or (IIb), or pharmaceutically acceptable salt thereof) are used for preventing an HIV infection in a subject. In some embodiments, the compounds disclosed herein are used for preventing an HIV infection in a subject at risk for infection. In some embodiments, the compounds disclosed herein are used for pre-exposure prophylaxis (PrEP) to reduce the risk of sexually acquired HIV-1.

It is believed that the compounds disclosed herein (e.g., a compound of formula (Ia), (Ib), (IIa), and/or (IIb), or a pharmaceutically acceptable salt thereof) are active against major HIV-1 mutants selected by clinical Protease Inhibitors (PIs), nucleoside reverse transcriptase inhibitors (NRTIs), Non-Nucleoside Reverse Transcriptase Inhibitors (NNRTIs), and Integrase inhibitors (INSTIs).

Combination Therapy

In certain embodiments, a method for treating or preventing an HIV infection in a human having or at risk of having the infection is provided, comprising administering to the human a therapeutically effective amount of a compound disclosed herein (e.g., a compound of formula (Ia) or (Ib)), or a pharmaceutically acceptable salt thereof, in combination with a therapeutically effective amount of one or more (e.g., one, two, three, or four; or one or two; or one to three; or one to four) additional therapeutic agents. In one embodiment, a method for treating an HIV infection in a human having or at risk of having the infection is provided, comprising administering to the human a therapeutically effective amount of a compound disclosed herein (e.g. a compound of Formula (Ia) or (Ib)), or a pharmaceutically acceptable salt thereof, in combination with a therapeutically effective amount of one or more (e.g., one, two, three, or four; or one or two; or one to three; or one to four) additional therapeutic agents.

In some embodiments, a method for treating or preventing an HIV infection in a human having or at risk of having the infection is provided, comprising administering to the human a therapeutically effective amount of a compound disclosed herein (e.g., a compound of formula (Ia), (Ib), (IIa), and/or (IIb)), or a pharmaceutically acceptable salt thereof, in combination with a therapeutically effective amount of one or more (e.g., one, two, three, or four; or one or two; or one to three; or one to four) additional therapeutic agents. In one embodiment, a method for treating an HIV infection in a human having or at risk of having the infection is provided, comprising administering to the human a therapeutically effective amount of a compound disclosed herein (e.g., a compound of formula (Ia), (Ib), (IIa), and/or (IIb)), or a pharmaceutically acceptable salt thereof, in combination with a therapeutically effective amount of one or more (e.g., one, two, three, or four; or one or two; or one to three; or one to four) additional therapeutic agents.

In one embodiment, pharmaceutical compositions comprising a compound disclosed herein (e.g. a compound of Formula (Ia) or (Ib)), or a pharmaceutically acceptable salt thereof, in combination with one or more (e.g., one, two, three, or four; or one or two; or one to three; or one to four) additional therapeutic agents, and a pharmaceutically acceptable excipient are provided.

In some embodiments, pharmaceutical compositions comprising a compound disclosed herein (e.g. a compound of Formula (Ia), (Ib), (IIa), and/or (IIb)), or a pharmaceutically acceptable salt thereof, in combination with one or more (e.g., one, two, three, or four; or one or two; or one to three; or one to four) additional therapeutic agents, and a pharmaceutically acceptable excipient are provided.

In certain embodiments, the present disclosure provides a method for treating an HIV infection, comprising administering to a subject in need thereof a therapeutically effective amount of a compound disclosed herein (e.g. a compound of Formula (Ia) or (Ib)), or a pharmaceutically acceptable salt thereof, in combination with a therapeutically effective amount of one or more additional therapeutic agents which are suitable for treating an HIV infection.

In certain embodiments, the present disclosure provides a method for treating an HIV infection, comprising administering to a subject in need thereof a therapeutically effective amount of a compound disclosed herein (e.g., a compound of Formula (Ia), (Ib), (IIa), and/or (IIb)), or a pharmaceutically acceptable salt thereof, in combination with a therapeutically effective amount of one or more additional therapeutic agents which are suitable for treating an HIV infection.

In certain embodiments, the present disclosure provides a method for treating an HIV infection, comprising administering to a subject in need thereof a therapeutically effective amount of a compound disclosed herein (e.g., a compound of Formula (Ia), (Ib), (IIa), and/or (IIb)), or a pharmaceutically acceptable salt thereof.

In certain embodiments, a compound disclosed herein (e.g. a compound of Formula (Ia) or (Ib)), or a pharmaceutically acceptable salt thereof, is combined with one, two, three, four, or more additional therapeutic agents. In certain embodiments, a compound disclosed herein (e.g. a compound of Formula (Ia) or (Ib)), or a pharmaceutically acceptable salt thereof, is combined with one additional therapeutic agent. In certain embodiments, a compound disclosed herein (e.g. a compound of Formula (Ia) or (Ib)), or a pharmaceutically acceptable salt thereof, is combined with two additional therapeutic agents. In other embodiments, a compound disclosed herein (e.g. a compound of Formula (Ia) or (Ib)), or a pharmaceutically acceptable salt thereof, is combined with three additional therapeutic agents. In further embodiments, a compound disclosed herein (e.g. a compound of Formula (Ia) or (Ib)), or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

In some embodiments, a compound disclosed herein (e.g. a compound of Formula (Ia), (Ib), (IIa), and/or (IIb)), or a pharmaceutically acceptable salt thereof, is combined with one, two, three, four, or more additional therapeutic agents. In certain embodiments, a compound disclosed herein (e.g. a compound of Formula (Ia), (Ib), (IIa), and/or (IIb)), or a pharmaceutically acceptable salt thereof, is combined with one additional therapeutic agent. In certain embodiments, a compound disclosed herein (e.g. a compound of Formula (Ia), (Ib), (IIa), and/or (IIb)), or a pharmaceutically acceptable salt thereof, is combined with two additional therapeutic agents. In other embodiments, a compound disclosed herein (e.g. a compound of Formula (Ia), (Ib), (IIa), and/or (IIb)), or a pharmaceutically acceptable salt thereof, is combined with three additional therapeutic agents. In further embodiments, a compound disclosed herein (e.g. a compound of Formula (Ia), (Ib), (IIa), and/or (IIb)), or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein (e.g., a compound of formula (Ia) or (Ib)), or a pharmaceutically acceptable salt thereof, is administered with one or more additional therapeutic agents. Co-administration of a compound disclosed herein (e.g. a compound of Formula (Ia) or (Ib)), or a pharmaceutically acceptable salt thereof, with one or more additional therapeutic agents generally refers to simultaneous or sequential administration of a compound disclosed herein (e.g. a compound of Formula (Ia) or (Ib)) and one or more additional therapeutic agents, such that therapeutically effective amounts of the compound disclosed herein (e.g. a compound of Formula (Ia) or (Ib)), or a pharmaceutically acceptable salt thereof, and the one or more additional therapeutic agents are both present in the body of the subject. When administered sequentially, the combination may be administered in two or more administrations.

In some embodiments, a compound disclosed herein (e.g., a compound of formula (Ia), (Ib), (IIa), and/or (IIb)), or a pharmaceutically acceptable salt thereof, is administered with one or more additional therapeutic agents. Co-administration of a compound disclosed herein (e.g. a compound of Formula (Ia), (Ib), (IIa), and/or (IIb)), or a pharmaceutically acceptable salt thereof, with one or more additional therapeutic agents generally refers to simultaneous or sequential administration of a compound disclosed herein (e.g. a compound of Formula (Ia), (Ib), (IIa), and/or (IIb)) and one or more additional therapeutic agents, such that therapeutically effective amounts of the compound disclosed herein (e.g. a compound of Formula (Ia), (Ib), (IIa), and/or (IIb)), or a pharmaceutically acceptable salt thereof, and the one or more additional therapeutic agents are both present in the body of the subject. When administered sequentially, the combination may be administered in two or more administrations.

Co-administration includes administration of unit dosages of the compounds disclosed herein (e.g. a compound of Formula (Ia) or (Ib)), or pharmaceutically acceptable salts thereof, before or after administration of unit dosages of one or more additional therapeutic agents. For example, the compound disclosed herein (e.g. a compound of Formula (Ia) or (Ib)), or a pharmaceutically acceptable salt thereof, may be administered within seconds, minutes, or hours of the administration of the one or more additional therapeutic agents. In some embodiments, a unit dose of a compound disclosed herein (e.g., a compound of formula (Ia) or (Ib)), or a pharmaceutically acceptable salt thereof, is administered first, followed within seconds or minutes by administration of a unit dose of one or more additional therapeutic agents. Alternatively, a unit dose of one or more additional therapeutic agents is administered first, followed by administration of a unit dose of a compound disclosed herein (e.g. a compound of Formula (Ia) or (Ib)) within seconds or minutes. In other embodiments, a unit dose of a compound disclosed herein (e.g. a compound of Formula (Ia) or (Ib)) is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein (e.g. a compound of Formula (Ia) or (Ib)).

In some embodiments, co-administration includes administration of unit dosages of the compounds disclosed herein (e.g. a compound of Formula (Ia), (Ib), (IIa), and/or (IIb)), or pharmaceutically acceptable salts thereof, before or after administration of unit dosages of one or more additional therapeutic agents. For example, the compound disclosed herein (e.g. a compound of Formula (Ia), (Ib), (IIa), and/or (IIb)), or a pharmaceutically acceptable salt thereof, may be administered within seconds, minutes, or hours of the administration of the one or more additional therapeutic agents. In some embodiments, a unit dose of a compound disclosed herein (e.g., a compound of formula (Ia), (Ib), (IIa), and/or (IIb)), or a pharmaceutically acceptable salt thereof, is administered first, followed within seconds or minutes by administration of a unit dose of one or more additional therapeutic agents. Alternatively, a unit dose of one or more additional therapeutic agents is administered first, followed by administration of a unit dose of a compound disclosed herein (e.g. a compound of Formula (Ia), (Ib), (IIa), and/or (IIb)) within seconds or minutes. In other embodiments, a unit dose of a compound disclosed herein (e.g. a compound of Formula (Ia), (Ib), (IIa), and/or (IIb)) is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein (e.g. a compound of Formula (Ia), (Ib), (IIa), and/or (IIb)).

For the avoidance of doubt, co-administration of a compound disclosed herein (e.g. a compound of Formula (Ia), (Ib), (IIa), and/or (IIb)), or a pharmaceutically acceptable salt thereof, with one or more additional therapeutic agents, may refer to co-administration with one or more of the thereapeutic agents described herein.

In certain embodiments, a compound disclosed herein (e.g. a compound of Formula (Ia) or (Ib)), or a pharmaceutically acceptable salt thereof, is combined with one or more additional therapeutic agents in a unitary dosage form for simultaneous administration to a subject. In certain embodiments, such a unitary dosage form can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the unitary dosage form can be dosed intravenous, subcutaneous, or intramuscular. In certain embodiments, the unitary dosage form is orally bioavailable and can be dosed orally. In certain embodiments, the unitary dosage form can be a solid dosage form for oral administration.

In some embodiments, a compound disclosed herein (e.g. a compound of Formula (Ia), (Ib), (IIa), and/or (IIb)), or a pharmaceutically acceptable salt thereof, is combined with one or more additional therapeutic agents in a unitary dosage form for simultaneous administration to a subject. In certain embodiments, such a unitary dosage form can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the unitary dosage form can be dosed intravenous, subcutaneous, or intramuscular. In certain embodiments, the unitary dosage form is orally bioavailable and can be dosed orally. In certain embodiments, the unitary dosage form can be a solid dosage form for oral administration.

The compound disclosed herein (e.g. a compound of Formula (Ia) or (Ib), or a pharmaceutically acceptable salt thereof), in combination with one or more additional therapeutic agents can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

The compound disclosed herein (e.g. a compound of Formula (Ia), (Ib), (IIa), and/or (IIb), or a pharmaceutically acceptable salt thereof), in combination with one or more additional therapeutic agents can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

In certain embodiments, a compound of Formula (Ia) or (Ib), or a pharmaceutically acceptable salt thereof, is formulated as a tablet, which may optionally contain one or more other compounds useful for treating HIV. In certain embodiments, the tablet can one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, a compound of Formula (Ia), (Ib), (IIa), and/or (IIb), or a pharmaceutically acceptable salt thereof, is formulated as a tablet, which may optionally contain one or more other compounds useful for treating HIV. In certain embodiments, the tablet can one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, a compound of Formula (Ia), (Ib), (IIa), and/or (IIb), or a pharmaceutically acceptable salt thereof, is formulated as a solution formulation, which may optionally contain one or more other compounds useful for treating HIV. In certain embodiments, the tablet can one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, a compound of Formula (Ia), (Ib), (IIa), and/or (IIb), or a pharmaceutically acceptable salt thereof, is formulated as a suspension, which may optionally contain one or more other compounds useful for treating HIV. In certain embodiments, the tablet can one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent may be an anti-HIV agent selected from the group consisting of combination drugs for treating HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine;

ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; cabotegravir and rilpivirine; cabotegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine; lamivudine+abacavir+zidovudine; lamivudine+abacavir; lamivudine+tenofovir disoproxil fumarate; lamivudine+zidovudine+nevirapine; lopinavir+ritonavir; lopinavir+ritonavir+abacavir+lamivudine; lopinavir+ritonavir+zidovudine+lamivudine; tenofovir+lamivudine; and tenofovir disoproxil fumarate+emtricitabine+rilpivirine hydrochloride; lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500. Further examples of non-nucleoside reverse transcriptase inhibitors are disclosed in U.S. Patent Publication No. US2016/0250215.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

In some embodiments, examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, KP-1461, and 4'-ethynyl-2-fluoro-2'-deoxyadenosine (EFdA).

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series;

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523, VRC-HIVMAB080-00-AB, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006738 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine.

HIV Combination Therapy

In a particular embodiment, a compound disclosed herein (e.g. a compound of Formula (Ia) or (Ib)), or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir;

fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, a compound disclosed herein (e.g. a compound of Formula (Ia), (Ib), (IIa), and/or (IIb)), or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; abacavir sulfate; 4'-ethynyl-2-fluoro-2'-deoxyadenosine (EFdA); and Bictegravir, or a pharmaceutically acceptable salt thereof.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein (e.g. a compound of Formula (Ia) or (Ib)), or a pharmaceutically acceptable salt thereof, is combined with one or two HIV nucleoside or nucleotide inhibitors of reverse transcriptase. In a specific embodiment, a compound disclosed herein (e.g. a compound of Formula (Ia) or (Ib)), or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein (e.g. a compound of Formula (Ia) or (Ib)), or a pharmaceutically acceptable salt thereof, is combined with an HIV nucleoside or nucleotide inhibitor of reverse transcriptase, and an HIV protease inhibiting compound. In an additional embodiment, a compound disclosed herein (e.g. a compound of Formula (Ia) or (Ib)), or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein (e.g. a compound of Formula (Ia) or (Ib)), or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein (e.g. a compound of Formula (Ia) or (Ib)), or a pharmaceutically acceptable salt thereof, is combined with two HIV nucleoside or nucleotide inhibitors of reverse transcriptase.

In some embodiments, a compound disclosed herein (e.g. a compound of Formula (Ia), (Ib), (IIa), and/or (IIb)), or a pharmaceutically acceptable salt thereof, is combined with one or two HIV nucleoside or nucleotide inhibitors of reverse transcriptase. In a specific embodiment, a compound disclosed herein (e.g. a compound of Formula (Ia), (Ib), (IIa), and/or (IIb)), or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein (e.g. a compound of Formula (Ia), (Ib), (IIa), and/or (IIb)), or a pharmaceutically acceptable salt thereof, is combined with an HIV nucleoside or nucleotide inhibitor of reverse transcriptase, and an HIV protease inhibiting compound. In an additional embodiment, a compound disclosed herein (e.g. a compound of Formula (Ia), (Ib), (IIa), and/or (IIb)), or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein (e.g. a compound of Formula (Ia), (Ib), (IIa), and/or (IIb)), or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein (e.g. a compound of Formula (Ia), (Ib), (IIa), and/or (IIb)), or a pharmaceutically acceptable salt thereof, is combined with two HIV nucleoside or nucleotide inhibitors of reverse transcriptase.

In a particular embodiment, a compound disclosed herein (e.g. a compound of Formula (Ia) or (Ib)), or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide fumarate or tenofovir alafenamide hemifumarate.

In some embodiments, a compound disclosed herein (e.g. a compound of Formula (Ia), (Ib), (IIa), and/or (IIb)), or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide fumarate, tenofovir alafenamide hemifumarate, bictegravir (or a pharmaceutically acceptable salt thereof), or 4'-ethynyl-2-fluoro-2'-deoxyadenosine (EFdA).

In some embodiments, a compound disclosed herein (e.g. a compound of Formula (Ia), (Ib), (IIa), and/or (IIb)), or a pharmaceutically acceptable salt thereof, is combined with a HIV integrase inhibitor.

In a particular embodiment, a compound disclosed herein (e.g. a compound of Formula (Ia) or (Ib)), or a pharmaceutically acceptable salt thereof, is combined with tenofovir, tenofovir disoproxil, tenofovir disoproxil fumarate, tenofovir alafenamide, tenofovir alafenamide fumarate or tenofovir alafenamide hemifumarate.

In some embodiments, a compound disclosed herein (e.g. a compound of Formula (Ia), (Ib), (IIa), and/or (IIb)), or a pharmaceutically acceptable salt thereof, is combined with tenofovir, tenofovir disoproxil, tenofovir disoproxil fumarate, tenofovir alafenamide, tenofovir alafenamide fumarate, tenofovir alafenamide hemifumarate, bictegravir (or a pharmaceutically acceptable salt thereof), or 4'-ethynyl-2-fluoro-2'-deoxyadenosine (EFdA).

In a particular embodiment, a compound disclosed herein (e.g. a compound of Formula (Ia) or (Ib)), or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide fumarate and tenofovir alafenamide hemifumarate, and a second additional therapeutic agent selected from the group consisting of emtricitabine and lamivudine.

In some embodiments, a compound disclosed herein (e.g. a compound of Formula (Ia), (Ib), (IIa), and/or (IIb)), or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide fumarate and tenofovir alafenamide hemifumarate, and a second additional therapeutic agent selected from the group consisting of emtricitabine and lamivudine.

In a particular embodiment, a compound disclosed herein (e.g. a compound of Formula (Ia) or (Ib)), or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine. In a particular embodiment, a compound of formula (Ia) or (Ib), or a pharmaceutically acceptable salt thereof, is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine. In a particular embodiment, a compound of formula (Ia) or (Ib), or a pharmaceutically acceptable salt thereof, is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine. In some embodiments, the compound of formula (Ia) or (Ib), or a pharmaceutically acceptable salt thereof, and the first and second additional therapeutic agents as disclosed above are administered simultaneously. Optionally, the compound of formula (Ia) or (Ib), or a pharmaceutically acceptable salt thereof, and the first and second additional therapeutic agents as disclosed above are combined in a unitary dosage form for simultaneous administration to a subject. In other embodiments, the compound of formula (Ia) or (Ib), or a pharmaceutically acceptable salt thereof, and the first and second additional therapeutic agents as disclosed above are administered sequentially.

In some embodiments, a compound disclosed herein (e.g. a compound of Formula (Ia), (Ib), (IIa), and/or (IIb)), or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine. In a particular embodiment, a compound of formula (Ia), (Ib), (IIa), and/or (IIb), or a pharmaceutically acceptable salt thereof, is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine. In a particular embodiment, a compound of formula (Ia), (Ib), (IIa), and/or (IIb), or a pharmaceutically acceptable salt thereof, is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine. In some embodiments, the compound of formula (Ia), (Ib), (IIa), and/or (IIb), or a pharmaceutically acceptable salt thereof, and the first and second additional therapeutic agents as disclosed above are administered simultaneously. Optionally, the compound of formula (Ia), (Ib), (IIa), and/or (IIb), or a pharmaceutically acceptable salt thereof, and the first and second additional therapeutic agents as disclosed above are combined in a unitary dosage form for simultaneous administration to a subject. In other embodiments, the compound of formula (Ia), (Ib), (IIa), and/or (IIb), or a pharmaceutically acceptable salt thereof, and the first and second additional therapeutic agents as disclosed above are administered sequentially.

In some embodiments, a compound disclosed herein (e.g. a compound of Formula (Ia), (Ib), (IIa), and/or (IIb)), or a pharmaceutically acceptable salt thereof, is combined with bictegravir or a pharmaceutically acceptable salt thereof.

A compound as disclosed herein (e.g., any compound of formula (Ia) or (Ib)) may be combined with one or more additional therapeutic agents in any dosage amount of the compound of formula (Ia) or (Ib) (e.g., from 1 mg to 1000 mg of compound).

In some embodiments, a compound as disclosed herein (e.g., any compound of Formula (Ia), (Ib), (IIa), and/or (IIb), or a pharmaceutically acceptable salt thereof) may be combined with one or more additional therapeutic agents in any dosage amount of the compound of Formula (Ia), (Ib), (IIa), and/or (IIb) (e.g., from 1 mg to 1000 mg of compound).

In certain embodiments, a compound disclosed herein (e.g. a compound of Formula (Ia) or (Ib)), or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein (e.g. a compound of Formula (Ia) or (Ib)), or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein (e.g. a compound of Formula (Ia) or (Ib)), or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of Formula (Ia) or (Ib)) may be combined with the agents provided herein in any dosage amount of the compound (e.g., from 1 mg to 1000 mg of compound) the same as if each combination of dosages were specifically and individually listed.

In some embodiments, a compound disclosed herein (e.g. a compound of Formula (Ia), (Ib), (IIa), and/or (IIb)), or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein (e.g. a compound of Formula (Ia), (Ib), (IIa), and/or (IIb)), or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein (e.g. a compound of Formula (Ia), (Ib), (IIa), and/or (IIb)), or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of Formula (Ia), (Ib), (IIa), and/or (IIb)) may be combined with the agents provided herein in any dosage amount of the compound (e.g., from 1 mg to 1000 mg of compound) the same as if each combination of dosages were specifically and individually listed.

In certain embodiments, a compound disclosed herein (e.g. a compound of Formula (Ia) or (Ib)), or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein (e.g. a compound of Formula (Ia) or (Ib)), or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein (e.g. a compound of Formula (Ia) or (Ib)), or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of Formula (Ia) or (Ib)) may be combined with the agents provided herein in any dosage amount of the compound (e.g., from 1 mg to 1000 mg of compound) the same as if each combination of dosages were specifically and individually listed.

In some embodiments, a compound disclosed herein (e.g. a compound of Formula (Ia), (Ib), (IIa), and/or (IIb)), or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein (e.g. a compound of Formula (Ia), (Ib), (IIa), and/or (IIb)), or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein (e.g. a compound of Formula (Ia), (Ib), (IIa), and/or (IIb)), or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of Formula (Ia), (Ib), (IIa), and/or (IIb)) may be combined with the agents provided herein in any dosage amount of the compound (e.g., from 1 mg to 1000 mg of compound) the same as if each combination of dosages were specifically and individually listed.

In some embodiments, a compound disclosed herein (e.g. a compound of Formula (Ia), (Ib), (IIa), and/or (IIb)), or a pharmaceutically acceptable salt thereof, is combined with 20-80 mg of bictegravir or a pharmaceutically acceptable salt thereof. A compound as disclosed herein (e.g., a compound of Formula (Ia), (Ib), (IIa), and/or (IIb), or a pharmaceutically acceptable salt thereof) may be combined with the agents provided herein in any dosage amount of the compound (e.g., from 1 mg to 1000 mg of compound) the same as if each combination of dosages were specifically and individually listed.

In one embodiment, kits comprising a compound disclosed herein (e.g., a compound of formula (Ia) or (Ib)), or a pharmaceutically acceptable salt thereof, in combination with one or more (e.g., one, two, three, one or two, or one to three) additional therapeutic agents are provided.

In some embodiments, kits comprising a compound disclosed herein (e.g., a compound of Formula (Ia), (Ib), (IIa), and/or (IIb)), or a pharmaceutically acceptable salt thereof, in combination with one or more (e.g., one, two, three, one or two, or one to three) additional therapeutic agents are provided.

Pharmaceutical Compositions

Pharmaceutical compositions disclosed herein comprise a compound disclosed herein (e.g., a compound of formula (Ia) or (Ib)), or a pharmaceutically acceptable salt thereof, together with one or more pharmaceutically acceptable excipients and optionally other therapeutic agents. Pharmaceutical compositions containing the active ingredient may be in any form suitable for the intended method of administration.

In some embodiments, pharmaceutical compositions disclosed herein comprise a compound disclosed herein (e.g., a compound of Formula (Ia), (Ib), (IIa), and/or (IIb)), or a pharmaceutically acceptable salt thereof, together with one or more pharmaceutically acceptable excipients and optionally other therapeutic agents. Pharmaceutical compositions containing the active ingredient may be in any form suitable for the intended method of administration.

Pharmaceutical compositions comprising the compound disclosed herein (e.g. a compound of Formula (Ia) or (Ib)), or a pharmaceutically acceptable salt thereof, may be prepared with conventional carriers (e.g., inactive ingredient or excipient material) which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 5$^{th}$ edition, American Pharmacists Association, 1986. Excipients can include ascorbic acid and other antioxidants, chelating agents such as EDTA, carbohydrates such as dextrin, hydroxyalkylcellulose, hydroxyalkylmethylcellulose, stearic acid and the like.

In some embodiments, pharmaceutical compositions comprising the compound disclosed herein (e.g. a compound of Formula (Ia), (Ib), (IIa), and/or (IIb)), or a pharmaceutically acceptable salt thereof, may be prepared with conventional carriers (e.g., inactive ingredient or excipient material) which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, $5^{th}$ edition, American Pharmacists Association, 1986. For example, excipients can include ascorbic acid and other antioxidants, chelating agents such as EDTA, carbohydrates such as dextrin, hydroxyalkylcellulose, hydroxyalkylmethylcellulose, stearic acid and the like.

While it is possible for the active ingredient to be administered alone, it may be preferable to present the active ingredient as pharmaceutical compositions. The compositions, both for veterinary and for human use, comprise at least the compound of formula (Ia) or (Ib), together with one or more acceptable carriers and optionally other therapeutic ingredients. In one embodiment, the pharmaceutical composition comprises a compound of formula (Ia) or (Ib), or a pharmaceutically acceptable salt thereof, a pharmaceutically acceptable excipient and a therapeutically effective amount of one or more (e.g., one, two, three, or four; or one or two; or one to three; or one to four) additional therapeutic agents as defined hereinbefore. In one embodiment, the pharmaceutical composition comprises a compound of formula (Ia) or (Ib), or a pharmaceutically acceptable salt thereof, a pharmaceutically acceptable excipient and one other therapeutic ingredient. The carrier(s) are "acceptable" in the sense of being compatible with the other ingredients of the composition and physiologically innocuous to the recipient thereof.

In some embodiments, even though it is possible for the active ingredient to be administered alone, it may be preferable to present the active ingredient as pharmaceutical compositions. The compositions, both for veterinary and for human use, comprise at least the compound of Formula (Ia), (Ib), (IIa), and/or (IIb), together with one or more acceptable carriers and optionally other therapeutic ingredients. In some embodiments, the pharmaceutical composition comprises a compound of Formula (Ia), (Ib), (IIa), and/or (IIb), or a pharmaceutically acceptable salt thereof, a pharmaceutically acceptable excipient and a therapeutically effective amount of one or more (e.g., one, two, three, or four; or one or two; or one to three; or one to four) additional therapeutic agents as defined hereinbefore. In some embodiments, the pharmaceutical composition comprises a compound of Formula (Ia), (Ib), (IIa), and/or (IIb), or a pharmaceutically acceptable salt thereof, a pharmaceutically acceptable excipient and one other therapeutic ingredient. The carrier(s) are "acceptable" in the sense of being compatible with the other ingredients of the composition and physiologically innocuous to the recipient thereof.

The compositions include those suitable for various administration routes. The compositions may conveniently be presented in unit dosage form and may be prepared by any of the methods well known in the art of pharmacy. Such methods include the step of bringing into association the active ingredient (e.g., a compound of formula (Ia) or (Ib) or a pharmaceutical salt thereof) with one or more inactive ingredients (e.g., a carrier, pharmaceutical excipient, etc.). The compositions may be prepared by uniformly and intimately bringing into association the active ingredient with liquid carriers or finely divided solid carriers or both, and then, if necessary, shaping the product. Techniques and formulations generally are found in Remington: The Science and Practice of Pharmacy, $21^{st}$ Edition, Lippincott Williams and Wilkins, Philadelphia, Pa., 2006.

In some embodiments, the compositions include those suitable for various administration routes. The compositions may conveniently be presented in unit dosage form and may be prepared by any of the methods well known in the art of pharmacy. Such methods include the step of bringing into association the active ingredient (e.g., a compound of Formula (Ia), (Ib), (IIa), and/or (IIb), or a pharmaceutical salt thereof) with one or more inactive ingredients (e.g., a carrier, pharmaceutical excipient, etc.). The compositions may be prepared by uniformly and intimately bringing into association the active ingredient with liquid carriers or finely divided solid carriers or both, and then, if necessary, shaping the product. Techniques and formulations generally are found in Remington: The Science and Practice of Pharmacy, $21^{st}$ Edition, Lippincott Williams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient.

When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In some embodiments, disclosed herein are oral dosage forms (e.g., tablets), which may be prepared from hot melt extrusion or spray-drying dispersion (SDD) technologies.

In some embodiments, disclosed herein are hard capsules filled with powder, beads, or granules containing the active ingredient in admixture with non-toxic pharmaceutically acceptable excipient which are suitable for manufacture of hard or soft capsules. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc.

In some embodiments, disclosed herein are hard or soft capsules filled with liquid or semi-solid mixtures containing the active ingredient in admixture with non-toxic pharmaceutically acceptable excipient which are suitable for manufacture of hard or soft capsules. These excipients may be, for example, solubilizing oils such as maize oil, sesame oil, or corn oil; medium chain triglycerides and related esters, such as, derivitized palm kernel oil or coconut oil; self-emulsifying lipid systems (SEDDS or SMEDDS), such as caprylic triglyceride or propylene glycol monocaprylate; viscosity modifiers, such as, cetyl alcohol, steryl alcohol, glycerol stearate; and solubilizing agents and surfactants, such as polyethylene glycol, propylene glycol, glycerin, ethanol, polyethoxylated castor oil, poloxamers, or polysorbates.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments, the sterile injectable preparation disclosed herein may also be a sterile injectable solution or suspension prepared from a reconstituted lyophilized powder in a non-toxic parenterally acceptable diluent or solvent, such as a solution in 1,3-butane-diol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009.

Examples of solubilizing excipients in a parenteral formulation (e.g., an SC or IM formulation) include, but are not limited to, polysorbates (such as polysorbate 20 or 80) and poloxamers (such as poloxamer 338, 188, or 207). In some embodiments, disclosed herein is a parenteral administration (e.g., an SC or IM formulation) that comprises a compound of Formula (Ia), (Ib), (IIa), and/or (IIb), or a pharmaceutical salt thereof, and a poloxamer, in particular poloxamer 338. In some embodiments, the amount of poloxamer (e.g., poloxamer 388) in a parenteral administration disclosed herein is less than about 5%, such as less than about 3%, about 2%, about 1%, or about 0.5%.

Examples of solubilizing excipients in a parenteral formulation (e.g., an SC or IM formulation) include, but are not limited to, polysorbates (such as polysorbate 20 or 80), poloxamers (such as poloxamer 338, 188, or 207). In some embodiments, disclosed herein is a parenteral administration (e.g., an SC or IM formulation) that comprises a compound of Formula (Ia), (Ib), (IIa), and/or (IIb), or a pharmaceutical salt thereof, and a poloxamer.

In certain embodiments, excipients include N-methyl-2-pyrrolidone (NMP), dimethyl sulfoxide, polyethylene glycol and/or tetraglycol/glycofurol.

In general, poloxamers are synthetic non-ionic triblock of linear copolymers having a central hydrophobic chain of polyoxypropylene adjacent to two hydrophilic polypropylene oxide, in certain instances in a 4:2:4 weight ratio. Accordingly, in certain embodiments, the compositions disclosed herein include a compound of Formula (Ia), (Ib), (IIa), and/or (IIb), or a pharmaceutical salt thereof, and a block copolymer comprised of one polyoxypropylene segment and two hydrophilic polypropylene oxide segments. In certain embodiments, the ratio of the polyoxypropylene segment to the two hydrophilic polypropylene oxide segments is 4:2:4 (hydrophilic polypropylene oxide:polyoxypropylene:hydrophilic polypropylene oxide). Poloxamers are generally understood to have the following structure:

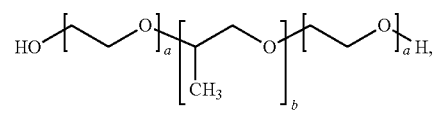

where a and b are integers (e.g. a is 2-130 and b is 15-67). Poloxamer 188, for example, is understood to range in molecular weight from about 7680 to about 9510 Daltons (where a is about 80 and b is about 27). International Journal of PharmTech Research, Vol. 1, No. 2, pp 299-303, April-June 2009. In some instances, poloxamer 188 has an average molecular weight of about 8400 Daltons. Similarly, poloxamer 338 has a molecular weight in the range of from about 12700 to about 17400 Da (where a is about 141 and b is about 44).

Examples of excipients in a parenteral formulation (e.g. an SC or an IM formulation) may also include polyethylene glycol. In general, polyethylene glycol (PEG) is a polyether having a general formula H—(O—CH$_2$—CH$_2$)$_n$—OH. In certain embodiments the PEG may be "capped" by an alkyl group. In those embodiments, the capped PEG is of the formula alkyl-(O—CH$_2$—CH$_2$)$_n$—O-alkyl (e.g. CH$_3$—(O—CH$_2$—CH$_2$)$_n$—OCH$_3$. The pharmaceutical compositions of the present disclosure may include PEG having an average molecular weight of approximately 100 to approximately 1000. In some embodiments, the average molecular weight of PEG within the pharmaceutical composition is approximately 100 to approximately 800. In some embodiments, the average molecular weight of PEG within the pharmaceutical composition is approximately 200 to approximately 600. In some embodiments, the average molecular weight of PEG within the pharmaceutical composition is approximately 400. In some embodiments, the average molecular weight of PEG within the pharmaceutical composition is approximately 300. In some embodiments, the average molecular weight of PEG within the pharmaceutical composition is approximately 200. In some embodiments of the pharmaceutical composition, different molecular weight PEG may be combined to obtain a desired property or properties (e.g. viscosity). Specific examples of PEG include but are not limited to PEG 100, PEG 200, PEG 300, PEG 400, PEG 500, PEG 600, and so forth. PEG 100, for example, refers to a polyethylene glycol with an average molecular weight of about 100.

In some embodiments, the parenteral formulation (e.g., an SC or IM formulation) disclosed herein is an aqueous suspension. In some embodiments, the parenteral formulation (e.g., an SC or IM formulation) disclosed herein is an aqueous suspension that comprises a compound of Formula (Ia), (Ib), (IIa), and/or (IIb), or a pharmaceutical salt thereof, and saline. In some embodiments, the parenteral formulation (e.g., an SC or IM formulation) disclosed herein is an aqueous suspension that comprises a compound of Formula (Ia), (Ib), (IIa), and/or (IIb), or a pharmaceutically acceptable salt thereof, saline, and a poloxamer (such as poloxamer 338, 188, or 207).

In some embodiments, the parenteral formulation (e.g., an SC or IM formulation) disclosed herein is an aqueous suspension. In some embodiments, the parenteral formulation (e.g., an SC or IM formulation) disclosed herein is an aqueous suspension that comprises a compound of Formula (Ia), (Ib), (IIa), and/or (IIb), or a pharmaceutical salt thereof, and saline. In some embodiments, the parenteral formulation (e.g., an SC or IM formulation) disclosed herein is an aqueous suspension that comprises a compound of Formula (Ia), (Ib), (IIa), and/or (IIb), or a pharmaceutically acceptable salt thereof, saline, and a suspending agent. In some embodiments, the parenteral formulation (e.g., an SC or IM formulation) disclosed herein is an aqueous suspension that comprises a compound of Formula (Ia), (Ib), (IIa), and/or (IIb), or a pharmaceutically acceptable salt thereof, saline, and poloxamer (such as poloxamer 338, 188, or 207).

In some embodiments, a suspension comprising a compound of Formula (Ia), (Ib), (IIa), and/or (IIb), or a pharmaceutical salt thereof, in a poloxamer and saline is provided. In some embodiments, the concentration of poloxamer in saline is from about 0.1 to about 20%. In some embodiments, the concentration of poloxamer in saline is from about 0.1 to about 10%. In some in embodiments, the concentration of poloxamer in saline is about 0.1%, 0.2%, 0.3%, 0.4%, 0.5%, 0.6%, 0.7%, 0.8%, 0.9%, 1%, 2,%, 3%, 4%, 5%, 6%, 7%, 8%, 9%, or about 10%. In certain embodiments, the concentration of poloxamer in saline is about 2%. In certain embodiments, the poloxamer is poloxamer 188. In certain embodiments, the compound is a compound of Formula (Ib) or a pharmaceutically acceptable salt thereof. In certain embodiments, the compound is a compound of Formula (Ib). In certain embodiments, the compound is a sodium salt of the compound of Formula (Ib).

In some embodiments, a suspension comprising a compound of Formula (Ia), (Ib), (IIa), and/or (IIb), or a pharmaceutical salt thereof, in a poloxamer and mannitol is provided. In some embodiments, the concentration of poloxamer in mannitol is from about 0.1 to about 20%. In some embodiments, the concentration of poloxamer in mannitol is from about 0.1 to about 10%. In some in embodiments, the concentration of poloxamer in mannitol is about 0.1%, 0.2%, 0.3%, 0.4%, 0.5%, 0.6%, 0.7%, 0.8%, 0.9%, 1%, 2,%, 3%, 4%, 5%, 6%, 7%, 8%, 9%, or about 10%. In certain embodiments, the concentration of poloxamer in mannitol is about 2%. In certain embodiments, the poloxamer is poloxamer 188. In certain embodiments, the compound is a compound of Formula (Ib) or a pharmaceutically acceptable salt thereof. In certain embodiments, the compound is a compound of Formula (Ib). In certain embodiments, the compound is a sodium salt of the compound of Formula (Ib).

In certain embodiments, the composition is disclosed as a solid dosage form, including a solid injectable dosage form, such as a solid depot form.

In certain embodiments, the active ingredient (e.g. a compound of Formula Ib) is present as a free acid. In certain embodiments, the active ingredient (e.g. a compound of Formula Ib) is present as a sodium salt.

In certain embodiments the pharmaceutical composition disclosed herein is a parenteral formulation. In certain embodiments, the formulation is administered subcutaneously to a subject in need thereof. In certain embodiments, the formulation is administered intramuscularly to a subject in need thereof.

In certain embodiments, the parenteral formulation comprises N-methyl-2-pyrrolidone. In certain embodiments, the parenteral formulation consists essentially of N-methyl-2-pyrrolidone. In certain embodiments, the parenteral formulation comprises dimethyl sulfoxide.

In certain embodiments, the parenteral formulation comprises a compound of Formula (Ia), (Ib), (IIa), and/or (IIb), or a pharmaceutical salt thereof and water. In certain embodiments, the parenteral formulation comprises a compound of Formula (Ib) or a pharmaceutical salt thereof and water. In certain embodiments, the parenteral formulation further comprises an alcohol. In certain embodiments, the alcohol is ethanol. In certain embodiments, the parenteral formulation further comprises polyethylene glycol. In certain embodiments, the polyethylene glycol has an average molecular weight of about 200 g/mol. (polyethylene glycol 200). In certain embodiments, the parenteral formulation further comprises an inorganic base. In certain embodiments, the inorganic base is sodium hydroxide. In certain embodiments, the the inorganic base a sodium ethoxide. In certain embodiments the formulation comprises from about 0.1 molar equivalents to about 1.5 molar equivalents of the inorganic base (e.g. NaOH or NaOEt). In certain embodiments, the formulation comprises from about 0.5 molar equivalents to about 1.5 molar equivalents of the inorganic base (e.g. NaOH or NaOEt). In certain embodiments the formulation comprises from about 1.0 molar equivalents to about 1.2 molar equivalents of the inorganic base (e.g. NaOH or NaOEt). In certain embodiments the formulation comprises about 1.2 molar equivalents inorganic base (e.g. NaOH or NaOEt).

In certain embodiments, the parenteral formulation consists essentially of a compound of Formula (Ib) or a pharmaceutical salt thereof, water, ethanol, and polyethylene glycol 200.

In certain embodiments, the parenteral formulation consists essentially of a compound of Formula (Ib) or a pharmaceutical salt thereof, water, ethanol, polyethylene glycol 200 (polyethylene glycole with an average molecular weight of 200 g/mol.), and NaOH. In certain embodiments, the parenteral formulation consists essentially of a compound of Formula (Ib) or a pharmaceutical salt thereof, water, ethanol, polyethylene glycol 200, and NaOEt. In certain embodiments, the formulation comprises from about 0.1 molar equivalents to about 1.5 molar equivalents of NaOH or NaOEt. In certain embodiments, the formulation comprises from about 0.5 molar equivalents to about 1.5 molar equivalents of NaOH or NaOEt. In certain embodiments the formulation comprises from about 1.0 molar equivalents to about 1.2 molar equivalents of NaOH or NaOEt. In certain embodiments the formulation comprises about 1.2 molar equivalents of NaOH or NaOEt.

In certain embodiments, the parenteral formulation is a solution formulation comprises a mixture of ethanol, water, and polyethylene glycol. In certain embodiments, the parenteral formulation is a solution formulation comprising a mixture of ethanol, water, and PEG 200. In certain embodiments, the solution formulation comprises about 5%-20% ethanol, about 5% to 20% water, and about 60% to 90% PEG 200. In certain embodiments, the solution formulation comprises about 10%-15% ethanol, about 10% to 15% water, and about 70% to 80% PEG 200. In certain embodiments, the solution formulation comprises about 10% ethanol, about 12% water, and about 78% PEG 200. In certain embodiments, the solution formulation further comprises an inorganic base. In certain embodiments, the solution formulation further comprises sodium hydroxide or sodium ethoxide. In certain embodiments, the solution formulation further comprises sodium hydroxide. In certain embodiments the formulation comprises from about 0.1 molar equivalents to about 1.5 molar equivalents of the inorganic base (e.g. NaOH or NaOEt). In certain embodiments, the formulation comprises from about 0.5 molar equivalents to about 1.5 molar equivalents of the inorganic base (e.g. NaOH or NaOEt). In certain embodiments the formulation comprises from about 1.0 molar equivalents to about 1.2 molar equivalents of the inorganic base (e.g. NaOH or NaOEt). In certain embodiments the formulation comprises about 1.2 molar equivalents inorganic base (e.g. NaOH or NaOEt).

In some embodiments, solution formulations containing 200 mg/mL of Formula Ib with about 0.1 to about 1.5 equivalents of NaOH in about 10% ethanol, about 12% water, and about 77% PEG are provided.

In certain embodiments, an oral formulation of a compound of Formula (Ia), (Ib), (IIa), and/or (IIb), comprising at least one excipient is provided. Excipients can include ethanol, medium chain triglycerides (e.g. MIGLYOL 810, MIGLYOL 821, MIGLYOL 840, and so forth), Vitamin E TPGS, glycerin, and/or pharmaceutically acceptable oils (e.g. sesame oil, castor oil, safflower oil, vegetable oil, soybean oil, and so forth). Oral formulations disclosed herein can include any combination of one or more suitable excipients. Excipients taken together can be present in >65% by weight of the total oral formulation, >70% by weight of the total oral formulation, >80% by weight of the total oral formulation, >90% by weight of the total oral formulation, or >95% by weight of the total oral formulation.

In some embodiments, an oral formulation of a compound of Formula (Ia), (Ib), (IIa), and/or (IIb), is provided. In certain embodiments the oral formulation comprises a compound of Formula (Ia), (Ib), (IIa), and/or (IIb), about 5% to about 20% ethanol, about 10% to about 30% Vitamin E TPGS, and about 50% to about 85% MIGLYOL 812. In some embodiments, the oral formulation comprises a compound of Formula (Ia), (Ib), (IIa), and/or (IIb), about 8% to about 15% ethanol, about 15% to about 25% Vitamin E TPGS, and about 60% to about 77% MIGLYOL 812. In certain embodiments the oral formulation comprises a compound of Formula (Ia), (Ib), (IIa), and/or (IIb), in about 10% ethanol, about 20% Vitamin E TPGS, and about 70% MIGLYOL 812. In certain embodiments, the oral formulation is prepared in hard gelatin capsules.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the compositions of these embodiments may include other agents conventional in the art having regard to the type of composition in question, for example those suitable for oral administration may include flavoring agents.

In certain embodiments, a composition comprising an active ingredient disclosed herein (e.g., a compound of formula (Ia) or (Ib), or a pharmaceutically acceptable salt thereof) in one variation does not contain an agent that affects the rate at which the active ingredient is metabolized. Thus, it is understood that compositions comprising a compound of formula (Ia) or (Ib) in certain embodiments do not comprise an agent that would affect (e.g., slow, hinder or retard) the metabolism of a compound of formula (Ia) or (Ib) or any other active ingredient administered separately, sequentially or simultaneously with a compound of formula (Ia) or (Ib). It is also understood that any of the methods, kits, articles of manufacture and the like detailed herein in certain embodiments do not comprise an agent that would affect (e.g., slow, hinder or retard) the metabolism of a compound of formula (Ia) or (Ib) or any other active ingredient administered separately, sequentially or simultaneously with a compound of any one of formula (Ia) or (Ib).

In some embodiments, a composition comprising an active ingredient disclosed herein (e.g., a compound of Formula (Ia), (Ib), (IIa), and/or (IIb), or a pharmaceutically acceptable salt thereof) in one variation does not contain an agent that affects the rate at which the active ingredient is metabolized. Thus, it is understood that compositions comprising a compound of Formula (Ia), (Ib), (IIa), and/or (IIb) in certain embodiments do not comprise an agent that would affect (e.g., slow, hinder or retard) the metabolism of a compound of Formula (Ia), (Ib), (IIa), and/or (IIb) or any other active ingredient administered separately, sequentially or simultaneously with a compound of Formula (Ia), (Ib), (IIa), and/or (IIb). It is also understood that any of the methods, kits, articles of manufacture and the like detailed herein in certain embodiments do not comprise an agent that would affect (e.g., slow, hinder or retard) the metabolism of a compound of Formula (Ia), (Ib), (IIa), and/or (IIb) or any other active ingredient administered separately, sequentially or simultaneously with a compound of any one of Formula (Ia), (Ib), (IIa), and/or (IIb).

Methods of Use

In certain embodiments, a method for treating or preventing an HIV infection in a subject (e.g., a human), comprising administering a compound of formula (Ia) or (Ib), or a pharmaceutically acceptable salt thereof, to the subject is disclosed.

In some embodiments, a method for treating or preventing an HIV infection in a subject (e.g., a human), comprising administering a compound of Formula (Ia), (Ib), (IIa), and/or (IIb), or a pharmaceutically acceptable salt thereof, to the subject is disclosed. In certain embodiments, a method for inhibiting the replication of the HIV virus, treating AIDS or delaying the onset of AIDS in a subject (e.g., a human), comprising administering a compound of formula (Ia) or (Ib), or a pharmaceutically acceptable salt thereof, to the subject is disclosed.

In some embodiments, a method for inhibiting the replication of the HIV virus, treating AIDS or delaying the onset of AIDS in a subject (e.g., a human), comprising administering a compound of Formula (Ia), (Ib), (IIa), and/or (IIb), or a pharmaceutically acceptable salt thereof, to the subject is disclosed.

In certain embodiments, a method for preventing an HIV infection in a subject (e.g., a human), comprising administering a compound of formula (Ia) or (Ib), or a pharmaceutically acceptable salt thereof, to the subject is disclosed. In certain embodiments, the subject is at risk of contracting the HIV virus, such as a subject who has one or more risk factors known to be associated with contracting the HIV virus.

In some embodiments, a method for preventing an HIV infection in a subject (e.g., a human), comprising administering a therapeutically effective amount of a compound of Formula (Ia), (Ib), (IIa), and/or (IIb), or a pharmaceutically acceptable salt thereof, to the subject is disclosed. In certain embodiments, the subject is at risk of contracting the HIV virus, such as a subject who has one or more risk factors known to be associated with contracting the HIV virus.

In certain embodiments, a method for treating an HIV infection in a subject (e.g., a human), comprising administering a compound of formula (Ia) or (Ib), or a pharmaceutically acceptable salt thereof, to the subject is disclosed.

In some embodiments, a method for treating an HIV infection in a subject (e.g., a human), comprising administering a compound of Formula (Ia), (Ib), (IIa), and/or (IIb), or a pharmaceutically acceptable salt thereof, to the subject is disclosed.

In certain embodiments, a method for treating an HIV infection in a subject (e.g., a human), comprising administering to the subject in need thereof a therapeutically effective amount of a compound of formula (Ia) or (Ib), or a pharmaceutically acceptable salt thereof, in combination with a therapeutically effective amount of one or more (e.g., one, two, three, or four; or one or two; or one to three; or one to four) additional therapeutic agents selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof is disclosed. In certain embodiments, a method for treating an HIV infection in a subject (e.g., a human), comprising administering to the subject in need thereof a therapeutically effective amount of a compound of formula (Ia) or (Ib), or a pharmaceutically acceptable salt thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof is disclosed.

In some embodiments, a method for treating an HIV infection in a subject (e.g., a human), comprising administering to the subject in need thereof a therapeutically effective amount of a compound of Formula (Ia), (Ib), (IIa), and/or (IIb), or a pharmaceutically acceptable salt thereof, in combination with a therapeutically effective amount of one or more (e.g., one, two, three, or four; or one or two; or one to three; or one to four) additional therapeutic agents selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof is disclosed. In certain embodiments, a method for treating an HIV infection in a subject (e.g., a human), comprising administering to the subject in need thereof a therapeutically effective amount of a compound of Formula (Ia), (Ib), (IIa), and/or (IIb), or a pharmaceutically acceptable salt thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof is disclosed. In certain embodiments, a compound of formula (Ia) or (Ib), or a pharmaceutically acceptable salt thereof for use in medical therapy of an HIV infection (e.g. HIV-1 or the replication of the HIV virus (e.g. HIV-1) or AIDS or delaying the onset of AIDS in a subject (e.g., a human)) is disclosed.

In some embodiments, a compound of Formula (Ia), (Ib), (IIa), and/or (IIb), or a pharmaceutically acceptable salt thereof for use in medical therapy of an HIV infection (e.g. HIV-1 or the replication of the HIV virus (e.g. HIV-1) or AIDS or delaying the onset of AIDS in a subject (e.g., a human)) is disclosed.

In certain embodiments, a compound of formula (Ia) or (Ib), or a pharmaceutically acceptable salt thereof for use in the manufacture of a medicament for treating an HIV infection or the replication of the HIV virus or AIDS or delaying the onset of AIDS in a subject (e.g., a human) is disclosed. One embodiment relates to a compound of formula (Ia) or (Ib), or a pharmaceutically acceptable salt thereof, for use in the prophylactic or therapeutic treatment of an HIV infection or AIDS or for use in the therapeutic treatment or delaying the onset of AIDS.

In some embodiments, a compound of Formula (Ia), (Ib), (IIa), and/or (IIb), or a pharmaceutically acceptable salt thereof for use in the manufacture of a medicament for treating an HIV infection or the replication of the HIV virus or AIDS or delaying the onset of AIDS in a subject (e.g., a human) is disclosed. One embodiment relates to a compound of Formula (Ia), (Ib), (IIa), and/or (IIb), or a pharmaceutically acceptable salt thereof, for use in the prophylactic or therapeutic treatment of an HIV infection or AIDS or for use in the therapeutic treatment or delaying the onset of AIDS.

In certain embodiments, the use of a compound of formula (Ia) or (Ib), or a pharmaceutically acceptable salt thereof, for the manufacture of a medicament for an HIV infection in a subject (e.g., a human) is disclosed. In certain embodiments, a compound of any of formula (Ia) or (Ib), or a pharmaceutically acceptable salt thereof, for use in the prophylactic or therapeutic treatment of an HIV infection is disclosed.

In some embodiments, the use of a compound of Formula (Ia), (Ib), (IIa), and/or (IIb), or a pharmaceutically acceptable salt thereof, for the manufacture of a medicament for an HIV infection in a subject (e.g., a human) is disclosed. In certain embodiments, a compound of any of Formula (Ia), (Ib), (IIa), and/or (IIb), or a pharmaceutically acceptable salt thereof, for use in the prophylactic or therapeutic treatment of an HIV infection is disclosed.

In certain embodiments, in the methods of use, the administration is to a subject (e.g., a human) in need of the treatment. In certain embodiments, in the methods of use, the administration is to a subject (e.g., a human) who is at risk of developing AIDS.

Disclosed herein is a compound of formula (Ia) or (Ib), or a pharmaceutically acceptable salt thereof, for use in therapy. In one embodiment, the compound of formula (Ia) or (Ib), or a pharmaceutically acceptable salt thereof, is for use in a method of treating an HIV infection or the replication of the HIV virus or AIDS or delaying the onset of AIDS in a subject (e.g., a human).

In some embodiments, disclosed herein is a compound of Formula (Ia), (Ib), (IIa), and/or (IIb), or a pharmaceutically acceptable salt thereof, for use in therapy. In some embodiments, the compound of Formula (Ia), (Ib), (IIa), and/or (IIb), or a pharmaceutically acceptable salt thereof, is for use in a method of treating an HIV infection or the replication of the HIV virus or AIDS or delaying the onset of AIDS in a subject (e.g., a human).

Also disclosed herein is a compound of formula (Ia) or (Ib), or a pharmaceutically acceptable salt thereof, for use in a method of treating or preventing HIV infection in a subject in need thereof. In certain embodiments, a compound of formula (Ia) or (Ib), or a pharmaceutically acceptable salt thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

In some embodiments, disclosed herein is a compound of Formula (Ia), (Ib), (IIa), and/or (IIb), or a pharmaceutically acceptable salt thereof, for use in a method of treating or preventing HIV infection in a subject in need thereof. In certain embodiments, a compound of Formula (Ia), (Ib), (IIa), and/or (IIb), or a pharmaceutically acceptable salt thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

In one embodiment, a compound of formula (Ia) or (Ib), or a pharmaceutically acceptable salt thereof, in combination with one or more (e.g. one, two, three, or four; or one or two; or one to three; or one to four) additional therapeutic agents as described herein for use in a method of treating or preventing HIV infection in a subject in need thereof is provided. In one embodiment, said additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof. In one embodiment, said additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof.

In some embodiments, a compound of Formula (Ia), (Ib), (IIa), and/or (IIb), or a pharmaceutically acceptable salt thereof, in combination with one or more (e.g. one, two, three, or four; or one or two; or one to three; or one to four) additional therapeutic agents as described herein for use in a method of treating or preventing HIV infection in a subject in need thereof is provided. In one embodiment, said additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof. In one embodiment, said additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof. In one embodiment, a compound of formula (Ia) or (Ib), or a pharmaceutically acceptable salt thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a compound of formula (Ia) or (Ib), or a pharmaceutically acceptable salt thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In some embodiments, a compound of Formula (Ia), (Ib), (IIa), and/or (IIb), or a pharmaceutically acceptable salt thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a compound of Formula (Ia), (Ib), (IIa), and/or (IIb), or a pharmaceutically acceptable salt thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In a particular embodiment, a compound of formula (Ia) or (Ib), or a pharmaceutically acceptable salt thereof, are provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a compound of formula (Ia) or (Ib), or a pharmaceutically acceptable salt thereof. In certain embodiments, methods for reducing the risk of acquiring HIV (e.g., HIV-1 and/or HIV-2) comprise administration of a compound of formula (Ia) or (Ib), or a pharmaceutically acceptable salt thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of the compound of formula (Ia) or (Ib), or pharmaceutically acceptable salt thereof, and a pharmaceutically acceptable excipient.

In some embodiments, a compound of Formula (Ia), (Ib), (IIa), and/or (IIb), or a pharmaceutically acceptable salt thereof, are provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a compound of Formula (Ia), (Ib), (IIa), and/or (IIb), or a pharmaceutically acceptable salt thereof. In certain embodiments, methods for reducing the risk of acquiring HIV (e.g., HIV-1 and/or HIV-2) comprise administration of a compound of Formula (Ia), (Ib), (IIa), and/or (IIb), or a pharmaceutically acceptable salt thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of the compound of Formula (Ia), (Ib), (IIa), and/or (IIb), or pharmaceutically acceptable salt thereof, and a pharmaceutically acceptable excipient.

In certain embodiments, methods for reducing the risk of acquiring HIV (e.g., HIV-1 and/or HIV-2) comprise administration of a compound of formula (Ia) or (Ib), or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In some embodiments, methods for reducing the risk of acquiring HIV (e.g., HIV-1 and/or HIV-2) comprise administration of a compound of Formula (Ia), (Ib), (IIa), and/or (IIb), or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

In another embodiment, the use of a compound of formula (Ia) or (Ib), or a pharmaceutically acceptable salt thereof, for the manufacture of a medicament for the treatment of an HIV infection in a human being having or at risk of having the infection is disclosed.

In some embodiments, the use of a compound of Formula (Ia), (Ib), (IIa), and/or (IIb), or a pharmaceutically acceptable salt thereof, for the manufacture of a medicament for the treatment of an HIV infection in a human being having or at risk of having the infection is disclosed.

Also disclosed herein is a compound of formula (Ia) or (Ib), or a pharmaceutically acceptable salt thereof, for use in the therapeutic treatment or delaying the onset of AIDS.

In some embodiments, disclosed herein is a compound of Formula (Ia), (Ib), (IIa), and/or (IIb), or a pharmaceutically acceptable salt thereof, for use in the therapeutic treatment or delaying the onset of AIDS.

Also disclosed herein is a compound of formula (Ia) or (Ib), or a pharmaceutically acceptable salt thereof, for use in the prophylactic or therapeutic treatment of an HIV infection.

In some embodiments, disclosed herein is a compound of Formula (Ia), (Ib), (IIa), and/or (IIb), or a pharmaceutically acceptable salt thereof, for use in the prophylactic or therapeutic treatment of an HIV infection.

In certain embodiments, a compound of formula (Ia) or (Ib), or a pharmaceutically acceptable salt thereof can be used as a research tool (e.g. to study the inhibition of HIV reverse transcriptase in a subject or in vitro).

In some embodiments, a compound of Formula (Ia), (Ib), (IIa), and/or (IIb), or a pharmaceutically acceptable salt thereof can be used as a research tool (e.g., to study the inhibition of HIV reverse transcriptase in a subject or in vitro).

Routes of Administration

The compound of the formula (Ia) or (Ib), or a pharmaceutically acceptable salt thereof, (also referred to herein as the active ingredient) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. In certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

In some embodiments, the compound of the Formula (Ia), (Ib), (IIa), and/or (IIb), or a pharmaceutically acceptable salt thereof, (also referred to herein as the active ingredient) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. In certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

In some embodiments, the compound of the Formula (Ia), (Ib), (IIa), and/or (IIb), or a pharmaceutically acceptable salt thereof, may be administered with a syringe suitable for administration of the compound. In some embodiments, the syringe is disposable. In some embodiments, the syringe is reusable. In some embodiments, the syringe is pre-filled with the compound of the Formula (Ia), (Ib), (IIa), and/or (IIb), or a pharmaceutically acceptable salt thereof.

In some embodiments, the compound of the Formula (Ia), (Ib), (IIa), and/or (IIb), or a pharmaceutically acceptable salt thereof, may be administered with an auto-injector comprising a syringe. In some embodiments, the syringe is disposable. In some embodiments, the syringe is reusable. In some embodiments, the syringe is pre-filled with the compound of the Formula (Ia), (Ib), (IIa), and/or (IIb), or a pharmaceutically acceptable salt thereof.

Dosing Regimen

The compound, such as a compound of formula (Ia) or (Ib), or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

In some embodiments, the compound, such as a compound of Formula (Ia), (Ib), (IIa), and/or (IIb), or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In some embodiments, the compound is administered on a daily or intermittent schedule. In some embodiments, the compound is administered on a monthly schedule. In some embodiments, the compound is administered every two months. In some embodiments, the compound is administered every three months. In some embodiments, the compound is administered every four months. I In some embodiments, the compound is administered every five months. In some embodiments, the compound is administered every 6 months.

In some embodiments, the compound, such as a compound of Formula (Ia), (Ib), (IIa), and/or (IIb), or a pharmaceutically acceptable salt thereof, may be administered to a subject at least about one month, at least about 4 months, or at least about 6 months. In some embodiments, the compound (e.g., a compound of Formula (Ia), (Ib), (IIa), and/or (IIb), or a pharmaceutically acceptable salt thereof), may be subcutaneously administered to a subject at least about one month. In some embodiments, the compound (e.g., a compound of Formula (Ia), (Ib), (IIa), and/or (IIb), or a pharmaceutically acceptable salt thereof), may be subcutaneously or intramuscularly administered to a subject at least about 4 months, or at least about 6 months. In some embodiments, the compound (e.g., a compound of Formula (Ia), (Ib), (IIa), and/or (IIb), or a pharmaceutically acceptable salt thereof), may be subcutaneously administered to a subject at least about one month. In some embodiments, the compound (e.g., a compound of Formula (Ia), (Ib), (IIa), and/or (IIb), or a pharmaceutically acceptable salt thereof), may be subcutaneously or intramuscularly administered to a subject at least about every 3 months.

The dosage or dosing frequency of a compound of formula (Ia) or (Ib), or a pharmaceutically acceptable salt thereof, may be adjusted over the course of the treatment, based on the judgment of the administering physician.

In some embodiments, the dosage or dosing frequency of a compound of Formula (Ia), (Ib), (IIa), and/or (IIb), or a pharmaceutically acceptable salt thereof, may be adjusted over the course of the treatment, based on the judgment of the administering physician.

The compound may be administered to a subject (e.g., a human) in an effective amount. In certain embodiments, the compound is administered once daily.

In some embodiments, the compound may be administered to a subject (e.g., a human) in an therapeutically effective amount. In some embodiments, the compound is administered once daily. In some embodiments, the compound is administered monthly. In some embodiments, the compound is administered every three months. In some embodiments, the compound is administered every four months. In some embodiments, the compound is administered every six months.

A compound as disclosed herein (e.g., a compound of formula (Ia) or (Ib)), or a pharmaceutically acceptable salt thereof, may be administered in a dosage amount that is effective. For example, the dosage amount can be from 1 mg to 1000 mg of compound. In certain embodiments, the dosage amount is about 10, 20, 30, 40, 50, 60, 70, 80, 90, 95, 100, 105, 110, 120, 130, 140, or 150 mg of compound. In certain embodiments the dosage amount is about 100, 150, 200, 250, 300, 350, 400, 450, 500, 550, 600, 650, 700, 750, 800, 850, 900, 950, or 1000 mg.

In some embodiments, a compound as disclosed herein (e.g., a compound of Formula (Ia), (Ib), (IIa), and/or (IIb)), or a pharmaceutically acceptable salt thereof, may be administered in a dosage amount that is effective. For example, the dosage amount can be from 1 mg to 1000 mg of compound. In certain embodiments, the dosage amount is about 1, 10, 20, 30, 40, 50, 60, 70, 80, 90, 95, 100, 105, 110, 120, 130, 140, or 150 mg of compound. In certain embodiments the dosage amount is about 100, 150, 200, 250, 300, 350, 400, 450, 500, 550, 600, 650, 700, 750, 800, 850, 900, 950, or 1000 mg.

In some embodiments, a compound of Formula (Ia), (Ib), (IIa), and/or (IIb)), or a pharmaceutically acceptable salt thereof, is administered in a once daily dose. In some embodiments, a compound of Formula (Ia), (Ib), (IIa), and/or (IIb)), or a pharmaceutically acceptable salt thereof, is administered in a once daily dose of about 1 mg.

In some embodiments, a compound of Formula (Ia), (Ib), (IIa), and/or (IIb)), or a pharmaceutically acceptable salt thereof, is administered monthly. In some embodiments, a compound of Formula (Ia), (Ib), (IIa), and/or (IIb)), or a pharmaceutically acceptable salt thereof, is administered monthly at a dose of about 100 mg.

In some embodiments, a compound of Formula (Ia), (Ib), (IIa), and/or (IIb)), or a pharmaceutically acceptable salt thereof, is administered every 6 months. In some embodiments, a compound of Formula (Ia), (Ib), (IIa), and/or (IIb)), or a pharmaceutically acceptable salt thereof, is administered every 6 months at a dose of about 600 mg.

Kits and Articles of Manufacture

The present disclosure relates to a kit comprising a compound of formula (Ia) or (Ib), or a pharmaceutically acceptable salt thereof. In one embodiment, the kit may comprise one or more additional therapeutic agents as described hereinbefore. The kit may further comprise instructions for use, e.g., for use in inhibiting an HIV reverse transcriptase, such as for use in treating an HIV infection or AIDS or as a research tool. The instructions for use are generally written instructions, although electronic storage media (e.g., magnetic diskette or optical disk) containing instructions are also acceptable.

In some embodiments, the present disclosure relates to a kit comprising a compound of Formula (Ia), (Ib), (IIa), and/or (IIb), or a pharmaceutically acceptable salt thereof. In one embodiment, the kit may comprise one or more additional therapeutic agents as described hereinbefore. The kit may further comprise instructions for use, e.g., for use in inhibiting an HIV reverse transcriptase, such as for use in treating an HIV infection or AIDS or as a research tool. The instructions for use are generally written instructions, although electronic storage media (e.g., magnetic diskette or optical disk) containing instructions are also acceptable.

The present disclosure also relates to a pharmaceutical kit comprising one or more containers comprising a compound of formula (Ia) or (Ib), or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

In some embodiments, the present disclosure also relates to a pharmaceutical kit comprising one or more containers comprising a compound of Formula (Ia), (Ib), (IIa), and/or (IIb), or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also disclosed are articles of manufacture comprising a unit dosage of a compound of formula (Ia) or (Ib), or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

In some embodiments, disclosed herein are articles of manufacture comprising a unit dosage of a compound of Formula (Ia), (Ib), (IIa), and/or (IIb), or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

Nomenclature

The name of the compound of formula (Ia) and (Ib) of the current disclosure as generated using ChemBioDraw Ultra 11.

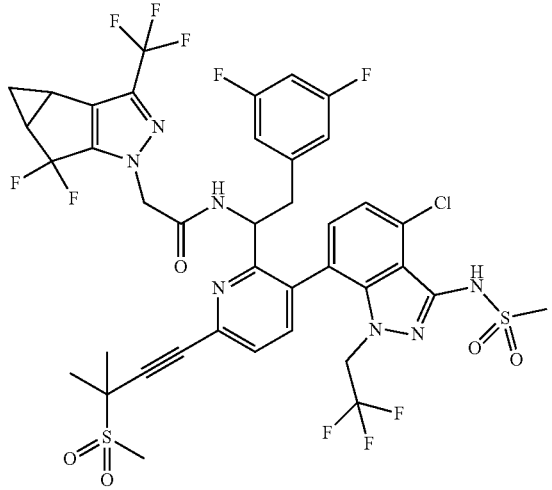 [SMILES: CC(C)(C#Cc1ccc(-c2ccc(Cl)c3c(NS(C)(=O)=O)nn(CC(F)(F)F)c23)c(C(Cc2cc(F)cc(F)c2)NC(=O)Cn2nc(C(F)(F)F)c3c2C(F)(F)C2CC32)n1)S(C)(=O)=O]

is N-(1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-(5,5-difluoro-3-(trifluoromethyl)-3b,4,4a,5-tetrahydro-1H-cyclopropa[3,4]cyclopenta[1,2-c]pyrazol-1-yl)acetamide.

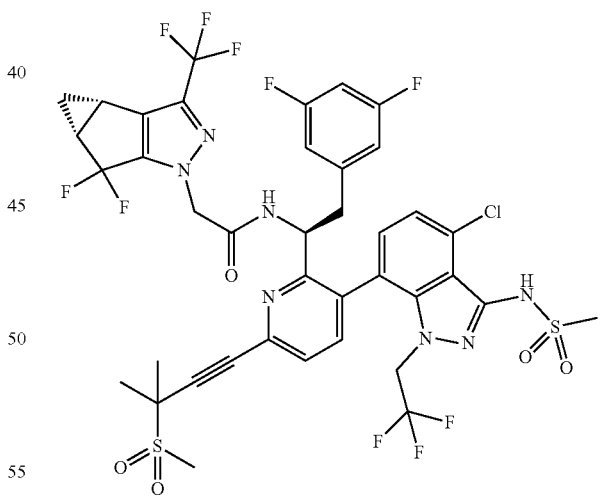

is N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide.

The name of the compound of formula (IIa) and (IIb) of the current disclosure as generated using ChemBioDraw Ultra 14.

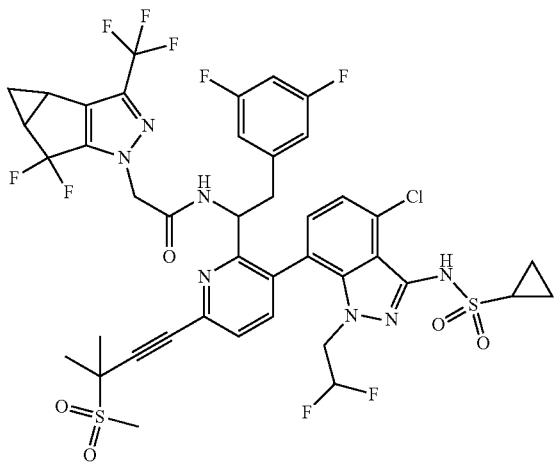 [SMILES: CC(C)(C#Cc1ccc(-c2ccc(Cl)c3c(NS(=O)(=O)C4CC4)nn(CC(F)F)c23)c(C(Cc2cc(F)cc(F)c2)NC(=O)Cn2nc(C(F)(F)F)c3c2C(F)(F)C2CC32)n1)S(C)(=O)=O]

is N-(1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)-2-(3-(difluoromethyl)-5,5-difluoro-3b,4,4a,5-tetrahydro-1H-cyclopropa[3,4]cyclopenta[1,2-c]pyrazol-1-yl)acetamide.

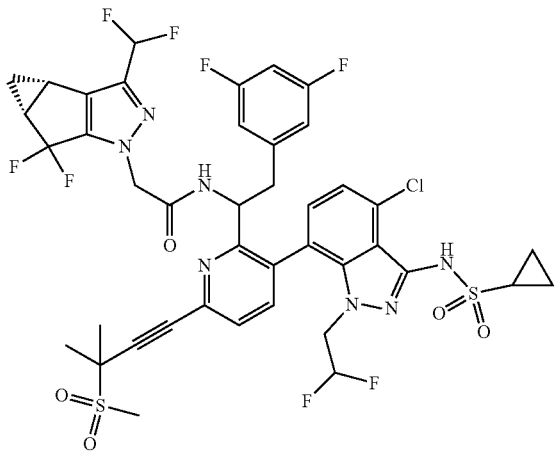 [SMILES: CC(C)(C#Cc1ccc(-c2ccc(Cl)c3c(NS(=O)(=O)C4CC4)nn(CC(F)F)c23)c(C(Cc2cc(F)cc(F)c2)NC(=O)Cn2nc(C(F)F)c3c2C(F)(F)[C@@H]2C[C@H]32)n1)S(C)(=O)=O]

is N—((S)-1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

Synthesis of the Compound of Formula (Ia), (Ib), (IIa), and (IIb)

The present disclosure is also directed to processes and intermediates useful for preparing the subject compound or pharmaceutically acceptable salts thereof.

Except as otherwise noted, the methods and techniques of the present disclosure are generally performed according to conventional methods well known in the art and as described in various general and more specific references that are cited and discussed throughout the present specification. See, e.g., Loudon, Organic Chemistry, 5$^{th}$ edition, New York: Oxford University Press, 2009; Smith, March's Advanced Organic Chemistry: Reactions, Mechanisms, and Structure, 7$^{th}$ edition, Wiley-Interscience, 2013.

In certain instances, the processes disclosed herein involve a step of forming a salt of a compound of the present disclosure.

In certain instances, the intermediates useful in preparing a compound of formula (Ia) or (Ib) of the present disclosure are provided. For example, those intermediates include any one of or a combination of Compounds 1 to 23 or a salt thereof. In certain embodiments, the intermediates are selected from Compound 8a, 12, 14, 19, 20, 21, 22, 23, and/or 23b, combinations thereof, or salts thereof.

In some embodiments, the intermediates useful in preparing a compound of formula (IIa) or (IIb) of the present disclosure are provided. For example, those intermediates include any one of or a combination of Compounds 1, 10, 20 and 25-37 or a salt thereof. In some embodiments, the intermediates are selected from Compound 20, 32, 34, 35, 36, and/or 37, combinations thereof, or salts thereof.

Compounds as described herein can be purified by any of the means known in the art, including chromatographic means, such as high performance liquid chromatography (HPLC), preparative thin layer chromatography, flash column chromatography, supercritical fluid chromatography (SFC), and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2$^{nd}$ ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. One of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The compounds disclosed herein may display atropisomerism resulting from steric hindrance affecting the axial rotation rate around a single bond. The resultant conformational isomers may each be observed as distinct entities by characterization techniques such as NMR and HPLC. The compounds disclosed herein may exist as a mixture of atropisomers. However, the detection of atropisomers is dependent on factors such as temperature, solvent, conditions of purification, and timescale of spectroscopic technique. The interconversion rate at room temperature has a half-life of minutes to hours, hours to days, or days to years. The ratio of atropisomers at equilibrium may not be unity. Characterization data presented herein may not represent the equilibrium state depending on the conditions of isolation and characterization which may include but not limited to handling, solvents used, and temperature.

Representative syntheses of compounds of the present disclosure are described in schemes below, and the particular examples that follow. The following examples are merely illustrative, and not intended to limit this disclosure in any way.

Preparation of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (8a) and 2-((3bR,4aS)-5,5-difluoro-3-(trifluoromethyl)-3b,4,4a,5-tetrahydro-1H-cyclopropa[3,4]cyclopenta[1,2-c]pyrazol-1-yl)acetic Acid (8b)

Example 1

Preparation of Compounds 8a and 8b

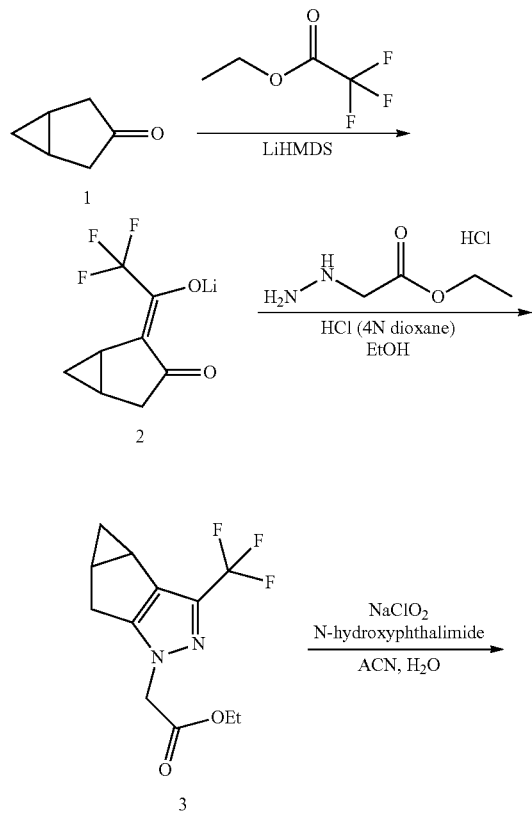

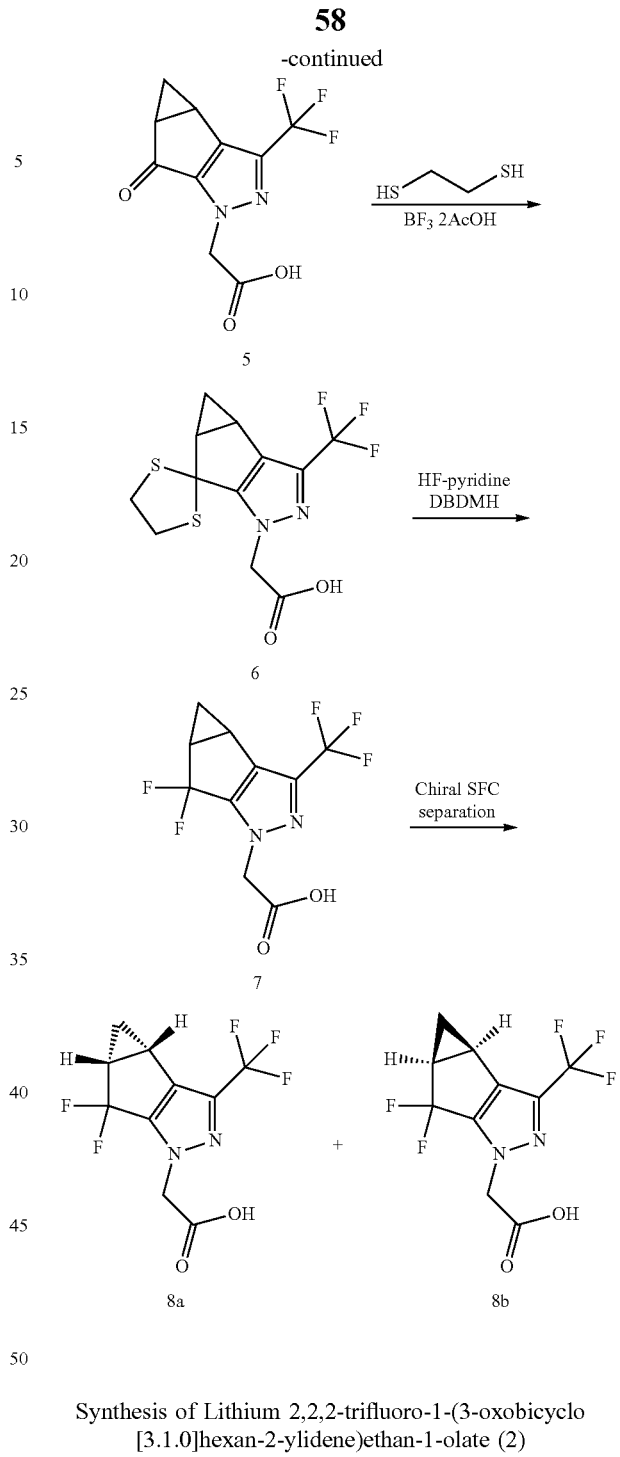

Synthesis of Lithium 2,2,2-trifluoro-1-(3-oxobicyclo[3.1.0]hexan-2-ylidene)ethan-1-olate (2)

A reactor was charged with bicyclo[3.1.0]hexan-3-one (95.6 g, 0.99 mol) and ethyl 2,2,2-trifluoroacetate (113.2 mL, 0.95 mol) and THF (50 mL). The reaction mixture was cooled to 0° C. LiHMDS (Lithium bis(trimethylsilyl)amide) (1 L of 1.0M solution in THF, 1 mol) was added via an addition funnel at a rate to maintain internal temperature at ≤1° C. After the addition was complete, hexanes (235 mL) was added in a steady stream via an addition funnel and stirred for 15 min. The resultant solids were collected by filtration, washed with hexanes (3×400 mL), and dried to provide the title compound.

Synthesis of Ethyl 2-(3-(trifluoromethyl)-3b,4,4a,5-tetrahydro-1H-cyclopropa[3,4]cyclopenta[1,2-c]pyrazol-1-yl)acetate (3)

A reactor was charged with lithium 2,2,2-trifluoro-1-(3-oxobicyclo[3.1.0]hexan-2-ylidene)ethan-1-olate (177.2 g, 0.89 mol) and EtOH (ethanol) (779 mL). The temperature was brought to and maintained at 0° C. HCl in dioxane (4.0 N, 443 mL) was added via an addition funnel followed by the addition of solid ethyl hydrazinoacetate HCl salt (138.4 g, 0.90 mol). The reaction temperature was adjusted to 35° C. After 1 h, the reaction volume was reduced by ~40% by distillation at reduced pressure. Water (1.3 L) was added with vigorous agitation and temperature adjusted to 15° C. The resultant solids were collected by filtration, washed with water (3×500 mL), hexanes (3×400 mL), and dried to provide the title compound. MS (m/z) 275.1 [M+H]$^+$.

Synthesis of Ethyl 2-(5-oxo-3-(trifluoromethyl)-3b,4,4a,5-tetrahydro-1H-cyclopropa[3,4]cyclopenta[1,2-c]pyrazol-1-yl)acetate (4)

A reactor was charged with ethyl 2-(3-(trifluoromethyl)-3b,4,4a,5-tetrahydro-1H-cyclopropa[3,4]cyclopenta[1,2-c]pyrazol-1-yl)acetate (291.2 g, 1.06 mol), acetonitrile (1.65 L) and water (825 mL) to which N-hydroxyphthalimide (17.4 g, 0.103 mol) and NaClO$_2$ (41.0 g, 0.45 mol, ~20% of total amount to be added) were added. The reaction mixture was heated to 50° C. and the remaining NaClO$_2$ (163.0 g, 1.80 mol) was added in five portions over 2 h. After consumption of starting material, the temperature was adjusted to 20° C. and aqueous sodium bisulfite (40% w/w, 350 mL) was added via an addition funnel. Ethyl acetate (1.75 L) was added and the layers were separated. The aqueous layer was back extracted with EtOAc (ethyl acetate) (500 mL). The organic layers were combined and washed with saturated aqueous NaHCO$_3$ (500 mL) and 1:1 water/brine (500 mL). The organic layer was concentrated under reduced pressure and co-evaporated with IPAc (isopropyl acetate) (300 mL). The crude solid was crystallized from a mixture of IPAc/heptane. The resultant solids were collected by filtration, washed with heptane, and dried to provide the title compound. MS (m/z) 289.0 [M+H]$^+$.

Synthesis of 2-(5-oxo-3-(trifluoromethyl)-3b,4,4a,5-tetrahydro-1H-cyclopropa[3,4]cyclopenta[1,2-c]pyrazol-1-yl)acetic Acid (5)

To a solution of ethyl 2-(5-oxo-3-(trifluoromethyl)-3b,4,4a,5-tetrahydro-1H-cyclopropa[3,4]cyclopenta[1,2-c]pyrazol-1-yl)acetate (80.40 g, 278.95 mmol) in 2-MeTHF (2-methyltetrahydrofuran) (167 mL) was added 2M aqueous sodium hydroxide (167 mL). After 25 minutes of stirring at room temperature, the reaction mixture was diluted with 2-MeTHF and was slowly acidified by the dropwise addition of concentrated HCl. The organic layer was isolated and the aqueous layer was extracted with an additional portion of 2-MeTHF. The combined organic layers were washed with saturated aqueous sodium chloride, then dried over sodium sulfate, filtered, and concentrated. The resulting oil was taken in ethyl acetate. Hexanes was added with vigorous stirring until solid formation was observed. The solid was isolated by filtration and dried to provide the title compound. MS (m/z) 259.00 [M−H]$^-$.

Synthesis of 2-(3-(trifluoromethyl)-4,4a-dihydrospiro[cyclopropa[3,4]cyclopenta[1,2-c]pyrazole-5,2'-[1,3]dithiolane]-1(3bH)-yl)acetic Acid (6)

To a solution of 2-(5-oxo-3-(trifluoromethyl)-3b,4,4a,5-tetrahydro-1H-cyclopropa[3,4]cyclopenta[1,2-c]pyrazol-1-yl)acetic acid (3.0 g, 11.5 mmol) in DCM (dichloromethane) (25 mL) was added 1,2-ethanedithiol (1.07 mL, 12.68 mmol) followed by boron trifluoride-acetic acid complex (4.0 mL, 28.8 mmol). The reaction mixture was stirred at room temperature overnight. To the reaction mixture was added water (60 mL) and 2-MeTHF (60 mL). The organic layer was isolated, dried over sodium sulfate, filtered, and concentrated. The crude was dissolved in ethyl acetate (2 mL) and the solution diluted with hexanes (12 mL) with vigorous stirring to provide a solid. The solid was isolated by filtration and dried to provide the title compound. MS (m/z) 337.12 [M+H]$^+$.

Synthesis of 2-(5,5-difluoro-3-(trifluoromethyl)-3b,4,4a,5-tetrahydro-1H-cyclopropa[3,4]cyclopenta[1,2-c]pyrazol-1-yl)acetic Acid (7)

To a suspension of 1,3-dibromo-5,5-dimethylhydantoin (12.75 g, 44.6 mmol) in DCM (35 mL) was added pyridine hydrofluoride (5.0 mL) at 0° C. The suspension was stirred at 0° C. for 10 minutes. To the suspension was added a solution of 2-(3-(trifluoromethyl)-4,4a-dihydrospiro[cyclopropa[3,4]cyclopenta[1,2-c]pyrazole-5,2'-[1,3]dithiolane]-1(3bH)-yl)acetic acid (5.00 g, 14.9 mmol) dropwise. After addition was complete, the reaction mixture was stirred at 0° C. for an additional 15 minutes. The reaction mixture was poured into saturated aqueous sodium bicarbonate solution (300 mL) with vigorous stirring. The organic layer was removed and the aqueous layer was acidified to pH ~1 with concentrated HCl. The aqueous phase was extracted with three portions of MTBE (methyl tert-butyl ether). The combined organic layers were dried over sodium sulfate, filtered, and concentrated. The resulting solid was taken in MTBE (16 mL) and filtered to remove any resulting solid. The solution was then extracted with 2N NaOH (16 mL). The aqueous layer was diluted with water (16 mL) with vigorous stirred and stirred at room temperature for 15 minutes. The resulting solid was removed by filtration. The aqueous layer was acidified by slow, dropwise addition of concentrated HCl to pH ~1 with vigorous stirring to provide a solid precipitate. The solid was isolated by filtration to provide the title compound. MS (m/z) 281.12 [M+H]$^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (8a) and 2-((3bR,4aS)-5,5-difluoro-3-(trifluoromethyl)-3b,4,4a,5-tetrahydro-1H-cyclopropa[3,4]cyclopenta[1,2-c]pyrazol-1-yl)acetic Acid (8b)

2-(5,5-Difluoro-3-(trifluoromethyl)-3b,4,4a,5-tetrahydro-1H-cyclopropa[3,4]cyclopenta[1,2-c]pyrazol-1-yl)acetic acid was separated to its constituent enantiomers, the title compounds, by chiral SFC under the following conditions: Instrument: Thar 350 preparative SFC; Column: ChiralPak IC-10 u, 300×50 mm I.D; Mobile phase: 35% Isopropanol (0.1% NH$_3$.H$_2$O) and CO$_2$; Flow rate: 200 mL/min; Column temperature: 38° C.; UV detection: 220 nm; Sample preparation: Compound was dissolved in isopropanol to ~45 mg/mL; Injection: 6.5 mL per injection. Analytical SFC [mobile phase: A for CO$_2$ and B for Isopropanol (0.05% DEA); Gradient: B 20%; A; Flow rate: 2.35 mL/min; Column: Chiralpak IC-3, 150×4.6 mm, 3 um; Wavelength: 254 nm] 8a: t=3.39 min, 8b: t=2.17 min. Compound 8a—$^1$H NMR (400 MHz, Chloroform-d) δ 4.93 (s, 2H), 2.52-2.43 (m, 2H), 1.44-1.38 (m, 1H), 1.15 (m, 1H).

Example 2

Preparation of Compound 12

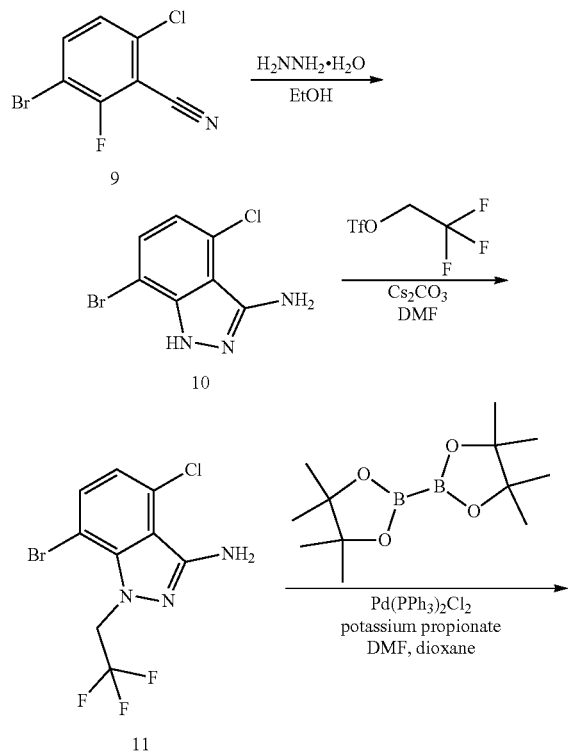

Synthesis of 7-bromo-4-chloro-1H-indazol-3-amine (10)

To 3-bromo-6-chloro-2-fluorobenzonitrile (13.9 g, 59.3 mmol) in EtOH (ethanol) (60 mL) was added hydrazine monohydrate (5.77 mL). The reaction mixture was heated to 80° C. for 3 h. After cooling to ambient temperature, EtOH (20 mL) was added to allow for stirring. The solids were isolated by filtration, washed with cold EtOH, and dried to provide the title compound. MS (m/z) 247.9 [M+H]$^+$.

Synthesis of 7-bromo-4-chloro-1-(2,2,2-trifluoroethyl)-1H-indazol-3-amine (11)

A reactor was charged with 7-bromo-4-chloro-1H-indazol-3-amine (397.2 g, 1.6 mol) and Cs$_2$CO$_3$ (1052 g, 3.2 mol) then diluted with DMF (dimethylformamide) (4000 mL). To this was slowly added 2,2,2-trifluoroethyl trifluoromethanesulfonate (463.2 g, 1.9 mol) via addition funnel. Upon completion of the addition, the reaction mixture was allowed to stir for 1 hour, at which time, H$_2$O (16 L) was added slowly. Upon completion of the addition, the mixture was allowed to stir for 12 hours at 15° C. The slurry was filtered and the collected solids were suspended in DMF (800 mL). To this was added H$_2$O (4800 mL) and the resulting solids were collected by filtration and dried to provide the title compound. MS (m/z) 330.1 [M+H]$^+$.

Synthesis of 4-chloro-7-(4,4,5,5-tetramethyl-1,3,2-dioxaborolan-2-yl)-1-(2,2,2-trifluoroethyl)-1H-indazol-3-amine (12)

A reaction vessel was charged with 7-bromo-4-chloro-1-(2,2,2-trifluoroethyl)-1H-indazol-3-amine (15.00 g, 45.66 mmol), bis(pinacolato)diboron (17.39 g, 68.49 mmol), potassium propionate (15.36 g, 136.98 mmol), dioxane (90 mL) and DMF (dimethylformamide) (30 mL). Bis(triphenylphosphine)palladium(II) dichloride (0.64 g, 0.91 mmol) was added and the reaction solution degassed by bubbling argon for 2 min. The reaction mixture was heated to 105° C. for 4 hrs. After cooling to ambient temperature, the reaction mixture was filtered through a pad of Celite and silica gel washing with EtOAc. The filtrate was washed with 5% LiCl solution and brine. The organic layers were separated, dried, and concentrated under reduced pressure. The residue was treated with IPAc/heptane (1/10) at 60° C. then cooled to ambient temperature and stirred for 15 h. The solids were collected by filtration and dried to afford the title compound. MS (m/z) 376.7 [M+H]$^+$ $^1$H NMR (400 MHz, DMSO-d$_6$) δ 7.69 (d, 1H), 7.06 (d, 1H), 5.55 (s, 2H), 5.45 (q, 2H), 1.32 (s, 12H).

Example 3

Preparation of Compound 14

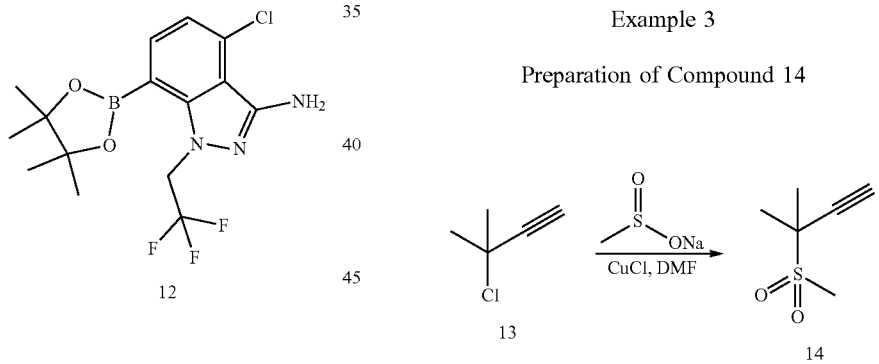

Synthesis of 3-methyl-3-(methylsulfonyl)but-1-yne (14)

To a stirred suspension of sodium methanesulfinate (18.47 g, 175.5 mmol) and copper(I) chloride (1.45 g, 14.6 mmol) in DMF (dimethylformamide) (50 mL) was added 3-chloro-3-methylbut-1-yne (15.00 g, 146.3 mmol, 16.4 mL) dropwise. The resulting reaction mixture was heated to 40° C. and stirred for 16 h. The reaction mixture was cooled to room temperature and diluted with EtOAc. The solution was washed with water and brine. The organic layer was collected and dried over sodium sulfate, then filtered. The solution was concentrated under vacuum and purified by silica gel chromatography to provide the title compound. Mp: 114.8-115.5° C. $^1$H NMR (400 MHz, Chloroform-d) δ 3.04 (s, 3H), 2.58 (s, 1H), 1.67 (s, 6H).

Example 4

Preparation of Compound 19

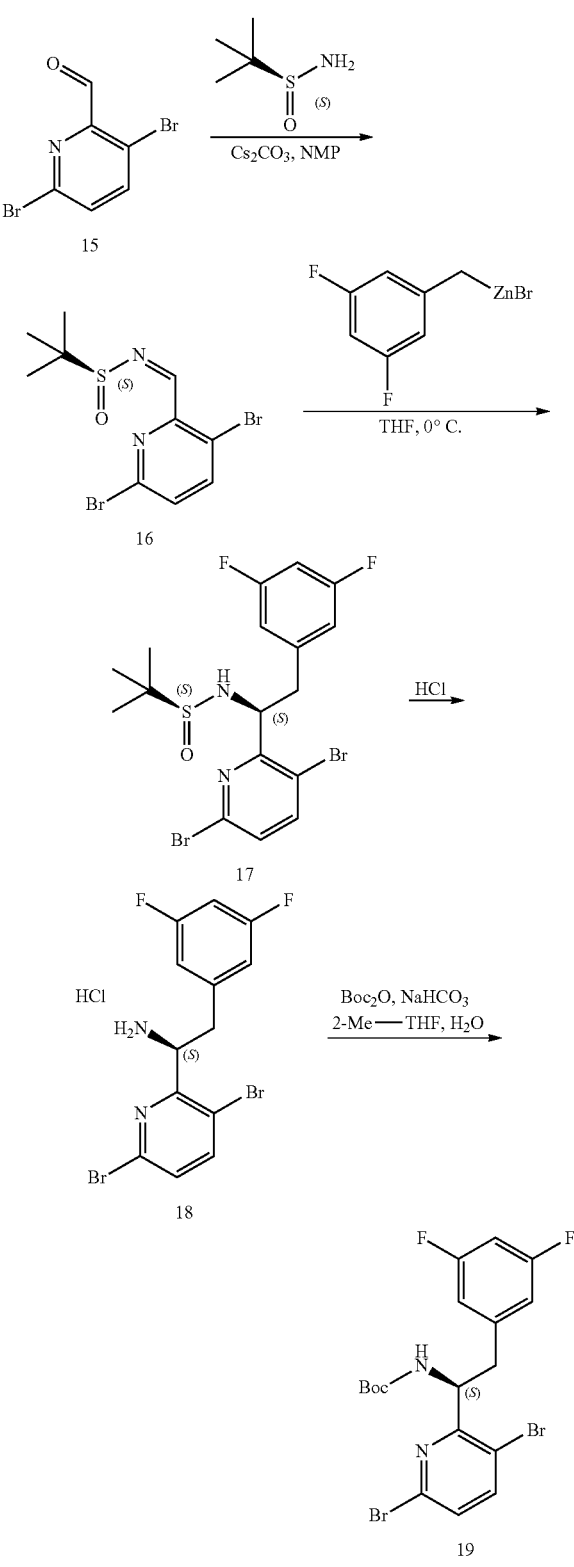

Synthesis of (S)—N-((3,6-dibromopyridin-2-yl)methylene)-2-methylpropane-2-sulfinamide (16)

3,6-Dibromopicolinaldehyde (76.0 g, 0.287 mol) and (S)-2-methylpropane-2-sulfinamide (36.51 g, 0.301 mol) were combined in NMP (N-methyl-2-pyrrolidone) (200 mL). To the reaction mixture was added $Cs_2CO_3$ (41.94 g, 0.316 mol) as a solid in one portion. The reaction mixture was stirred 2 h then cooled to 5° C. Water (1.3 L) was added to the reaction mixture. The resulting suspension was stirred for 1 h, solids isolated by filtration, washed with water (5×100 mL) and dried to provide the title compound. MS (m/z) 368.9 [M+H]$^-$.

Synthesis of (S)—N—((S)-1-(3,6-dibromopyridin-2-yl)-2-(3,5-difluorophenyl)ethyl)-2-methylpropane-2-sulfinamide (17)

A reaction vessel was charged with (S)—N-((3,6-dibromopyridin-2-yl)methylene)-2-methylpropane-2-sulfinamide (65.5 g, 177.95 mmol) followed by DMF (dimethylformamide) (260 mL). The mixture was stirred for 5 min until homogeneous and the solution was cooled to 8° C. To the reaction mixture was added (3,5-difluorobenzyl)zinc bromide (0.5 M in THF (tetrahydrofuran), 516.04 mL) dropwise over 90 mins. The mixture was stirred for an additional 2.5 h. To the reaction mixture, 5% AcOH (acetic acid) in water (640 mL) was added over 10 mins followed by CPME (cyclopentyl methyl ether) (320 mL) in one portion. The mixture was stirred for 5 mins, warmed to room temperature, and the layers were separated. The organic layer was washed with 5% AcOH (320 mL) then treated with 0.5M NaOH (330 mL) and washed with brine. The organic layer was collected, dried with $Na_2SO_4$, and filtered. To the crude mixture was added MeOH (methanol) (33 mL). To the stirring mixture was added dropwise 3M HCl in CPME (128 mL) over 15 mins. After stirring for 1 h, the precipitate was removed by filtration. The filtrate was diluted with hexane (300 mL) and the product was extracted with water (450 mL). The aqueous layer was basified with 8M NaOH and extracted with CPME (375 mL). The organic layer was washed with brine, dried over $Na_2SO_4$ and filtered to provide the title compound in solution which was used directly in the next reaction. MS (m/z) 497.0 [M+H]$^+$.

Synthesis of (S)-1-(3,6-dibromopyridin-2-yl)-2-(3,5-difluorophenyl)ethan-1-amine (18)

The resulting solution of (S)—N—((S)-1-(3,6-dibromopyridin-2-yl)-2-(3,5-difluorophenyl)ethyl)-2-methylpropane-2-sulfinamide was diluted with CPME to a volume of 700 mL to which acetonitrile (350 mL) was added. To the stirring mixture, concentrated HCl (37%, 16.4 mL) was added dropwise over 10 mins at room temperature. The thick slurry was vigorously stirred for 4 h. The solids were filtered and washed with 2:1 CPME (cyclopropyl methyl ether):ACN to provide the title compound. MS (m/z) 393.3 [M+H]$^+$.

Synthesis of Tert-butyl (S)-(1-(3,6-dibromopyridin-2-yl)-2-(3,5-difluorophenyl)ethyl)carbamate (19)

A reaction vessel was charged with 2-MeTHF (190 mL), water (190 mL) and (S)-1-(3,6-dibromopyridin-2-yl)-2-(3,5-difluorophenyl)ethan-1-amine (46.9 g, 0.11 mol) followed by portionwise addition of $NaHCO_3$ (30.34 g, 0.36 mol). The reaction mixture was cooled to 5° C. and di-tert-butyl dicarbonate (27.47 g, 0.13 mol) was added. The reaction mixture was stirred at 0° C. for 2 h and ambient temperature for 2 h. The reaction mixture was diluted with water and extracted with MTBE (methyl tert-butyl ether). The organic layers were washed with brine, dried and concentrated. Crude compound was purified by column chromatography on silica to provide the title compound. MS (m/z) 492.8 [M+H]$^+$. $^1$H NMR (400 MHz, Methanol-d$_4$) δ 7.85 (d, 1H), 7.42 (d, 1H), 6.90-6.72 (m, 3H), 5.33 (dd, 1H), 3.10 (dd, 1H), 2.92 (dd, 1H), 1.36 (s, 9H).

Example 5

Preparation of Formula (Ib) (Compound 24)

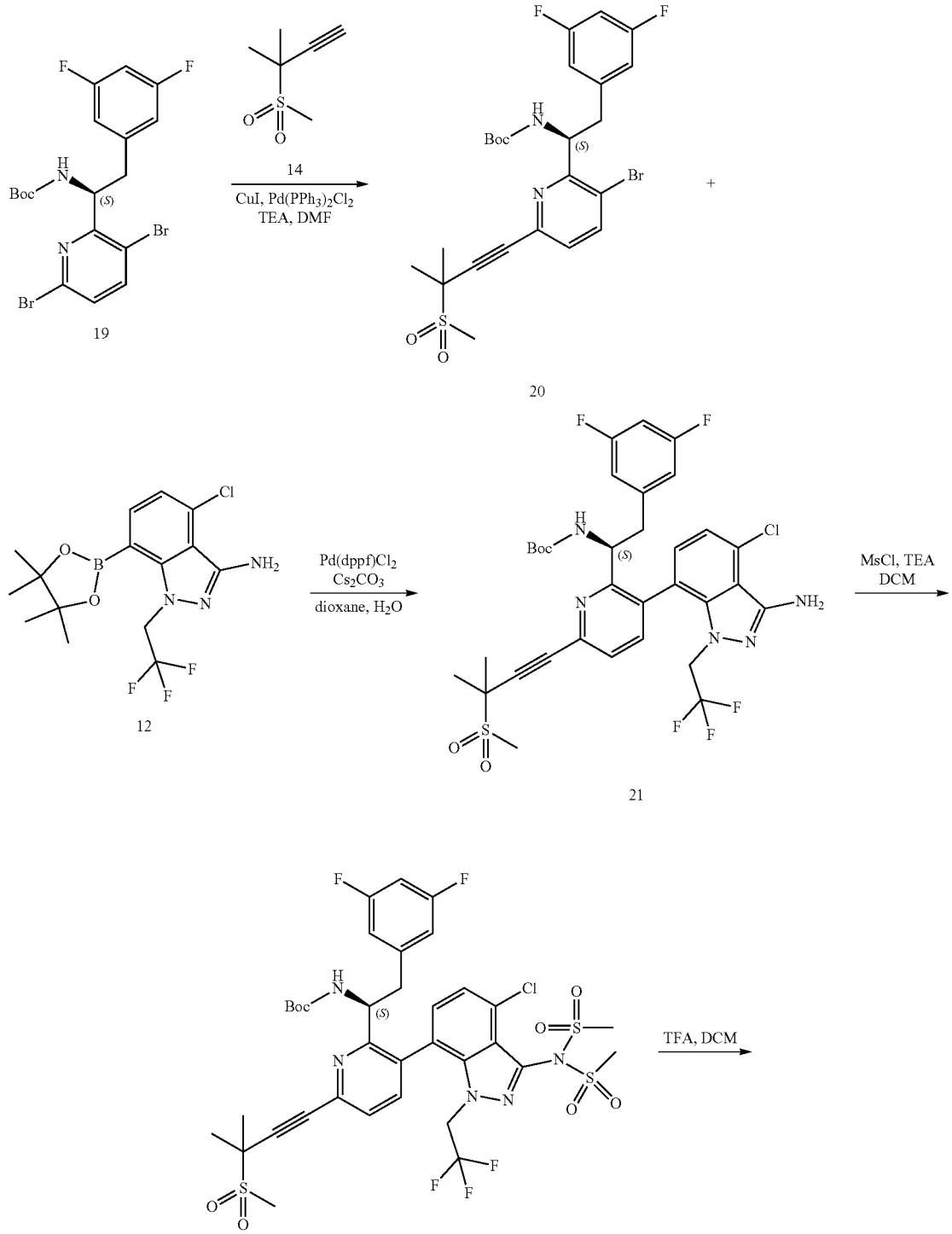

-continued

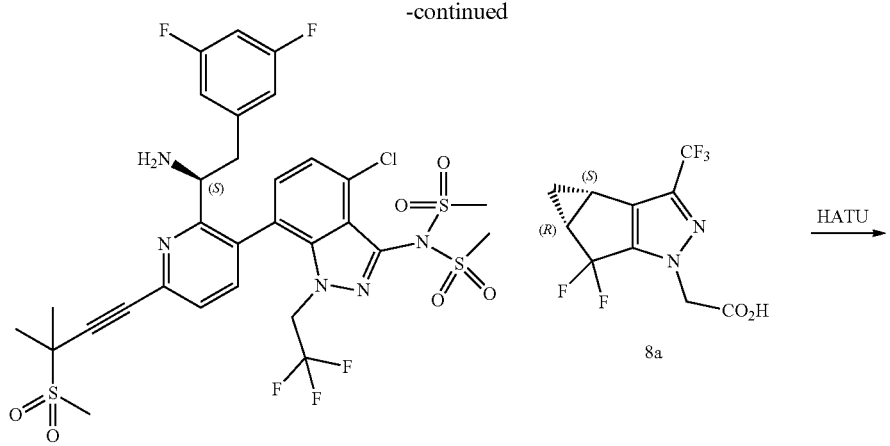

23

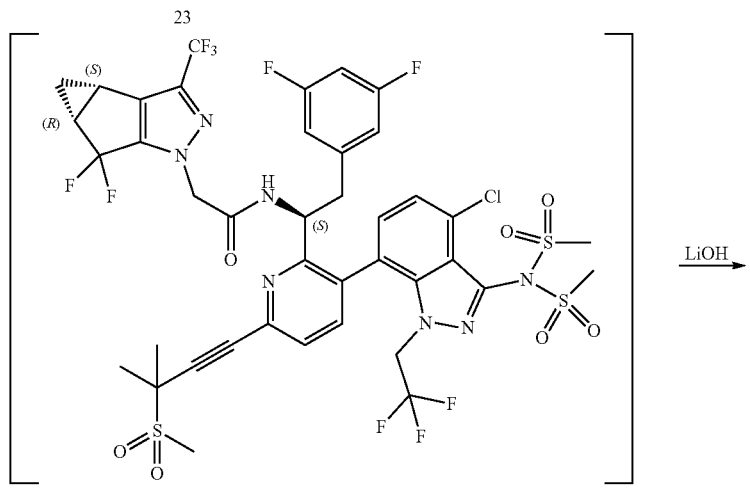

23b

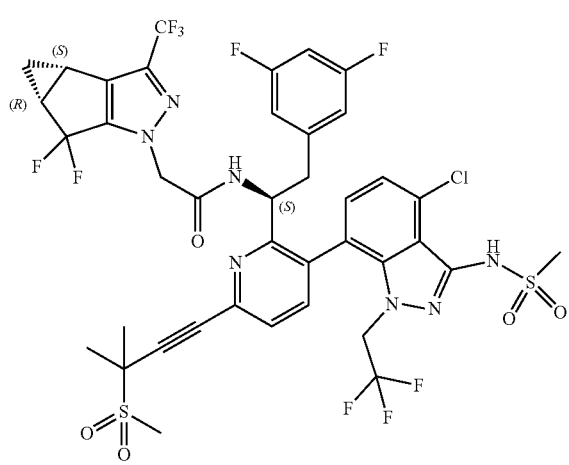

24

Synthesis of Tert-butyl (S)-(1-(3-bromo-6-(3-methyl-3-(methylsulfonyl)but-1-yn-1-yl)pyridin-2-yl)-2-(3,5-difluorophenyl)ethyl)carbamate (20)

A reactor was charged with tert-butyl (S)-(1-(3,6-dibromopyridin-2-yl)-2-(3,5-difluorophenyl)ethyl)carbamate (50.00 g, 101.8 mmol), 3-methyl-3-methylsulfonyl-but-1-yne (17.86 g, 122.2 mmol), DMF (dimethylformamide) (90 mL) and Et₃N (trimethylamine) (42.5 mL, 305.4 mmol). The reaction mixture was heated to 50° C. Bis(triphenylphosphine)palladium(II) dichloride (2.14 g, 3.1 mmol) and copper(I) iodide (0.58 g, 3.1 mmol) were added. After 30 min, the reaction mixture was diluted with MeCN (acetonitrile) (200 mL) and then 7% aq. NH₄Cl (200 mL) was added dropwise. A slurry was formed and adjusted to ambient temperature. After 3 h, the solids were collected by filtration. The cake was washed with MeCN/water (1:1, 75 mL) twice and MTBE (methyl tert-butyl ether) (75 mL). The solid was dried to provide the title compound. MS (m/z) 556 [M+H]⁺. ¹H NMR (400 MHz, Chloroform-d) δ 7.84 (d, J=8.2 Hz, 1H), 7.29-7.15 (m, 1H), 6.70-6.55 (m, 2H), 5.79 (d, J=9.0 Hz, 1H), 5.57-5.45 (m, 1H), 3.21-3.05 (m, 4H), 2.99-2.88 (m, 1H), 1.80 (s, 6H), 1.40* (s, 7H), 1.30* (s, 2H). *denotes presence of atropisomers in 4.6:1 ratio.

Synthesis of Tert-butyl (S)-(1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (21)

tert-Butyl (S)-(1-(3-bromo-6-(3-methyl-3-(methylsulfonyl)but-1-yn-1-yl)pyridin-2-yl)-2-(3,5-difluorophenyl)ethyl)carbamate (1000.0 mg, 1.79 mmol), 4-chloro-7-(4,4,5,5-tetramethyl-1,3,2-dioxaborolan-2-yl)-1-(2,2,2-trifluoroethyl)-1H-indazol-3-amine (808.5 mg, 2.15 mmol), [1,1'-bis(diphenylphosphino)ferrocene]dichloropalladium (II) (65.6 mg, 0.09 mmol), and cesium carbonate (876.7 mg, 2.69 mmol) were charged in a round bottom flask and placed under argon. Dioxane (10 mL) and water (2 mL) were added, and the suspension was degassed by bubbling argon for 60 seconds. After degassing, the reaction flask was fitted with a reflux condenser and heated to 80° C. overnight. The reaction mixture was cooled to room temperature, and the aqueous layer was removed. The organic layer was concentrated under vacuum, and the resulting residue was purified by silica gel column chromatography to provide the title compound. MS (m/z) 726.1 [M+H]⁺. ¹H NMR (400 MHz, Chloroform-d) δ 7.69-7.55 (m), 7.55-7.42 (m), 7.16-7.06 (m), 7.07-6.96 (m), 6.89 (d), 6.60 (tt), 6.44 (dd), 6.20 (d), 6.16 (d), 6.08 (s), 5.69-5.53 (m), 5.29 (s), 5.26 (d), 4.95-4.85 (m), 4.64 (q), 4.59-4.46 (m), 4.36-4.19 (m), 3.94-3.76 (m), 3.64-3.54 (m), 3.18 (s), 3.17 (s), 3.01-2.84 (m), 2.78-2.68 (m), 1.86-1.82 (m), 1.38 (s), 1.34 (s), 1.26 (s), 1.23 (s), 1.15 (s).

Synthesis of Tert-butyl (S)-(1-(3-(4-chloro-3-(N-(methylsulfonyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (22)

tert-Butyl (S)-(1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (37.89 g, 52.18 mmol) was dissolved in methylene chloride (380 mL) with stirring at ambient temperature. To it was added triethylamine (21.82 mL, 156.54 mmol) followed by slow addition of methanesulfonyl chloride (8.08 mL, 104.36 mmol). When the reaction was complete, water (200 mL) was added and stirred for 0.5 hours. The organic layer was separated and the aqueous layer was extracted with methylene chloride once. The combined organic layers were washed with water and brine, dried over MgSO₄, filtered and concentrated to a small volume. Hexanes was added. The liquid suspension was decanted. The remaining solid was dried under reduced pressure to afford the title compound. MS (m/z): 882.69 [M+H]⁺. ¹H NMR (400 MHz, Methanol-d₄) δ 7.87 (d), 7.83 (d), 7.76 (s), 7.74 (s), 7.69 (s), 7.67 (s), 7.65 (s), 7.52-7.47 (m), 7.46 (s), 7.37 (d), 7.33 (d), 7.11-7.03 (m), 4.79-4.55 (m), 4.51 (t), 4.36 (d), 4.20-4.05 (m), 3.64 (s), 3.62 (s), 3.60 (s), 3.59 (s), 3.23 (s), 3.04 (d), 3.01 (d), 2.95-2.83 (m), 1.81 (s), 1.34 (s), 1.29 (s), 0.98 (s).

Synthesis of (S)—N-(7-(2-(1-amino-2-(3,5-difluorophenyl)ethyl)-6-(3-methyl-3-(methylsulfonyl)but-1-yn-1-yl)pyridin-3-yl)-4-chloro-1-(2,2,2-trifluoroethyl)-1H-indazol-3-yl)-N-(methylsulfonyl) methanesulfonamide (23)

To tert-butyl (S)-(1-(3-(4-chloro-3-(N-(methylsulfonyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (39 g, 44 mmol) dissolved in methylene chloride (120 mL) was added trifluoroacetic acid (80 mL). The reaction mixture was stirred at ambient temperature for 50 minutes. The reaction mixture was diluted with methylene chloride and slowly poured into ice cold saturated aqueous NaHCO₃. The organic layer was separated, washed with water and brine, dried over MgSO₄, filtered and concentrated to dryness to afford the title compound. MS (m/z): 782.84 [M+H]⁻. ¹H NMR (400 MHz, Chloroform-d) δ 7.61 (d), 7.54-7.44 (m), 7.40 (d), 7.33 (d), 7.20 (d), 6.66-6.57 (m), 6.44 (d), 6.33 (d), 6.17 (d), 4.64 (s), 3.68 (s), 3.64 (s), 3.61 (s), 3.55 (s), 3.19 (s), 3.05 (dd), 2.85-2.72 (m), 1.86 (s), 1.62 (s).

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamide (24)

(S)—N-(7-(2-(1-Amino-2-(3,5-difluorophenyl)ethyl)-6-(3-methyl-3-(methylsulfonyl)but-1-yn-1-yl)pyridin-3-yl)-4-chloro-1-(2,2,2-trifluoroethyl)-1H-indazol-3-yl)-N-(methylsulfonyl)methanesulfonamide (1757 mg, 2.25 mmol), 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (666 mg, 2.36 mmol), and HATU (1-[bis(dimethylamino)methylene]-1H-1,2,3-triazolo[4,5-b]pyridinium 3-oxid hexafluorophosphate) (854 mg, 2.25 mmol) were charged in a round bottom flask and dissolved in DMF (dimethylformamide) (10.0 mL). To the solution was added N,N-diisopropylethylamine (0.80 mL, 4.49 mmol) at a rapid dropwise rate. After addition was complete, the reaction mixture was stirred at room temperature for 15 minutes to provide the intermediate 23b which was not isolated (MS (m/z) 1046.65 [M+H]⁺). To the solution was added 2N aq. sodium hydroxide solution (5.0 mL). The mixture was stirred at room temperature for 30 minutes. The reaction mixture was partitioned between water and ethyl acetate. The organic layer was collected and washed with two portions of 5% lithium chloride solution followed by brine. The organic layer was isolated, dried over sodium sulfate, filtered, and concentrated under vacuum. The resulting residue was purified by silica gel column chromatography to yield the title compound as an amorphous solid. MS (m/z) 968.24 [M+H]⁺. ¹H NMR (400 MHz, Methanol-d₄) δ 7.87-7.57 (m), 7.33-7.09 (m), 6.80-6.70 (m), 6.54 (d), 6.47 (d), 6.37-6.19 (m), 5.02-4.94 (m), 4.90-4.70 (m), 4.70-4.51 (m), 3.94 (dq), 3.32-3.28 (m), 3.23 (d), 3.07 (dd, J=13.1, 7.6 Hz), 2.93 (dd), 2.68-2.35 (m), 1.81 (s), 1.41 (q), 1.12-1.00 (m). ¹⁹F NMR (377 MHz, Methanol-d₄) δ −63.65, −71.78 (t), −72.35 (t), −82.75 (dd), −105.70 (ddd), −111.73--113.10 (m).

To more fully characterize 23b, that compound was isolated. ¹H NMR (400 MHz, DMSO-d₆) δ 9.20 (d), 8.99 (d), 7.96 (d), 7.83 (d), 7.80 (d), 7.76 (d), 7.45 (d), 7.41 (d), 7.31 (d), 7.02 (tt), 6.92 (m), 6.91 (d), 6.48 (m), 4.92 (m) 4.88 (d), 4.79 (d), 4.73 (d), 4.71 (m), 4.69 (m), 4.62 (m), 4.60 (m), 4.38 (dq), 4.12 (dq), 3.68 (s), 3.66 (s), 3.63 (s), 3.58 (s), 3.26 (s), 3.12 (dd), 3.05 (dd), 2.97 (dd), 2.78 (dd), 2.59 (m), 2.53 (m), 1.75 (s), 1.39 (m), 0.98 (m).

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic Acid (32)

Example 6

Preparation Compound 32

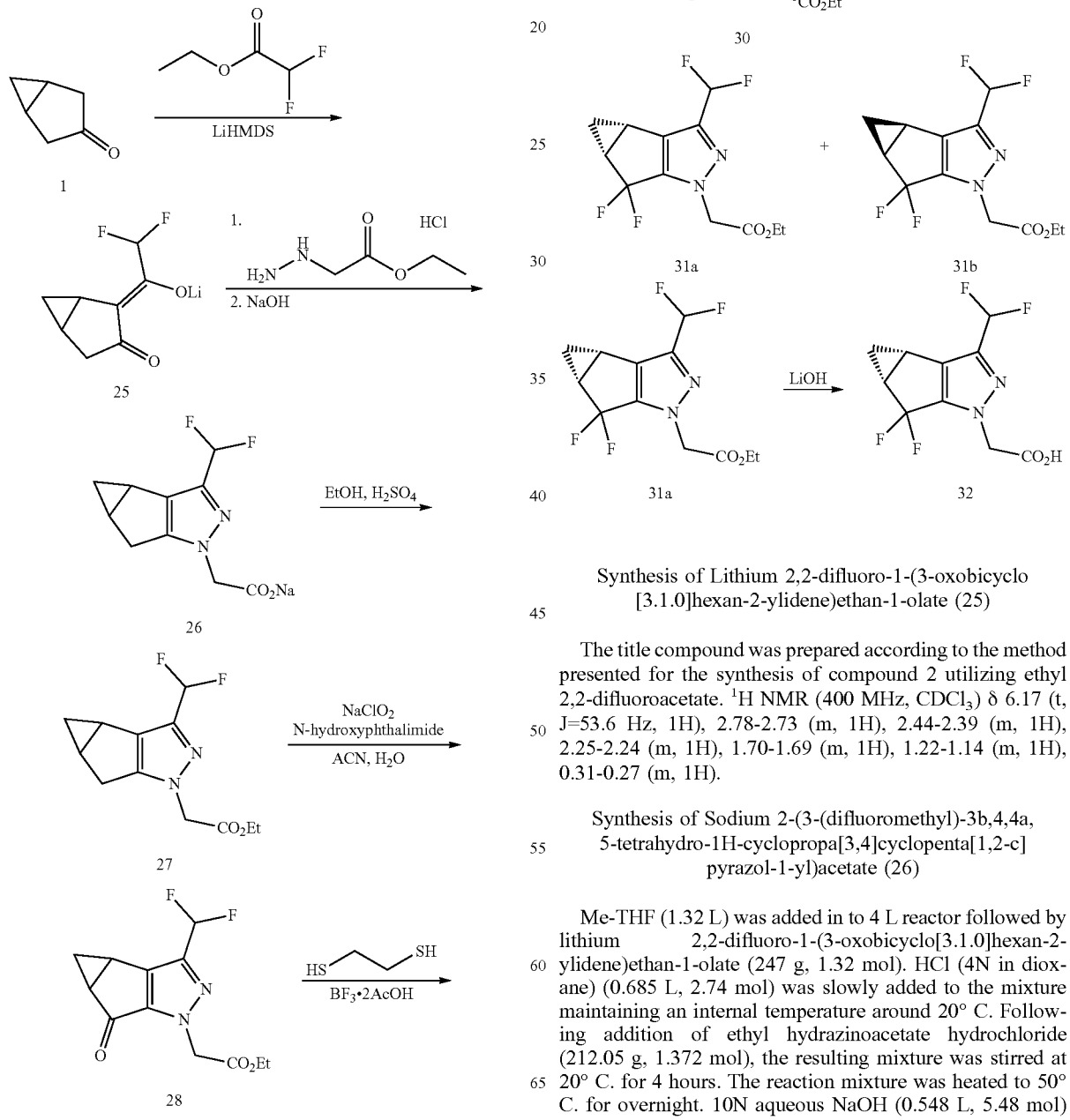

Synthesis of Lithium 2,2-difluoro-1-(3-oxobicyclo[3.1.0]hexan-2-ylidene)ethan-1-olate (25)

The title compound was prepared according to the method presented for the synthesis of compound 2 utilizing ethyl 2,2-difluoroacetate. $^1$H NMR (400 MHz, CDCl$_3$) δ 6.17 (t, J=53.6 Hz, 1H), 2.78-2.73 (m, 1H), 2.44-2.39 (m, 1H), 2.25-2.24 (m, 1H), 1.70-1.69 (m, 1H), 1.22-1.14 (m, 1H), 0.31-0.27 (m, 1H).

Synthesis of Sodium 2-(3-(difluoromethyl)-3b,4,4a,5-tetrahydro-1H-cyclopropa[3,4]cyclopenta[1,2-c]pyrazol-1-yl)acetate (26)

Me-THF (1.32 L) was added in to 4 L reactor followed by lithium 2,2-difluoro-1-(3-oxobicyclo[3.1.0]hexan-2-ylidene)ethan-1-olate (247 g, 1.32 mol). HCl (4N in dioxane) (0.685 L, 2.74 mol) was slowly added to the mixture maintaining an internal temperature around 20° C. Following addition of ethyl hydrazinoacetate hydrochloride (212.05 g, 1.372 mol), the resulting mixture was stirred at 20° C. for 4 hours. The reaction mixture was heated to 50° C. for overnight. 10N aqueous NaOH (0.548 L, 5.48 mol) was slowly added to the reaction mixture and the internal temperature was maintained at 20° C. After addition, 300 ml MeTHF was added, and the resultant suspension was stirred at 20° C. for 3 hours. The suspension was drained and filtered. The filter cake was washed with hexane (1 L) and dried in vacuum oven at 56° C. to obtain the title compound which was used directly in the next step. MS (m/z) 229.1 [M−Na+H]⁺.

Synthesis of Ethyl 2-(3-(difluoromethyl)-3b,4,4a,5-tetrahydro-1H-cyclopropa[3,4]cyclopenta[1,2-c]pyrazol-1-yl)acetate (27)

Ethyl 2-(3-(difluoromethyl)-3b,4,4a,5-tetrahydro-1H-cyclopropa[3,4]cyclopenta[1,2-c]pyrazol-1-yl)acetate from the previous step was charged in 4 L reactor and followed by the addition of EtOH (3.5 L) and concentrated $H_2SO_4$ (152 ml. 2.74 mol). The resulting mixture was stirred under reflux for 2 hours. EtOH was reduced under vacuo to 150 ml. $H_2O$ (500 ml) was added slowly. Solids were collected and washed with $H_2O$ and $NaHCO_3$, and followed by hexane (500 ml). Solid was dried under oven at 45° C. to obtain the title compound. MS (m/z) 257.1 [M+H]⁺.

Synthesis of Ethyl 2-(3-(difluoromethyl)-5-oxo-3b,4,4a,5-tetrahydro-1H-cyclopropa[3,4]cyclopenta[1,2-c]pyrazol-1-yl)acetate (28)

The title compound was prepared according to the method presented for the synthesis of compound 4 utilizing ethyl 2-(3-(difluoromethyl)-3b,4,4a,5-tetrahydro-1H-cyclopropa[3,4]cyclopenta[1,2-c]pyrazol-1-yl)acetate. MS (m/z) 271.1 [M+H]⁺.

Synthesis of Ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate (29)

To ethyl 2-(3-(difluoromethyl)-5-oxo-3b,4,4a,5-tetrahydro-1H-cyclopropa[3,4]cyclopenta[1,2-c]pyrazol-1-yl)acetate (148.5 g, 0.55 mol) in DCM (2.0 L) was added ethane-1,2-dithiol (88.0 g, 0.94 mol) in one portion followed by $BF_3 \cdot 2AcOH$ (175.8 g, 0.94 mol). The reaction was stirred at room temperature for 12 h. The system was cooled to 0° C. and quenched with saturated aqueous $NaHCO_3$ (1000 ml). The organic layer was separated, washed with brine (500 ml) and dried over $Na_2SO_4$. Solvents were removed in vacuo and the residue was purified by silica gel column chromatography to provide the title compound. MS (m/z): 347.1 [M+H]⁺.

Synthesis of Ethyl 2-(3-(difluoromethyl)-5,5-difluoro-3b,4,4a,5-tetrahydro-1H-cyclopropa[3,4]cyclopenta[1,2-c]pyrazol-1-yl)acetate (30)

A solution of DBDMH (99 g, 0.35 mol) in DCM (120 mL) was cooled to −8° C. in a teflon bottle. HF/Py (120 mL) was added drop-wise over a period of 30 min. The reaction was stirred at −78° C. for 30 min. A solution of ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate (40 g, 0.12 mol) in DCM (80 mL) was added drop-wise over a period of 15 min at −78° C. The resulting mixture was stirred for 30 min then slowly warm to −30° C. and stirred for 1.5 h. The reaction mixture was slowly poured into aq. $NaHCO_3$ (500 mL) and extracted with EA (500 mL×3). The combined organic layer was washed with 10% aq. $Na_2S_2O_3$ (500 mL), brine (500 mL) and dried over $Na_2SO_4$. Solvents were removed in vacuo to afford the crude product, which was further purified by column chromatography to provide the title compound. MS (m/z): 293.2 [M+H]⁺.

Separation of Ethyl 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetate (31a) and ethyl 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetate (31b)

Ethyl 2-(3-(difluoromethyl)-5,5-difluoro-3b,4,4a,5-tetrahydro-1H-cyclopropa[3,4]cyclopenta[1,2-c]pyrazol-1-yl)acetate was separated to its constituent enantiomers, the title compounds, by chiral HPLC under the following conditions: Column: ChiralPak AD; Mobile phase: Hex/3C EtOH=95/5; Room temperature; UV detection: 250 nm. Analytical HPLC [mobile phase: Hex/3C EtOH=95/5; Flow rate: 0.75 mL/min; Column: Chiralpak AD-H, 150×4.6 mm, 5 um; Wavelength: 220 nm] 31a: t=5.30 min, 31b: t=7.00 min.

Compound 31a—¹H NMR (400 MHz, Chloroform-d) δ 6.63 (t, J=54.8 Hz, 1H), 4.83 (s, 2H), 4.24 (q, J=7.2 Hz, 2H), 2.48-2.45 (m, 2H), 1.38-1.36 (m, 1H), 1.28 (t, J=7.2 Hz, 3H), 1.13-1.12 (m, 1H).

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic Acid (32)

To a solution of ethyl 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetate (26 g, 89.0 mmol) in THF (180 mL), MeOH (90 mL) and water (90 mL) was added LiOH (5.13 g, 213.5 mmol). The mixture was stirred for 4 h. The mixture was concentrated to remove most of THF and MeOH, the aqueous was acidified by 1N HCl to adjust pH to 2-3, then extracted with EA (600 mL×2). The organic phase was separated and combined, dried over $Na_2SO_4$, filtered and concentrated in vacuum to provide the title compound. MS (m/z) 265.0 [M+H]⁺.

Example 7

Preparation of Compound 34

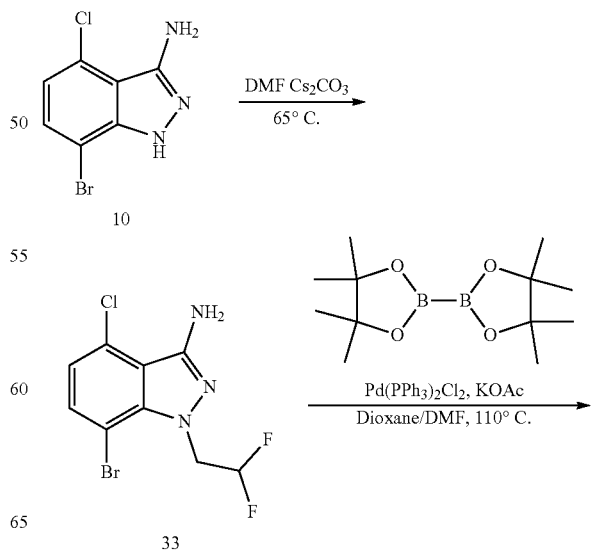

Synthesis of 4-chloro-1-(2,2-difluoroethyl)-7-(4,4,5,5-tetramethyl-1,3,2-dioxaborolan-2-yl)-1H-indazol-3-amine (34)

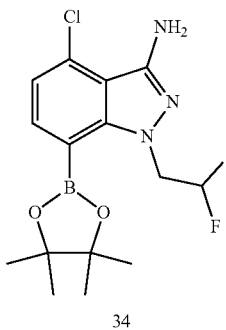

34

Synthesis of 7-bromo-4-chloro-1-(2,2-difluoroethyl)-1H-indazol-3-amine (33)

To a 2000-mL 4-necked round-bottom flask was placed 7-bromo-4-chloro-1H-indazol-3-amine (130 g, 527.40 mmol, 1.00 equiv), N,N-dimethylformamide (1300 mL), Cs₂CO₃ (260 g, 797.99 mmol, 1.50 equiv) with stirring for 20 min, followed by the addition of 1,1-difluoro-2-iodoethane (122 g, 635.59 mmol, 1.20 equiv). The resulting mixture was stirred overnight at 65° C., then cooled to room temperature, quenched by the addition of 3 L of water/ice, extracted with 3×1.5 L of ethyl acetate. The combined organic layer was washed with 1×1.5 L of H₂O, 1×1.5 L of brine, dried over anhydrous sodium sulfate, concentrated under vacuum, and recrystallized from ethanol to afford the title compound. MS (m/z) 312.1 [M+H]⁺.

To a 3000-mL 4-necked round-bottom flask purged and maintained with an inert atmosphere of nitrogen was placed 7-bromo-4-chloro-1-(2,2-difluoroethyl)-1H-indazol-3-amine (80 g, 257.63 mmol, 1.00 equiv), 1,4-dioxane (800 mL), N,N-dimethylformamide (800 mL), KOAc (76 g, 774.40 mmol, 3.00 equiv), 4,4,5,5-tetramethyl-2-(tetramethyl-1,3,2-dioxaborolan-2-yl)-1,3,2-dioxaborolane (197 g, 775.78 mmol, 3.00 equiv) and Pd(PPh₃)₂Cl₂ (8 g, 11.40 mmol, 0.04 equiv). The mixture was stirred for 4 h at 110° C., then cooled to room temperature, quenched by the addition of 5 L of water/ice, extracted with 2×2 L of ethyl acetate. The combined organic layer was washed with 1×1 L of H₂O, 1×1 L of brine, dried over anhydrous sodium sulfate and concentrated under vacuum. The residue was applied onto a silica gel column eluted with ethyl acetate/petroleum ether (1:10) to afford the title compound. MS (m/z): 358 [M+H]⁺. ¹H-NMR: (DMSO-d6, 300 MHz, ppm): δ7.63-7.66 (1H, d), 7.00-7.03 (1H, d), 6.06-6.43 (1H, t), 5.46 (2H, s), 4.90-5.01 (2H, t), 1.34 (12H, s).

Example 8

Preparation of Formula (IIb) (Compound 38)

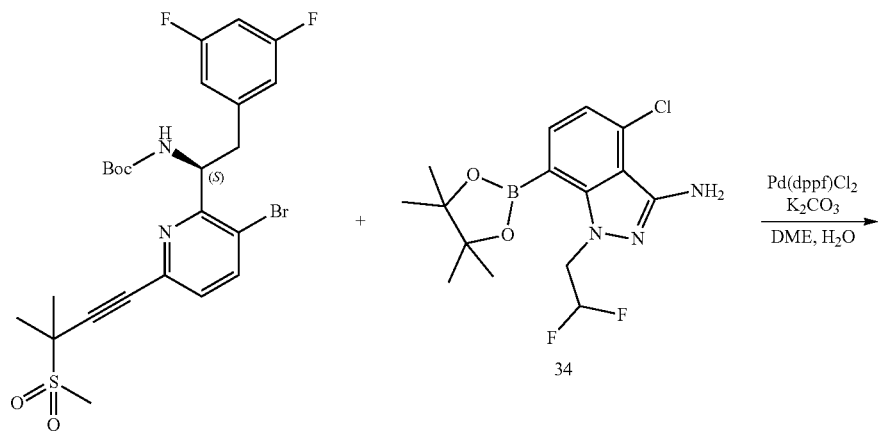

20

-continued
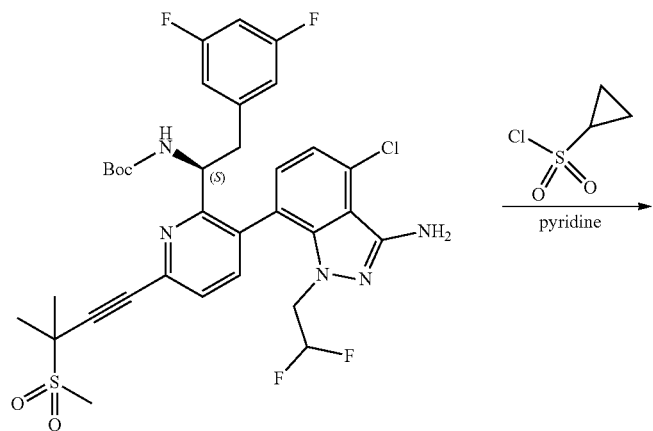
35
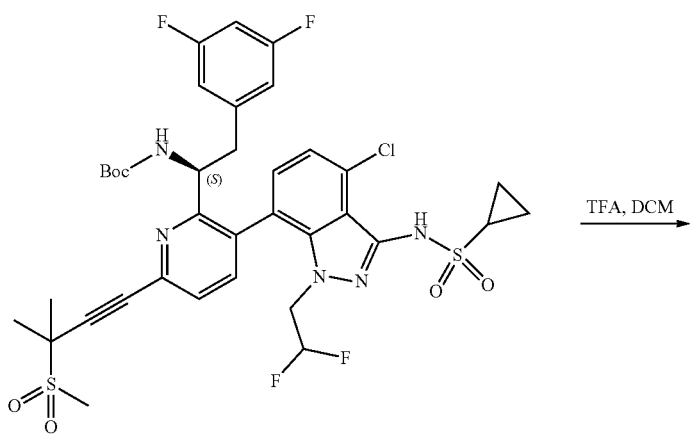
36
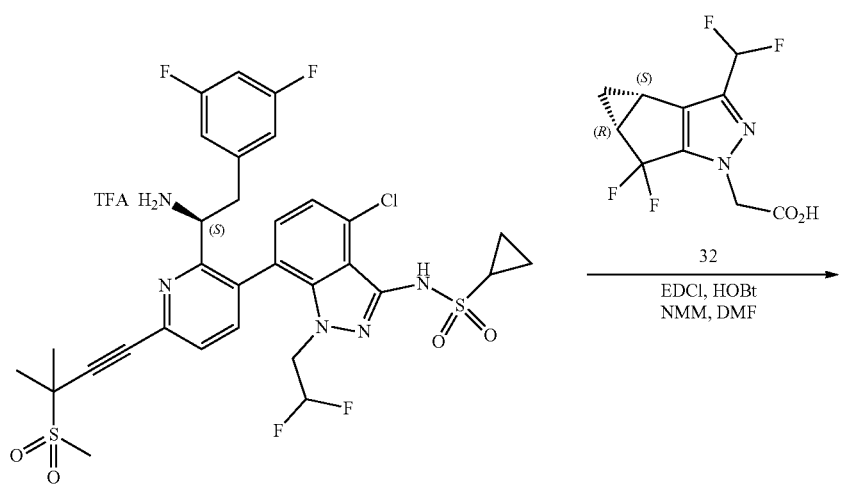
37

-continued

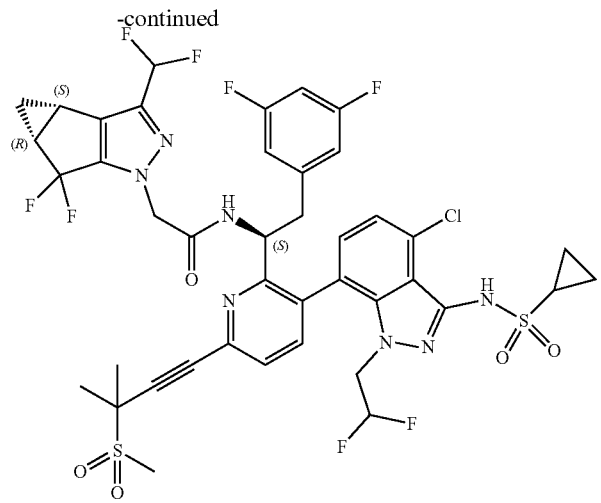

38

Synthesis of Tert-butyl (S)-(1-(3-(3-amino-4-chloro-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (35)

tert-Butyl (S)-(1-(3-bromo-6-(3-methyl-3-(methylsulfonyl)but-1-yn-1-yl)pyridin-2-yl)-2-(3,5-difluorophenyl) ethyl)carbamate (300 mg, 0.53 mmol), 4-chloro-1-(2,2-difluoroethyl)-7-(4,4,5,5-tetramethyl-1,3,2-dioxaborolan-2-yl)-1H-indazol-3-amine (250 mg, 0.7 mmol), [1,1'-bis(diphenylphosphino)ferrocene]dichloropalladium(II) (14 mg, 0.016 mmol), and potassium carbonate (186 mg, 1.35 mmol) were charged in a microwave tube and placed under argon. Dimethoxyethane (2.5 mL) and water (0.3 mL) were added, and the reaction mixture was heated to 130° C. in a microwave reactor (Biotage® Initiator+) for 7 minutes. The reaction mixture was cooled to room temperature, and partitioned between EtOAc and 0.1 N HCl. The aqueous layer was removed and the organic layer was concentrated under vacuum. The resulting residue was purified by silica gel column chromatography to provide the title compound. MS (m/z) 708.20 [M+H]$^+$). $^1$H NMR (400 MHz, Methanol-d4) δ 7.91-7.50 (m), 7.28-6.89 (m), 6.88-6.65 (m), 6.56 (dd), 6.46-6.17 (m), 6.08-5.60 (m), 4.76-4.47 (m), 4.04-3.73 (m), 3.73-3.41 (m), 3.22 (s), 3.17-2.69 (m), 1.80 (s), 1.29 (d), 0.98 (d).

Synthesis of Tert-butyl (S)-(1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl) carbamate (36)

tert-Butyl (S)-(1-(3-(3-amino-4-chloro-1-(2,2-difluoroethyl)-1H-indazol-7-yl)-6-(3-methyl-3-(methylsulfonyl) but-1-yn-1-yl)pyridin-2-yl)-2-(3,5-difluorophenyl)ethyl) carbamate (700 mg, 0.99 mmol) and 4-dimethylaminopyridine (24 mg, 0.2 mmol) were dissolved in pyridine (2 mL) with stirring at ambient temperature. To it was added cyclopropane-1-sulfonyl chloride (222 µL, 2.2 mmol). The reaction mixture was stirred at 70° C. until the reaction was complete. Water was added and stirred for 1 hour, and the resulting precipitate was collected by vacuum filtration then dissolved in methylene chloride, dried over MgSO$_4$, filtered and concentrated. The residue was purified by silica chromatography to afford the title compound. MS (m/z): 812.44 [M+H]$^+$. $^1$H NMR (400 MHz, Methanol-d4) δ 7.93-7.58 (m), 7.50-7.15 (m), 7.00 (dd), 6.82-6.51 (m), 6.47-6.29 (m), 6.18-5.65 (m), 4.77-4.43 (m), 4.31-4.08 (m), 3.99-3.63 (m), 3.22 (s), 3.18-2.71 (m), 1.80 (s), 1.28 (s), 1.20-0.76 (m).

Synthesis of (S)—N-(7-(2-(1-amino-2-(3,5-difluorophenyl)ethyl)-6-(3-methyl-3-(methylsulfonyl)but-1-yn-1-yl)pyridin-3-yl)-4-chloro-1-(2,2-difluoroethyl)-1H-indazol-3-yl)cyclopropanesulfonamide (37)

To a solution of tert-butyl (S)-(1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (705 mg, 0.87 mmol) in methylene chloride (5 mL) was added trifluoroacetic acid (3 mL). The reaction mixture was stirred for 1 hour then slowly poured into a saturated sodium bicarbonate solution. It was extracted with EtOAc. Organic layer was separated, washed with brine, dried over MgSO$_4$, filtered and concentrated to afford the title compound. MS (m/z): 712.34 [M+H]+. $^1$H NMR (400 MHz, Methanol-d4) δ 7.93-7.58 (m), 7.50-7.15 (m), 7.00 (dd), 6.82-6.51 (m), 6.47-6.29 (m), 6.18-5.65 (m), 4.77-4.43 (m), 4.31-4.08 (m), 3.99-3.63 (m), 3.22 (d), 3.18-2.71 (m), 1.80 (d), 1.28 (s), 1.20-0.76 (m).

Synthesis of N—((S)-1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl) pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c] pyrazol-1-yl)acetamide (38)

(S)—N-(7-(2-(1-amino-2-(3,5-difluorophenyl)ethyl)-6-(3-methyl-3-(methylsulfonyl)but-1-yn-1-yl)pyridin-3-yl)-4-chloro-1-(2,2-difluoroethyl)-1H-indazol-3-yl)cyclopropanesulfonamide (514 mg, 0.72 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (191 mg, 0.72 mmol), 1-hydroxybenzotriazole (49 mg, 0.36 mmol) and 1-(3-dimethylaminopropyl)-3-ethylcarbodiimide hydrochloride (180 mg, 0.94 mmol) were charged in a round bottom flask and dissolved in DMF (10 mL). n-Methylmorpholine (0.20 mL, 1.8 mmol) was added. The reaction mixture was stirred at ambient temperature for 30 minutes. Water was added and stirred for 1 hour. The resulting precipitate was collected by vacuum filtration then dissolved in methylene chloride, dried over $MgSO_4$, filtered and concentrated. The residue was purified by RP-HPLC to yield the title compound as a TFA salt. MS (m/z) 958.88 $[M+H]^+$. $^1$H NMR (400 MHz, Methanol-d4) δ 7.90-7.56 (m), 7.30-7.07 (m), 6.91-6.54 (m), 6.54-6.39 (m), 6.37-6.21 (m), 6.16-5.70 (m), 4.85-4.57 (m), 4.34-4.12 (m), 3.87-3.41 (m), 3.23 (s), 3.17-3.02 (m), 3.00-2.77 (m), 2.57-2.37 (m), 1.81 (s), 1.50-0.84 (m).

BIOLOGICAL EXAMPLES

Example A

Test A: Antiviral Assay in MT4 Cells

For the antiviral assay, 0.4 µL of 189× test concentration of 3-fold serially diluted compound in DMSO was added to 40 µL of cell growth medium (RPMI 1640, 10% FBS, 1% Penicillin-Streptomycin, 1% L-Glutamine, 1% HEPES) in each well of 384-well plate (10 concentrations) in quadruplicate.

1 mL Aliquots of MT4 cells were pre-infected for 3 hours at 37° C. with 25 µL of cell growth medium (mock-infected) or a fresh 1:250 dilution of an HIV-IIIb concentrated ABI stock (0.004 m.o.i.). Infected and uninfected cells were diluted in cell growth media and 35 µL (2000 cells) was added to each well of the assay plates.

Assay plates were then maintained in a humidified, 5% $CO_2$ incubator at 37° C. After 5 days of incubation, 25 µl of 2× concentrated CellTiter-Glo™ Reagent (catalog #G7573, Promega Biosciences, Inc., Madison, Wis.) was added to each well of the assay plate. Cell lysis was carried out by incubating at room temperature for 10 minutes and then chemiluminescence was read using an Envision plate reader (PerkinElmer). $EC_{50}$ values were calculated as the compound concentration that caused a 50% decrease in luminescence signal, a measure of HIV-1 replication.

Example B

Test B: Cytotoxicity Assay

Compound cytotoxicity and the corresponding $CC_{50}$ values was determined using the same protocol as described in the antiviral assay (Test A) except that uninfected cells were used. The compound of the present disclosure demonstrates antiviral activity (Test A) as depicted in the table below in comparison to Compound A and Compound B.

| Compound | $EC_{50}$ (nM) | $CC_{50}$ (nM) |
|---|---|---|
| Compound 24 | 0.185 | 30068 |
| Compound 38 | 0.399 | 55218 |
| Compound A | 1.715 | 21839 |
| Compound B | 2.991 | 14491 |

Example C

Test C. Pharmacokinetic Analysis Following Intravenous Administration to Sprague-Dawley Rats and Beagle Dogs and Cynomologous Monkeys Test Article and Formulation Compound 24 and 38 IV administration was formulated in 5% ethanol, 20% PG, 45% PEG 300, 30% pH 2 (0.01N HCl) water at 0.5 mg/mL. Compound A and Compound B intravenous infusion doses were formulated in a sterile solution of 5% ethanol, 45% PEG 400 and 50% water (pH 2.0) at 0.5 mg/mL. All IV formulations were in solution.

Animals Used

Each rat IV dosing group consisted of 3 male SD rats. At dosing, the animals generally weighed between 0.317 and 0.355 kg. The animals were fasted overnight prior to dose administration and up to 4 hr after dosing. Each dog IV dosing group consisted of 3 male, naïve beagle dogs. At dosing, the animals weighed ~10-12 kg. The animals were fasted overnight prior to dose administration and up to 2 hr after dosing.

Each cynomolgus (cyno) monkey IV dosing group consisted of 3 male, naïve cyno monkeys At dosing, the animals weighed ~3.2-4 kg. The animals were fasted overnight prior to dose administration and up to 2 hr after dosing.

Dosing

For the IV infusion group, the test compound was administered by intravenous infusion over 30 minutes. The rate of infusion was adjusted according to the body weight of each animal to deliver a dose of 1 mg/kg at 2 mL/kg.

Sample Collection

Serial venous blood samples (approximately 0.4 mL each for rat and 1.0 mL for dog) were taken at specified time points after dosing from each animal. The blood samples were collected into Vacutainer™ tubes (Becton-Dickinson Corp, New Jersey, USA) containing EDTA as the anticoagulant and were immediately placed on wet ice pending centrifugation for plasma. Centrifugation began within 1 hour of collection. All samples were placed into 96-well tubes and maintained on dry ice prior to storage at approximately −70° C.

Determination of the Concentrations of the Compound of Formula (I) in Plasma

An LC/MS/MS method was used to measure the concentration of test compounds in plasma.

Calculations

Non-compartmental pharmacokinetic analysis was performed on the plasma concentration-time data. A summary of pharmacokinetic parameters are shown in the tables below.

| Compound | Rat CL (L/h/kg) | Rat $V_{ss}$ (L/kg) | Rat $t_{1/2}$ (h) | Dog CL (L/h/kg) | Dog $V_{ss}$ (L/kg) | Dog $t_{1/2}$ (h) | Cyno CL (L/h/kg) | Cyno $V_{ss}$ (L/kg) | Cyno $t_{1/2}$ (h) |
|---|---|---|---|---|---|---|---|---|---|
| Compound 24 | 0.05 | 1.8 | 28 | 0.07 | 1.6 | 22 | 0.24 | 2.7 | 12 |
| Compound 38 | 0.08 | 1.8 | 19 | 0.33 | 1.77 | 7 | 0.21 | 2.1 | 9.5 |
| Compound A | 0.50 | 1.0 | 2 | 0.25 | 0.8 | 4 | 0.45 | 1.18 | 2.3 |
| Compound B | 0.43 | 1.4 | 3 | 0.28 | 1.3 | 6 | 0.42 | 1.59 | 3.4 |

CL observed clearance;
$V_{ss}$ volume of distribution at steady state;
$t_{1/2}$ terminal half-life

| Compound | Rat $C_{max}$ | Rat $AUC_{inf}$ (μM · h) | Dog $C_{max}$ | Dog $AUC_{inf}$ (μM · h) | Cyno $C_{max}$ | Cyno $AUC_{inf}$ (μM · h) |
|---|---|---|---|---|---|---|
| Compound 24 | 1.8 | 19 | 2.2 | 14.8 | 1.3 | 4.5 |
| Compound 38 | 2.4 | 13 | 1.6 | 3.3 | 1.3 | 4.9 |
| Compound A | 1.4 | 2.7 | 2.1 | 5 | 1.8 | 2.6 |
| Compound B | 1.1 | 2.7 | 1.4 | 4.3 | 1.4 | 2.9 |

$AUC_{inf}$ Area Under the Curve from t = 0 to infinity;
$C_{max}$ Maximum plasma concentration Example D Test D. Metabolic Stability in Cultured Human Liver Hepatocytes Radiolabelled test compounds, wherein tritium was introduced into the structure in place of one or more hydrogens, were prepared according to known methods in the art.

The radiolabelled compounds were incubated in pooled cryopreserved hepatocytes at a substrate concentration of 0.25 μM and radioactivity concentration of 10 uCi/mL. The final hepatocyte concentration was 1 million cells/mL. The hepatocyte/compound reaction mixture was dissolved in InVitroGRO™ KHB buffer (catalog #Z99074, BioreclamationIVT, Inc., Baltimore, Md.) at pH 7.4. The incubations were performed in duplicate. A cell free control and a positive control were included in the incubations. The incubations were carried out with gentle shaking in a 37° C. incubator under a humid atmosphere of 95% air/5% $CO_2$ (v/v). Aliquots (100 mL) were removed after 0, 1, 3, and 6 hours and added to 200 mL quenching solution that comprised 0.1% (v/v) TFA in 5% water/95% acetonitrile (v/v). The samples were placed on a shaker for 10 min, followed by centrifugation at 3000 g for 30 min. The samples of the supernatant were analyzed on a Dionex HPLC/PerkinElmer Flow Scintillation Analyzer as described below.

Liquid Chromatography-Radiochromatography

Quantification was done by comparison of radiolabeled metabolites and parent peaks measured on a Radiomatic 625TR Flow Scintillation Analyzer coupled to a Dionex/Chromeleon chromatography system. The column was a Phenomenex Synergi fusion RP (150×4.6 mm, 4 mm) maintained at 32 degrees Celsius. Mobile Phase A consisted of 0.1% (v/v) TFA in 99% water/1% acetonitrile (v/v). Mobile Phase B consisted of 0.1% (v/v) TFA in 5% water/95% acetonitrile (v/v). The flow rate was 1 mL/min using a sample injection volume of 100 mL. Gradient was as following: Mobile phase B was linearly increased from to 75% over 47 min, maintained at 75% for 3 min, changed back to 2%, maintained at 2% for 10 min.

Metabolic stability was determined by measuring the change in relative abundance of metabolites and parent over time and calculating from it the rate of disappearance of the parent compound. The stability data was utilized to calculate predicted human hepatic clearance values according to methods known in the art. The predicted human hepatic clearance values are shown in the table below.

| | Predicted Human Hepatic Clearance (L/hr/kg) |
|---|---|
| Compound 24 | 0.01 |
| Compound 38 | 0.02 |
| Compound A | 0.09 |
| Compound B | 0.04 |

The following can be deduced from the above comparative data:

Compound 24 is more potent in an HIV antiviral assay relative to compounds A and B (about 9 and about 16 times more potent, respectively). Compound 24 has a longer in vivo terminal half-life in rat relative to compounds A and B (about 14 and about 9 times longer, respectively). Compound 24 has a lower in vivo clearance in rat relative to compounds A and B (about 10 and about 8.6 times lower, respectively). Compound 24 has a longer in vivo terminal half-life in dog relative to compounds A and B (about 5 and about 4 times longer, respectively). Compound 24 has a lower in vivo clearance in dog relative to compounds A and B (about 3 and about 4 times lower, respectively). Compound 24 is more stable in human hepatocytes with a lower predicted hepatic clearance relative to compounds A and B (about 9 and about 4 times more stable, respectively).

The above data demonstrate that compound 24, has improved antiviral potency and an improved pharmacokinetic profile (which is demonstrated by longer half-life in rat and dog and lower predicted human clearance) when compared to compounds A and B.

Additionally, compound 38 is more potent in an HIV antiviral assay relative to compounds A and B (about 4 and about 8 times more potent, respectively). Compound 38 has a longer in vivo terminal half-life in rat relative to compounds A and B (about 9.5 and about 6.3 times longer, respectively). Compound 38 has a lower in vivo clearance in rat relative to compounds A and B (about 6.3 and about 5.4 times lower, respectively). Compound 38 has a similar in vivo clearance and terminal half-life in dog compared to compounds A and B. Compound 38 is more stable in human hepatocytes with a lower predicted hepatic clearance relative to compounds A and B (about 4.5 and about 2 times more stable, respectively).

The above data demonstrate that compound 38, has improved antiviral potency and an improved pharmacokinetic profile (which is demonstrated by longer half-life in rat and dog and lower predicted human clearance) when compared to compounds A and B.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

The Examples disclosed herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

Formulation Example

Figure 3:
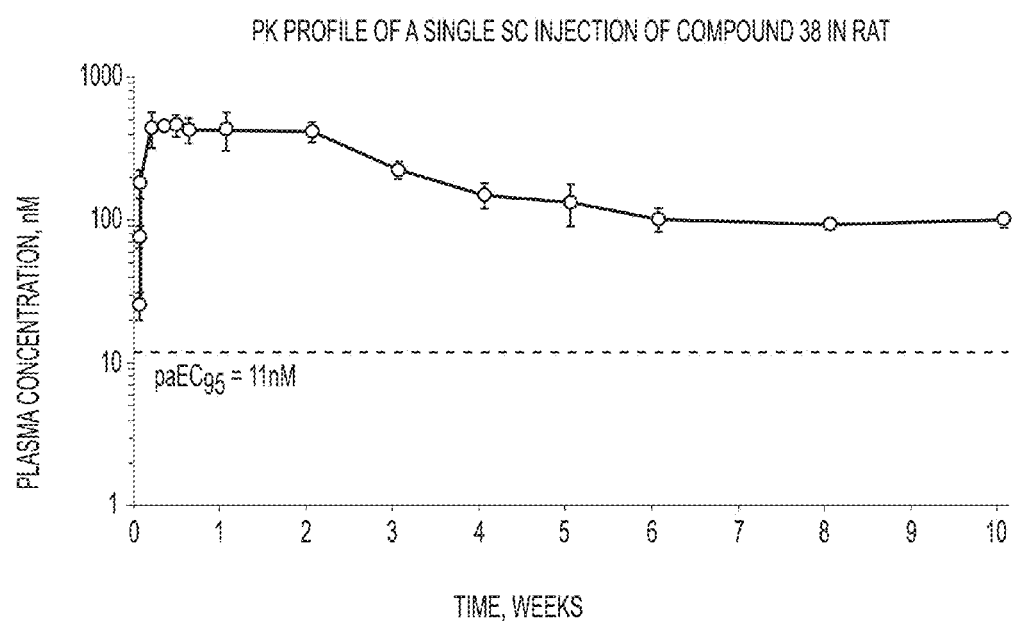
FIG. 3 shows the plasma concentration (nM) of Compound 38 after a single subcutaneous (SC) dose in rats.

Compound 38 (about 30 mg/kg) was formulated as an aqueous suspension in 2% poloxamer 338 in saline (about 150 mg/mL). This formulation was then administered as a single subcutaneous (SC) injection to rats and the pharmacokinetic (PK) profile was determined. As can be seen in FIG. 3, Compound 38 maintains plasma concentrations well above paEC95 for >10 weeks from a single SC injection. This data demonstrates that Compound 38 displays extended release pharmacokinetics.

Figure 4:
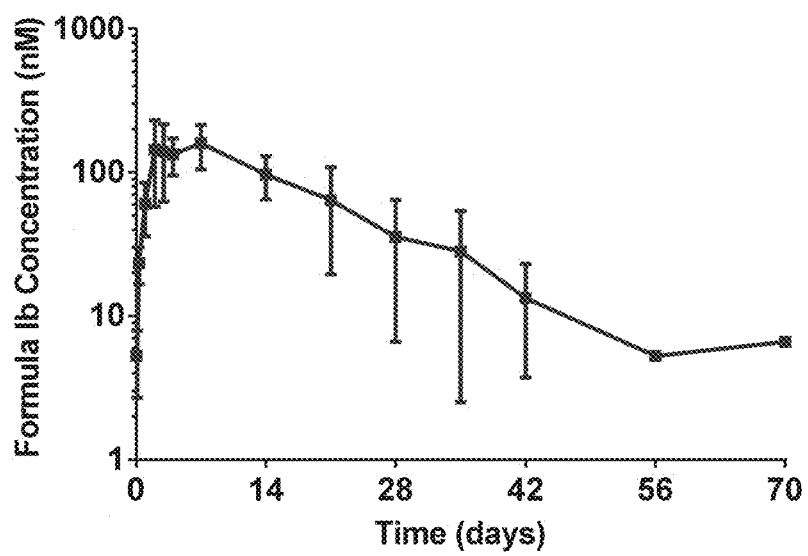
FIG. 4 shows a plot of plasma concentration over time of 200 mg/mL of Formula Ib in 2% poloxamer 188 in saline when subcutaneously dosed in dogs at 6 mg/kg.

A suspension of a compound of Formula Ib in 2% poloxamer 188 in saline (200 mg/mL) was prepared. The suspension was administered to dogs subcutaneously at a dose of 6 mg/kg and the pharmacokinetic (PK) profile was determined. FIG. 4 shows a plot of the plasma concentration of the compound of Formula Ib as a function of time. As the data shows in FIG. 4, the compound of Formula Ib has measurable plasma concentrations at day 70 demonstrating extended release pharmacokinetics.

Figure 5:
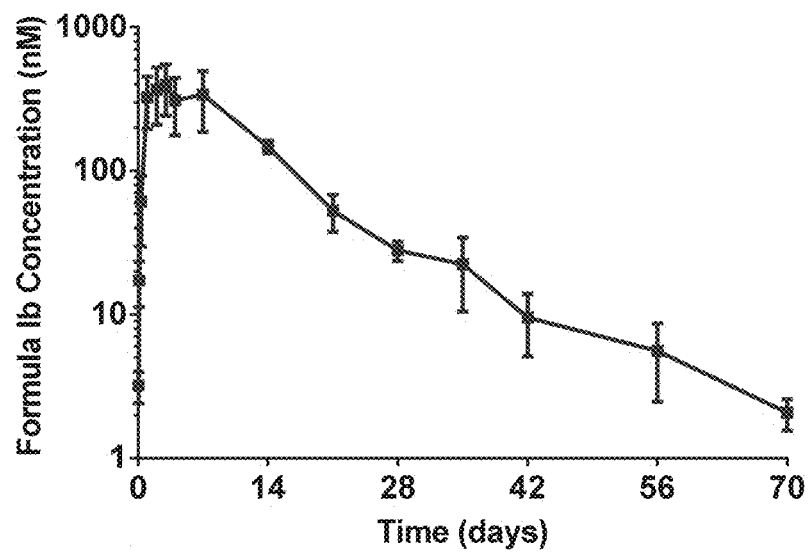
FIG. 5 shows a plot of plasma concentration over time of 100 mg/mL of Formula Ib in 2% poloxamer 188 in saline when subcutaneously dosed in dogs at 6 mg/kg.

A suspension of a compound of Formula Ib in 2% poloxamer 188 in saline (100 mg/mL) was prepared. The suspension was administered to dogs subcutaneously at a dose of 6 mg/kg and the pharmacokinetic (PK) profile was determined. FIG. 5 shows a plot of the plasma concentration of the compound of Formula Ib as a function of time. As the data shows in FIG. 5, the compound of Formula Ib has measurable plasma concentrations at day 70 demonstrating extended release pharmacokinetics.

Figure 6:
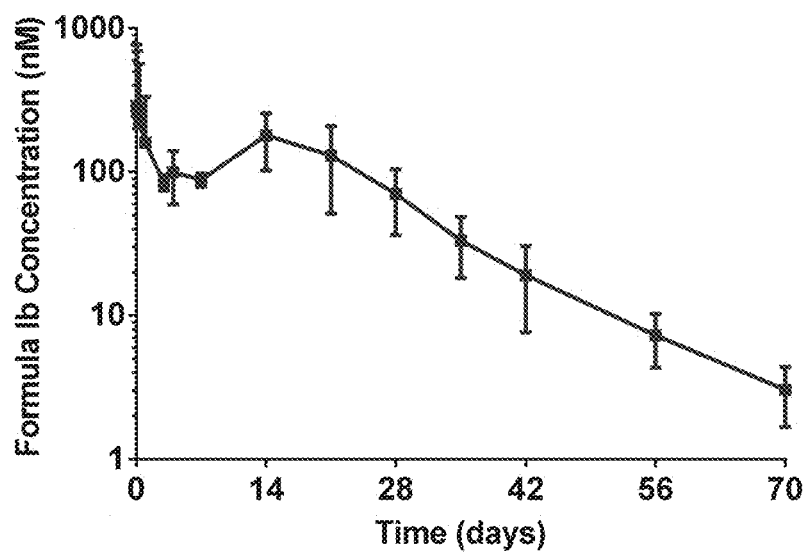
FIG. 6 shows a plot of plasma concentration over time of 200 mg/mL of Formula Ib, sodium salt in 2% poloxamer 188 in saline when subcutaneously dosed in dogs at 6 mg/kg.

A suspension of the sodium salt of a compound of Formula Ib in 2% poloxamer 188 in saline (200 mg/mL) was prepared. The suspension was administered to dogs subcutaneously at a dose of 6 mg/kg and the pharmacokinetic (PK) profile was determined. FIG. 6 shows a plot of the plasma concentration of the compound of Formula Ib as a function of time. As FIG. 6 shows, the compound of Formula Ib has measurable plasma concentrations at day 70 demonstrating extended release pharmacokinetics.

Figure 7:
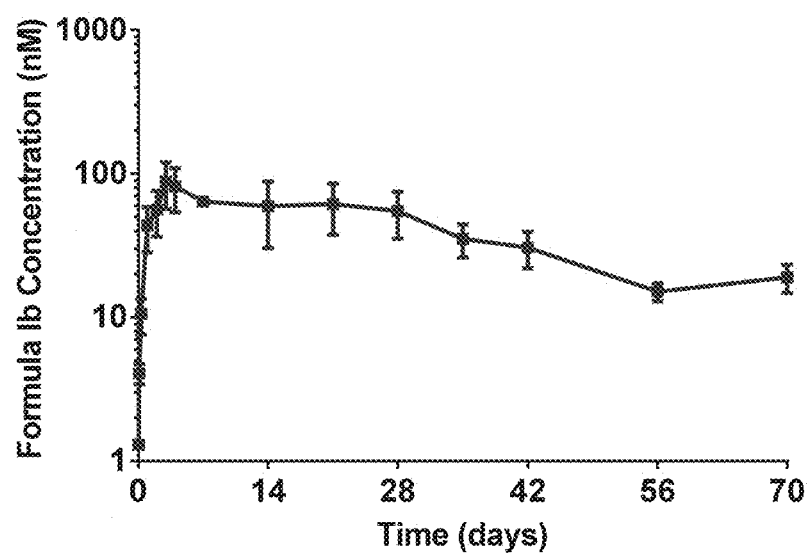
FIG. 7 shows a plot of plasma concentration over time of 100 mg/mL of Formula Ib, free acid form in NMP when subcutaneously dosed in dogs at 6 mg/kg.

A solution of a compound of Formula Ib in NMP (100 mg/mL) was prepared. The solution was administered to dogs subcutaneously at a dose of 6 mg/kg and the pharmacokinetic (PK) profile was determined. FIG. 7 shows a plot of the plasma concentration of the compound of Formula Ib as a function of time. As the data shows in FIG. 7, the compound of Formula Ib has measurable plasma concentrations at day 70 demonstrating extended release pharmacokinetics.

Figure 8:
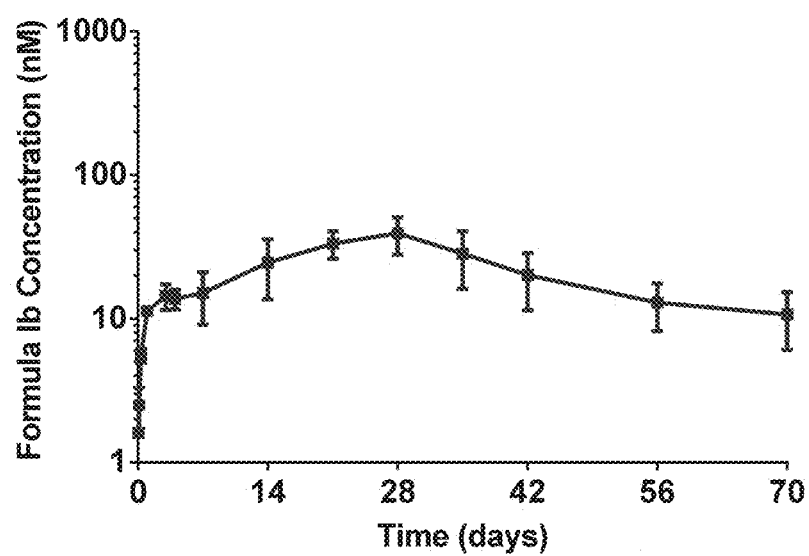
FIG. 8 shows a plot of plasma concentration over time of 200 mg/mL of Formula Ib, free acid form in NMP when subcutaneously dosed in dogs at 6 mg/kg.

A solution of a compound of Formula Ib in NMP (200 mg/ml) was prepared. The solution was administered to dogs subcutaneously at a dose of 6 mg/kg and the pharmacokinetic (PK) profile was determined. FIG. 8 shows a plot of the plasma concentration of the compound of Formula Ib as a function of time. As the data shows in FIG. 8, the compound of Formula Ib has measurable plasma concentrations at day 70 demonstrating extended release pharmacokinetics.

Figure 9:
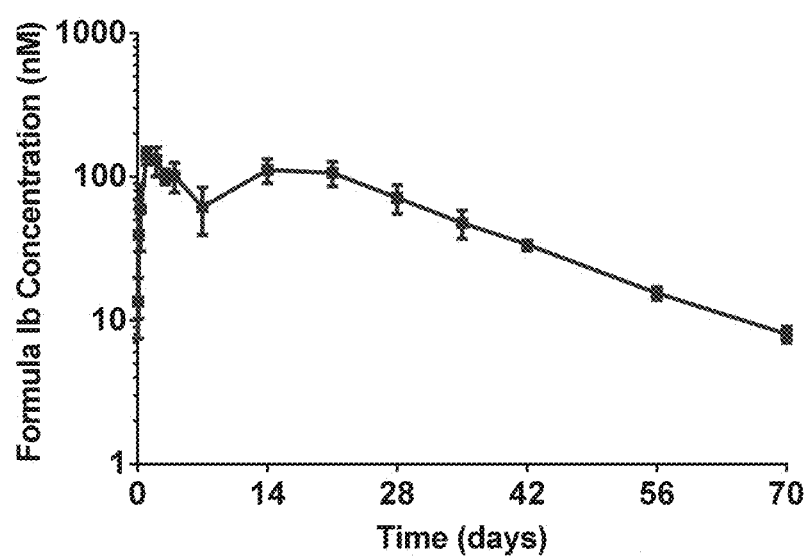
FIG. 9 shows a plot of plasma concentration over time of 200 mg/mL of Formula Ib, sodium salt in NMP when subcutaneously dosed in subjects at 6 mg/kg.

A solution of the sodium salt of a compound of Formula Ib in NMP (200 mg/ml) was prepared. The solution was administered to dogs subcutaneously at a dose of 6 mg/kg and the pharmacokinetic (PK) profile was determined. FIG. 9 shows a plot of the plasma concentration of the compound of Formula Ib as a function of time. As the data shows in FIG. 9, the compound of Formula Ib has measurable plasma concentrations at day 70 demonstrating extended release pharmacokinetics.

Figure 10:
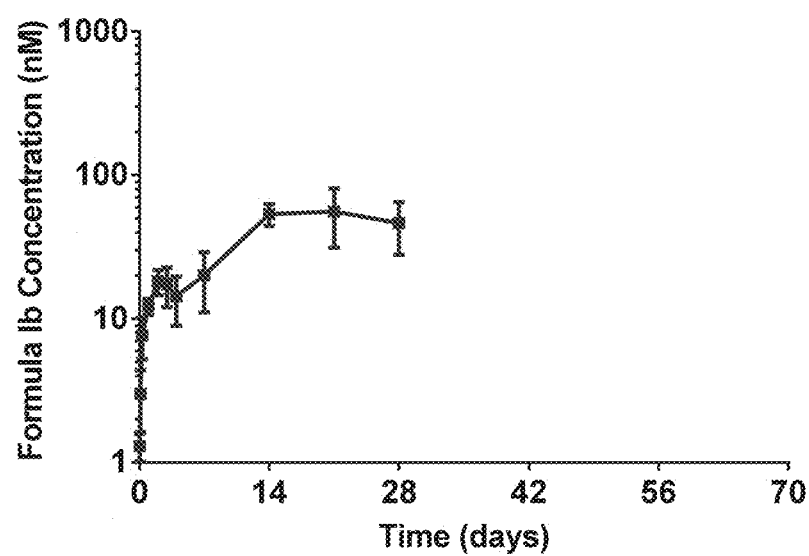
FIG. 10 shows a plot of plasma concentration over time of 200 mg/mL of Formula Ib in 10% ethanol, 12% water, and 78% PEG 200 when dosed subcutaneously in subjects at 6 mg/kg.

A solution formulation of a compound of Formula Ib in 10% ethanol, 12% water, and 78% PEG 200 (200 mg/ml) was prepared. The solution was administered to dogs subcutaneously at a dose of 6 mg/kg and the pharmacokinetic (PK) profile was determined. FIG. 10 shows a plot of the plasma concentration of the compound of Formula Ib as a function of time. As the data shows in FIG. 10, the compound of Formula Ib has measurable plasma concentrations at day 28 demonstrating extended release pharmacokinetics.

Figure 11:
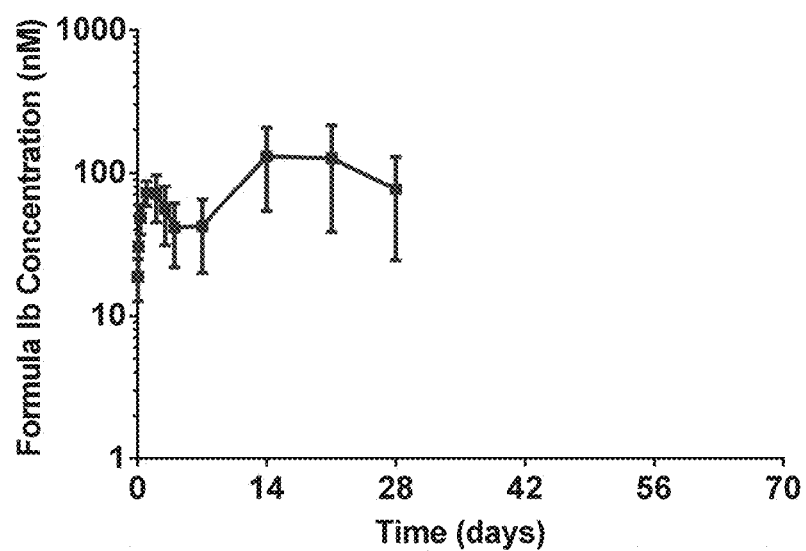
FIG. 11 shows a plot of plasma concentration over time of 200 mg/mL of Formula Ib, in situ salt, in 10% ethanol, 12% water, and 77% PEG 200 when dosed subcutaneously in subjects at 6 mg/kg.

A solution formulation containing 200 mg/mL of Formula Ib with 1.2 molar equivalent NaOH to form in situ sodium salt in 10% ethanol, 12% water, and 77% PEG are provided. Subjects were orally dosed with this formulation at 6 mg/kg. A solution of the the compound of Formula Ib in 10% ethanol, 12% water, and 7% PEG 200 (200 mg/ml) with 1.2 molar equivalent NaOH was prepared to form in situ sodium salt. The solution was administered to dogs subcutaneously at a dose of 6 mg/kg and the pharmacokinetic (PK) profile was determined. FIG. 11 shows a plot of the plasma concentration of the compound of Formula Ib as a function of time. As the data shows in FIG. 11, the compound of Formula Ib has measurable plasma concentrations at day 28 demonstrating extended release pharmacokinetics.

Figure 12:
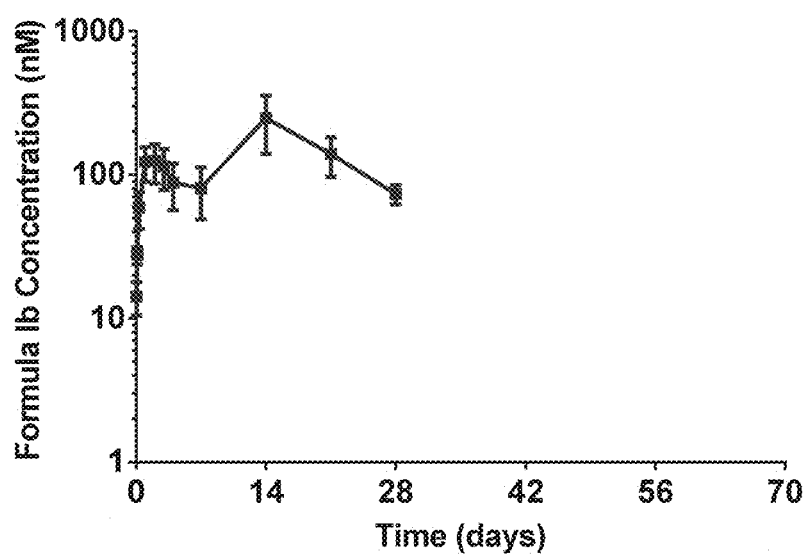
FIG. 12 shows a plot of plasma concentration over time of 200 mg/mL of Formula Ib in 10% ethanol, 13% water, and 77% glycofurol, with 1.2 mol-eq. NaOH to form in situ Na salt when dosed in subjects at 6 mg/kg.

A solution formulation of the compound of Formula Ib in 10% ethanol, 13% water, and 77% glycofurol (200 mg/mL) with 1.2 molar equivalent NaOH was prepared to form in situ sodium salt. The solution was administered to dogs subcutaneously at a dose of 6 mg/kg and the pharmacokinetic (PK) profile was determined. FIG. 12 shows a plot of the plasma concentration of the compound of Formula Ib as a function of time. As the data shows in FIG. 12, the compound of Formula Ib has measurable plasma concentrations at day 28 demonstrating extended release pharmacokinetics.

Oral Formulation Example

Figure 13:
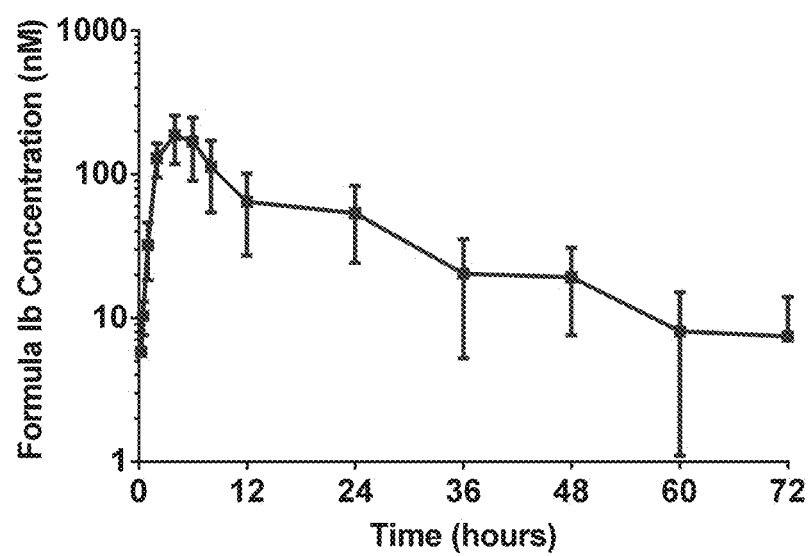
FIG. 13 shows a plot of plasma concentration over time of a fixed 7.5 mg oral dose of Formula Ib in 10% ethanol, 20% Vitamin E TPGS, 70% MIGLYOL 812 in dogs.

An oral formulation containing a compound of Formula Ib in 10% ethanol, 20% Vitamin E TPGS, and 70% MIGLYOL 812 was prepared in hard gelatin capsules was preapared. Dogs were orally given a fixed 7.5 mg dose of the compound of Formula Ib and the pharmacokinetic (PK) profile was determined. FIG. 13 shows the change in plasma concentration over time for the compound of Formula Ib.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure.

What is claimed is:

1. A compound of Formula (Ia):

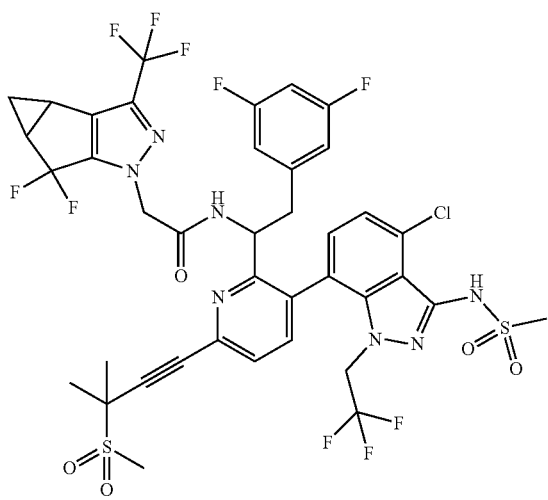

(Ia)

or a pharmaceutically acceptable salt thereof.

2. The compound of claim 1, which is a compound of Formula (Ib)

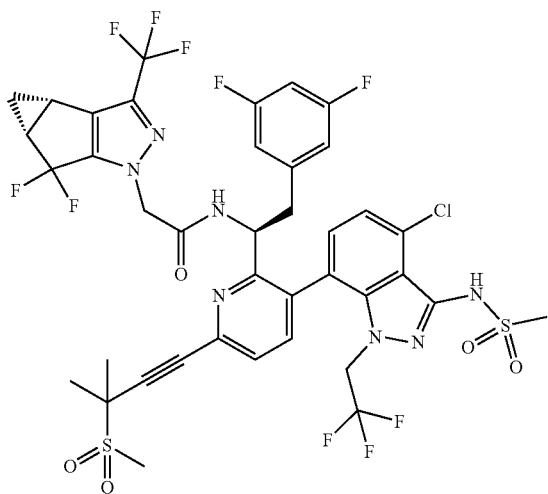

(Ib)

or a pharmaceutically acceptable salt thereof.

3. A pharmaceutical composition comprising a therapeutically effective amount of the compound of claim 2, or a pharmaceutically acceptable salt thereof, and a pharmaceutically acceptable excipient.

4. A compound of Formula (IIa):

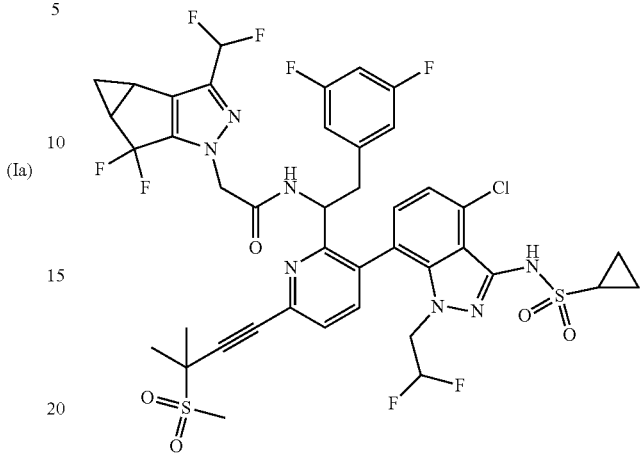

(IIa)

or a pharmaceutically acceptable salt thereof.

5. The compound of claim 4, which is a compound of Formula (IIb)

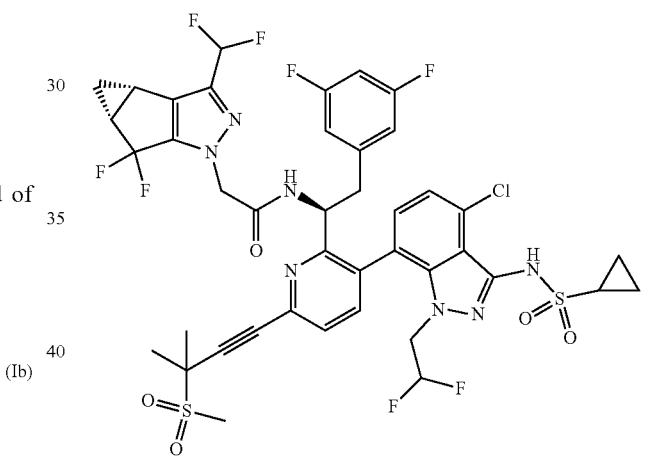

(IIb)

or a pharmaceutically acceptable salt thereof.

6. A pharmaceutical composition comprising a therapeutically effective amount of the compound of claim 5, or a pharmaceutically acceptable salt thereof, and a pharmaceutically acceptable excipient.

7. The pharmaceutical composition of claim 3, wherein the composition is suitable for oral administration.

8. The pharmaceutical composition of claim 7, wherein the composition is a capsule.

9. The pharmaceutical composition of claim 8, wherein the capsule is a hard capsule.

10. The pharmaceutical composition of claim 8, wherein the capsule is a soft capsule.

11. The pharmaceutical composition of claim 7, wherein the composition comprises a dosage amount from 1 mg to 1000 mg.

12. The pharmaceutical composition of claim 11, wherein the composition comprises a dosage amount from 10 mg to 50 mg.

13. The pharmaceutical composition of claim 11, wherein the composition comprises a dosage amount from 50 mg to 300 mg.

14. The pharmaceutical composition of claim 11, wherein the composition comprises a dosage amount from 300 mg to 1000 mg.

15. The compound of claim 2, wherein the compound is an amorphous solid.

16. The pharmaceutical composition of claim 6, wherein the composition is suitable for oral administration.

17. The pharmaceutical composition of claim 16, wherein the composition is a capsule.

18. The pharmaceutical composition of claim 17, wherein the capsule is a hard capsule.

19. The pharmaceutical composition of claim 17, wherein the capsule is a soft capsule.

20. The pharmaceutical composition of claim 16, wherein the composition comprises a dosage amount from 1 mg to 1000 mg.

21. The pharmaceutical composition of claim 20, wherein the composition comprises a dosage amount from 10 mg to 50 mg.

22. The pharmaceutical composition of claim 20, wherein the composition comprises a dosage amount from 50 mg to 300 mg.

23. The pharmaceutical composition of claim 20, wherein the composition comprises a dosage amount from 300 mg to 1000 mg.

24. The compound of claim 5, wherein the compound is a pharmaceutically acceptable salt.

25. The compound of claim 24, wherein the compound is a trifluoroacetic acid salt.

* * * * *